US011344696B2

(12) United States Patent
Choi et al.

(10) Patent No.: US 11,344,696 B2
(45) Date of Patent: May 31, 2022

(54) HUB OF INTELLIGENT IOT FOR LIGHT THERAPY AND LIGHT THERAPY METHOD BASED ON IOT

(71) Applicant: LG Electronics Inc., Seoul (KR)

(72) Inventors: Byunghun Choi, Seoul (KR); Boemoh Kim, Seoul (KR)

(73) Assignee: LG Electronics Inc., Seoul (KR)

(*) Notice: Subject to any disclaimer, the term of this patent is extended or adjusted under 35 U.S.C. 154(b) by 322 days.

(21) Appl. No.: 16/489,903

(22) PCT Filed: May 31, 2019

(86) PCT No.: PCT/KR2019/006592
§ 371 (c)(1),
(2) Date: Aug. 29, 2019

(87) PCT Pub. No.: WO2020/241945
PCT Pub. Date: Dec. 3, 2020

(65) Prior Publication Data
US 2020/0345969 A1   Nov. 5, 2020

(51) Int. Cl.
*A61M 21/02* (2006.01)
*G16H 40/60* (2018.01)
*A61M 21/00* (2006.01)

(52) U.S. Cl.
CPC ............ *A61M 21/02* (2013.01); *G16H 40/60* (2018.01); *A61M 2021/0083* (2013.01); *A61M 2205/3553* (2013.01); *A61M 2230/00* (2013.01)

(58) Field of Classification Search
CPC .............. A61M 21/02; A61M 2230/00; A61M 2205/3553; A61M 2021/0083;
(Continued)

(56) References Cited

U.S. PATENT DOCUMENTS

2007/0083079 A1* 4/2007 Lee ....................... A61M 21/00
600/27
2016/0217672 A1* 7/2016 Yoon ................... A61B 5/02055
(Continued)

FOREIGN PATENT DOCUMENTS

KR    20160012780    7/2014
KR    20170074364    6/2017
(Continued)

*Primary Examiner* — Sunita Reddy
(74) *Attorney, Agent, or Firm* — Fish & Richardson P.C.

(57) ABSTRACT

A hub of intelligent Internet of Things (IoT) for performing a light therapy using light irradiated by a light output device. The hub of intelligent IoT includes a sleep disorder reading unit determining whether a sleep disorder has occurred based on sleep pattern information; a control signal generator generating a control signal for controlling the light output device when it is determined that the sleep disorder has occurred; and a communication interface unit providing the control signal to the light output device. At least one device implementing the method of providing the intelligent voice recognition model may be associated with an artificial intelligence module, a unmanned aerial vehicle (UAV), a robot, an augmented reality (AR) device, a virtual reality (VR) device, devices related to 5G services, and the like.

4 Claims, 39 Drawing Sheets

(58) Field of Classification Search
CPC ........ A61M 2205/505; A61M 2230/60; A61M 2230/205; A61M 2230/40; A61M 2230/50; A61M 2230/06; A61M 2230/42; A61M 2230/63; A61M 2205/3375; A61M 2209/088; A61M 2230/14; A61M 2230/10; A61M 2230/04; A61M 2205/3592; A61M 2205/3584; A61M 2021/0044; G16H 40/60; G16H 50/20; G16H 20/40; A61N 2005/0626; A61N 5/0618
USPC ..................................................... 600/26–28
See application file for complete search history.

(56) References Cited

U.S. PATENT DOCUMENTS

2018/0339127 A1* 11/2018 Van Reen ............. A61N 5/0618
2019/0209806 A1* 7/2019 Allen .................... G16H 20/70

FOREIGN PATENT DOCUMENTS

| KR | 101768524 | 8/2017 |
| KR | 20170096621 | 8/2017 |
| KR | 20180031541 | 3/2018 |

* cited by examiner

Fig. Uplink TX procedure with grant

Fig. Uplink TX procedure without grant (a)

(b)

(a) In-band system (b) Guard-band system (c) Stand-alone system

HUB OF INTELLIGENT IOT FOR LIGHT THERAPY AND LIGHT THERAPY METHOD BASED ON IOT

CROSS-REFERENCE TO RELATED APPLICATIONS

This application is a National Stage application under 35 U.S.C. § 371 of International Application No. PCT/KR2019/006592, filed on May 31, 2019, the disclosure of which is hereby incorporated by reference in its entirety.

TECHNICAL FIELD

The present invention relates to a hub of intelligent Internet of Things (IoT) for light therapy and a light therapy method based on IoT, and more particularly to a method of performing light therapy based on monitoring a user's sleep time in real time.

BACKGROUND ART

The importance of sleep and its effects on human health are well known. As a sleep start time to enter the sleep and a wake-up time to wake up become constant, the health becomes better. It is important to sufficiently ensure a sleep duration from the sleep start time to the wake-up time.

However, there are cases where the sleep duration cannot be kept constant due to various work forms. If you move to a region with a time difference in a short time, there may be a trouble in a sleep cycle before you adjust to the time difference. The sleep quality may be reduce due to psychological or physiological factors.

As described above, sleep disorders occur in various forms, which have harmful effects on physical and mental health.

In order to improve the sleep disorders, devices and methods for helping sleep are used. Even if the method for helping sleep is used, it is impossible to fundamentally improve the sleep disorders. Thus, active measures for sleep disorders are required. In particular, since a sleep pattern of a user may change in real time, more active treatment for the sleep disorders is required.

DISCLOSURE

Technical Problem

An object of the present invention is to address the above-described and other problems.

Another object of the present invention is to provide a hub of intelligent Internet of Things (IoT) for light therapy and a light therapy method based on IoT capable of improving adverse effects of sleep disorders.

Another object of the present invention is to provide a hub of intelligent Internet of Things (IoT) for light therapy and a light therapy method based on IoT capable of treating sleep disorders in response to a real-time sleep pattern of a user.

Technical Solution

In one aspect, there is provided a hub of intelligent Internet of Things (IoT) for light therapy comprising a sleep disorder reading unit configured to determine whether a sleep disorder has occurred based on sleep pattern information, a control signal generator configured to generate a control signal for controlling the light output device when it is determined that the sleep disorder has occurred, and a communication interface unit configured to provide the control signal to the light output device.

The hub of intelligent IoT for light therapy may further comprise a sleep pattern information acquisition unit configured to acquire the sleep pattern information based on biometric information received from the outside.

The sleep disorder reading unit detects a sleep start time and a wake-up time in the sleep pattern information, and determines that the sleep disorder has occurred if the sleep start time and the wake-up time are out of a sleep start time and a wake-up time of a normal sleep time by a critical value or more.

The sleep disorder reading unit may determine that the sleep disorder has occurred if the sleep pattern information corresponds to a predetermined sleep pattern of a sleep disorder.

The hub of intelligent IoT for light therapy may further comprise a database configured to store light therapy conditions matched to the sleep pattern of the sleep disorder. The control signal generator may generate the control signal for controlling a light therapy time and an illuminance to match the light therapy conditions.

The control signal may include a turn-on signal for controlling a turn-on of the light output device, a turn-off signal for controlling a turn-off of the light output device, and an illuminance adjusting signal for adjusting an intensity of light irradiated by the light output device.

The illuminance adjusting signal may control an illuminance of the light output device according to the sleep pattern information.

In another aspect, there is provided a method for performing a light therapy by controlling a light output device based on Internet of Things (IoT), the method comprising monitoring a sleep state of a user, analyzing the sleep state to acquire sleep pattern information, determining whether a sleep disorder has occurred based on the sleep pattern information, and generating a control signal for controlling the light output device when it is determined that the sleep disorder has occurred.

The monitoring of the sleep state may comprise acquiring biometric information of a user, and detecting in real time a sleep phase change based on the biometric information.

The acquiring of the biometric information may comprise directly measuring the biometric information of the user using a biometric signal acquisition device contacting the user.

The acquiring of the biometric information may comprise sending a radar signal to the user, receiving a reflected wave on which the radar signal is reflected from the user, and detecting a frequency, that varies depending on changes in a biometric signal of the user, among frequencies of the reflected wave.

The determining whether the sleep disorder has occurred may comprise detecting a sleep start time and a wake-up time in a sleep phase, and determining that the sleep disorder has occurred if the sleep start time and the wake-up time are out of a sleep start time and a wake-up time of a normal sleep time by a critical value or more.

The determining whether the sleep disorder has occurred may comprise determining whether the sleep disorder has occurred if the sleep pattern information corresponds to a predetermined sleep pattern of a sleep disorder.

The generating of the control signal may comprise checking light therapy conditions matched to the sleep pattern of the sleep disorder, setting an operation time of the light output device corresponding to the light therapy conditions, and generating an illuminance adjusting signal for controlling an illuminance of the light output device so as to correspond to the light therapy conditions.

The method may further comprise, after generating the control signal, sending a turn-on signal for turning on the light output device to the light output device, counting the operation time, and sending a turn-off signal for turning off the light output device to the light output device after the operation time has passed from a time when the turn-on signal is sent.

Advantageous Effects

Effects of a method of providing a hub of intelligent Internet of Things (IoT) for light therapy and a light therapy method based on IoT according to the present invention are described as follows.

The present invention can improve adverse effects of sleep disorders by performing light therapy when the sleep disorder has occurred in a sleep time.

In particular, the present invention can perform light therapy for sleep disorders immediately after waking from sleep because it can be decided that a sleep disorder has occurred based on monitoring a sleep state in real time.

MODE FOR INVENTION

Hereinafter, embodiments of the disclosure will be described in detail with reference to the attached drawings. The same or similar components are given the same reference numbers and redundant description thereof is omitted. The suffixes "module" and "unit" of elements herein are used for convenience of description and thus may be used interchangeably and do not have any distinguishable meanings or functions. Further, in the following description, if a detailed description of known techniques associated with the present invention would unnecessarily obscure the gist of the present invention, detailed description thereof will be omitted. In addition, the attached drawings are provided for easy understanding of embodiments of the disclosure and do not limit technical spirits of the disclosure, and the embodiments should be construed as including all modifications, equivalents, and alternatives falling within the spirit and scope of the embodiments.

While terms, such as "first", "second", etc., may be used to describe various components, such components must not be limited by the above terms. The above terms are used only to distinguish one component from another.

When an element is "coupled" or "connected" to another element, it should be understood that a third element may be present between the two elements although the element may be directly coupled or connected to the other element. When an element is "directly coupled" or "directly connected" to another element, it should be understood that no element is present between the two elements.

The singular forms are intended to include the plural forms as well, unless the context clearly indicates otherwise.

In addition, in the specification, it will be further understood that the terms "comprise" and "include" specify the presence of stated features, integers, steps, operations, elements, components, and/or combinations thereof, but do not preclude the presence or addition of one or more other features, integers, steps, operations, elements, components, and/or combinations.

A. Example of Autonomous Vehicle and 5G Network

Figure 1:
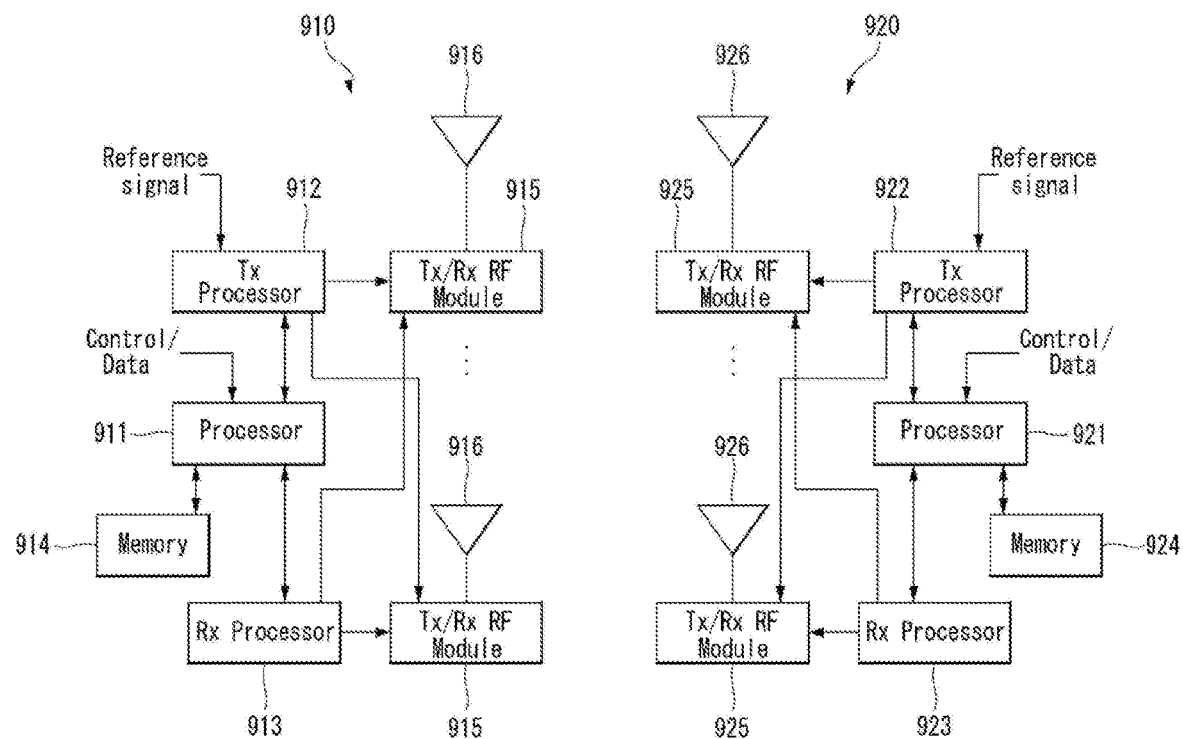
FIG. 1 is a block diagram of a wireless communication system to which the methods proposed herein may be applied.

FIG. 1 is a block diagram of a wireless communication system to which methods proposed in the disclosure are applicable.

Referring to FIG. 1, a device including an autonomous driving module is defined as a first communication device (910 of FIG. 1 and see paragraph N for detailed description), and a processor 911 may perform detailed autonomous driving operations.

Another vehicle or a 5G network communicating with the autonomous driving device is defined as a second communication device (920 of FIG. 1, and see paragraph N for details), and a processor 921 may perform detailed autonomous driving operations.

Details of a wireless communication system, which is defined as including a first communication device, which is an autonomous vehicle, and a second communication device, which is a 5G network, may refer to paragraph N.

B. AI Operation Using 5G Communication

Figure 2:
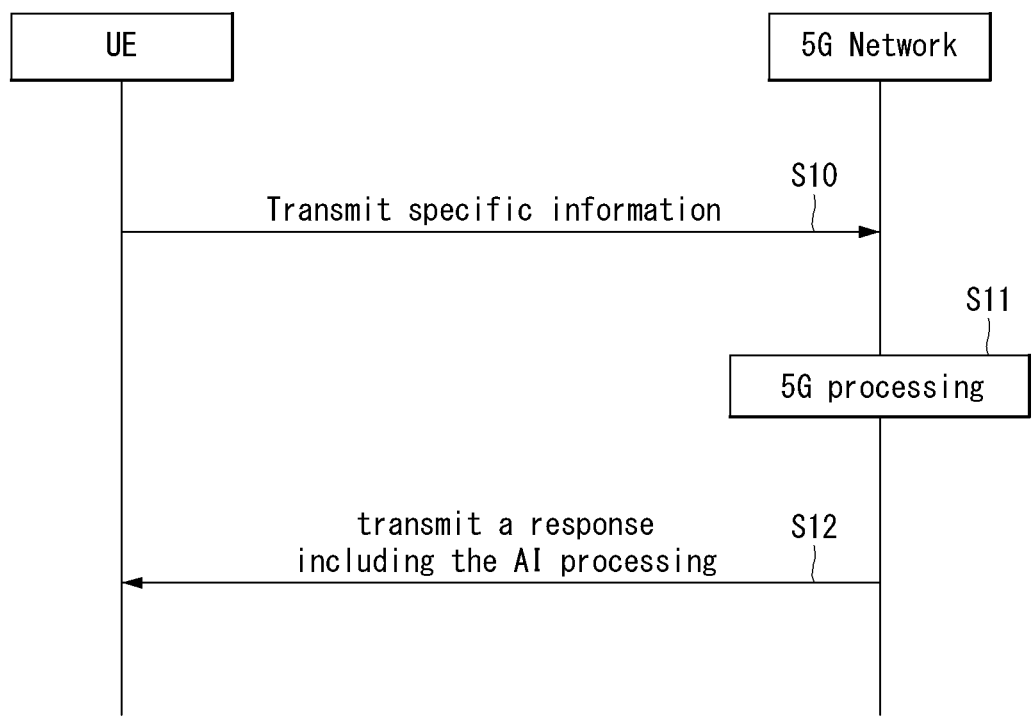
FIG. 2 shows an example of a basic operation of an user equipment and a 5G network in a 5G communication system.

FIG. 2 shows an example of a basic operation of a user equipment and a 5G network in a 5G communication system.

The UE transmits the specific information transmission to the 5G network (S1).

Then, the 5G network performs 5G processing on the specific information (S2).

In this connection, the 5G processing may include AI processing.

Then, the 5G network transmits a response including the AI processing result to the UE (S3).

Figure 3:
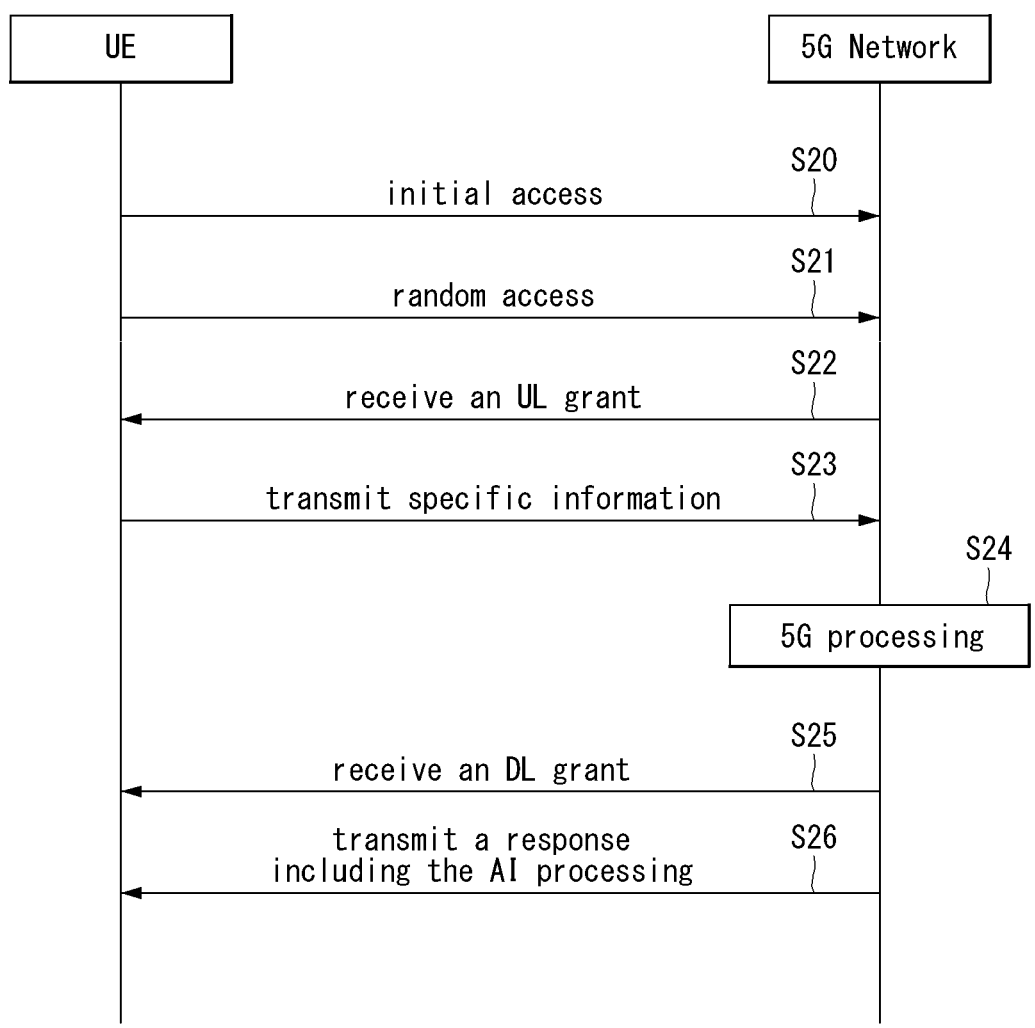
FIG. 3 illustrates an example of application operation of an user equipment and a 5G network in a 5G communication system.

FIG. 3 shows an example of application operation of a user terminal and a 5G network in a 5G communication system.

The UE performs an initial access procedure with the 5G network (S20). The initial connection procedure will be described in more detail in paragraph F.

Then, the UE performs a random access procedure with the 5G network (S21). The random access procedure will be described in more detail in paragraph G.

The 5G network transmits an UL grant for scheduling transmission of specific information to the UE (S22). The process of the UE receiving the UL grant will be described in more detail in the UL transmission/reception operation in paragraph H.

Then, the UE transmits specific information to the 5G network based on the UL grant (S23).

Then, the 5G network performs 5G processing on the specific information (S24).

In this connection, the 5G processing may include AI processing.

Then, the 5G network transmits a DL grant for scheduling transmission of the 5G processing result of the specific information to the UE (S25).

Then, the 5G network transmits a response including the AI processing result to the UE based on the DL grant (S26).

In FIG. 3, an example in which the AI operation and the initial connection process, or the random access process and the DL grant reception process are combined with each other has been exemplarily described using the S20 to S26. However, the present invention is not limited thereto.

For example, the initial connection process and/or the random access process may be performed using the process of S20, S22, S23, S24, and S24. In addition, the initial connection process and/or the random access process may be performed using, for example, the process of S21, S22, S23, S24, and S26. Further, the AI operation and the downlink grant reception procedure may be combined with each other using the process of S23, S24, S25, and S26.

C. UE Operation Using 5G Communication

FIG. 4 to FIG. 7 show an example of the operation of the UE using 5G communication.

Figure 4:
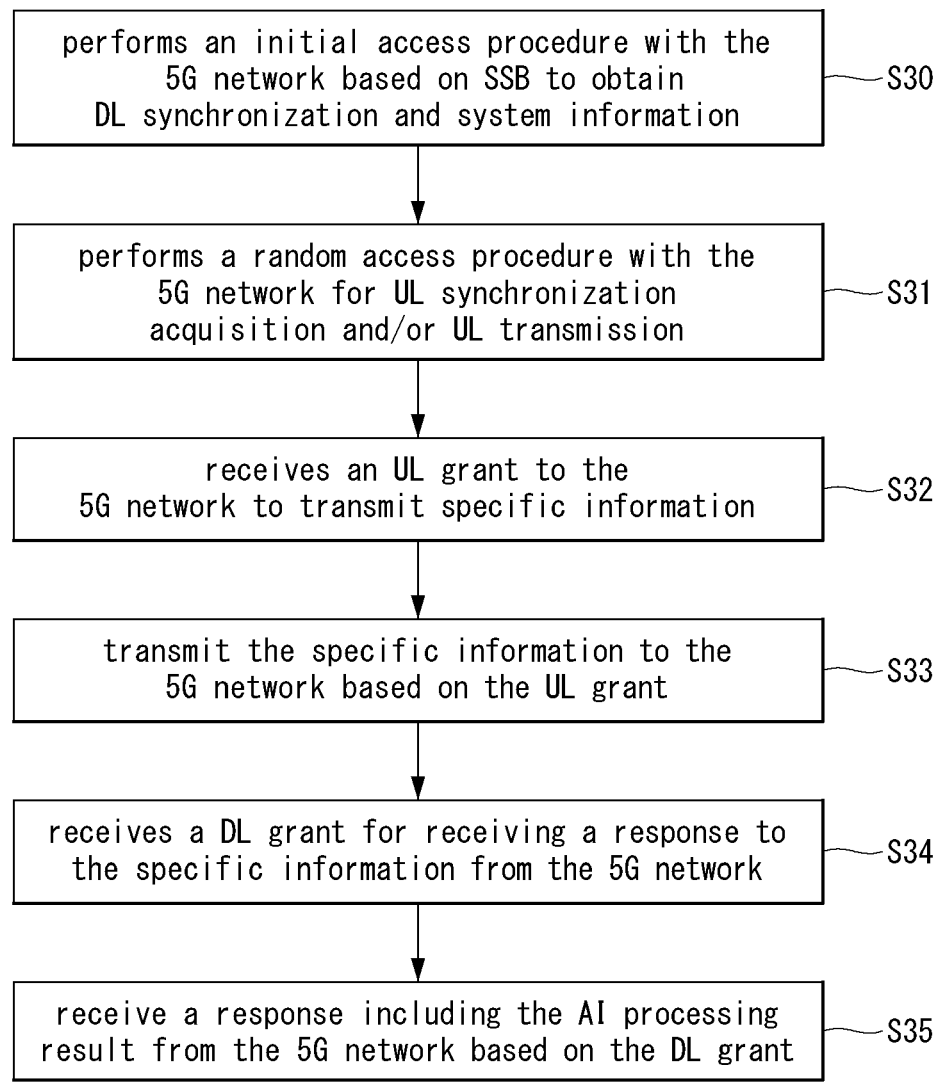
FIGS. 4 to 7 show an example of an operation of an user equipment using 5G communication.

Referring first to FIG. 4, the UE performs an initial access procedure with the 5G network based on SSB to obtain DL synchronization and system information (S30).

Then, the UE performs a random access procedure with the 5G network for UL synchronization acquisition and/or UL transmission (S31).

Then, the UE receives an UL grant to the 5G network to transmit specific information (S32).

Then, the UE transmits the specific information to the 5G network based on the UL grant (S33).

Then, the UE receives a DL grant for receiving a response to the specific information from the 5G network (S34).

Then, the UE receives a response including the AI processing result from the 5G network based on the DL grant (S35).

A beam management (BM) process may be added to S30. A beam failure recovery process may be added to S31. A quasi-co location relationship may be added to S32 to S35. A more detailed description thereof will be described in more detail in paragraph I.

Figure 5:
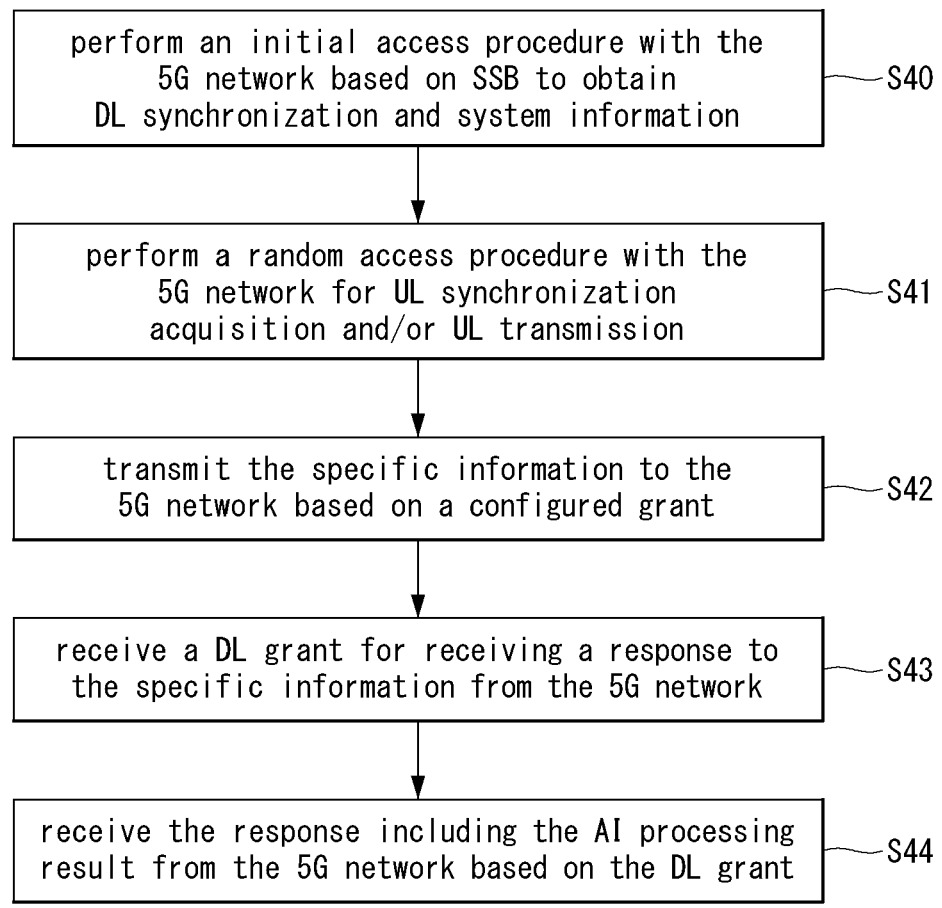

Next, referring to FIG. 5, the UE performs an initial access procedure with the 5G network based on SSB to obtain DL synchronization and system information (S40).

Then, the UE performs a random access procedure with the 5G network for UL synchronization acquisition and/or UL transmission (S41).

Then, the UE transmits the specific information to the 5G network based on a configured grant (S42). A procedure for configuring the grant in place of receiving the UL grant from the 5G network will be described in more detail in paragraph H.

Then, the UE receives a DL grant for receiving a response to the specific information from the 5G network (S43).

Then, the UE receives the response including the AI processing result from the 5G network based on the DL grant (S44).

Figure 6:
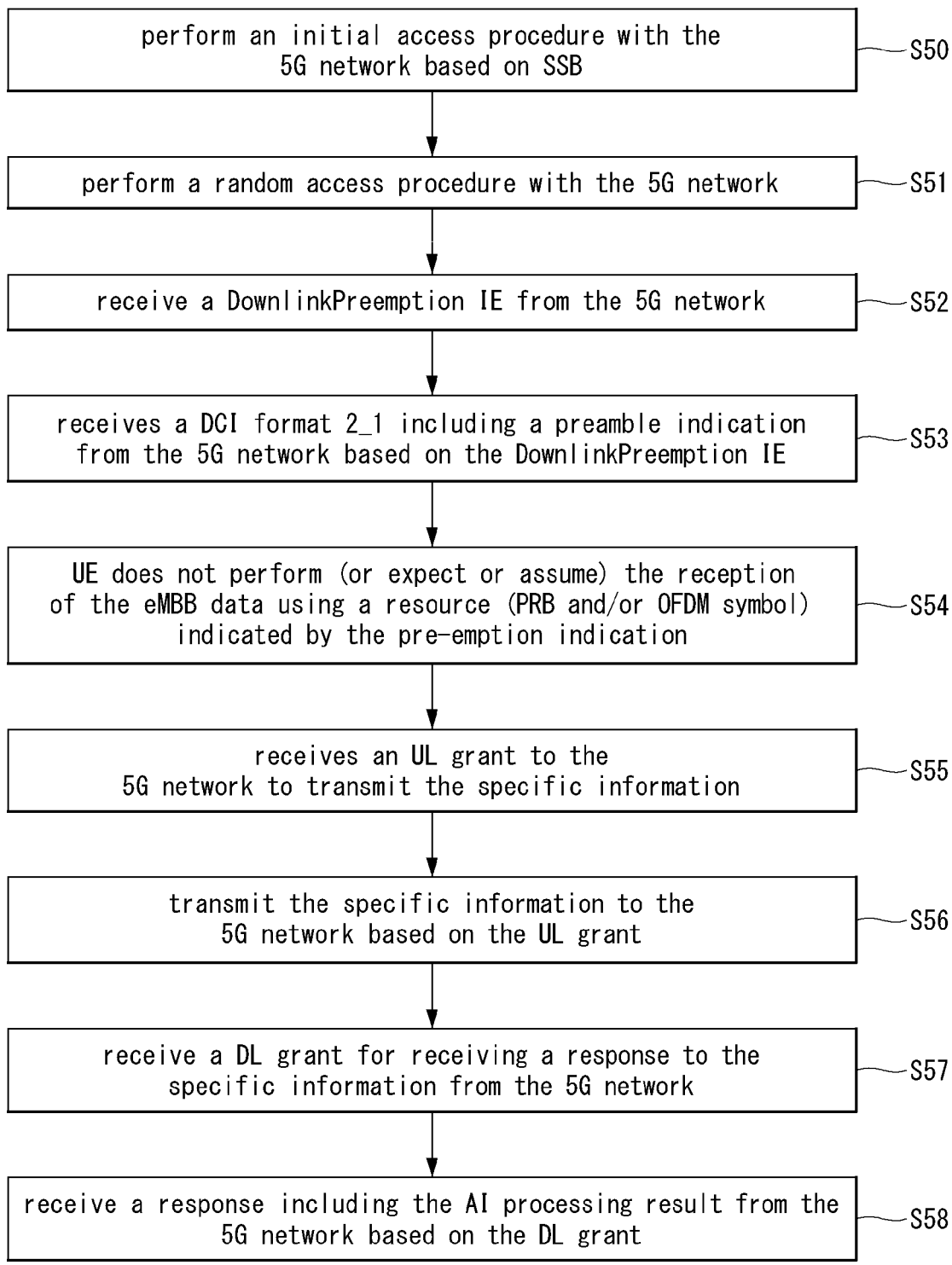

Next, referring to FIG. 6, the UE performs an initial access procedure with the 5G network based on the SSB to obtain DL synchronization and system information (S50).

Then, the UE performs a random access procedure with the 5G network for UL synchronization acquisition and/or UL transmission (S51).

Then, the UE receives a DownlinkPreemption IE from the 5G network (S52).

The UE receives a DCI format 2_1 including a preamble indication from the 5G network based on the DownlinkPre-emption IE (S53).

Then, the UE does not perform (or expect or assume) the reception of the eMBB data using a resource (PRB and/or OFDM symbol) indicated by the pre-emption indication (S54).

The operation related to the preemption indication is described in more detail in paragraph J.

Then, the UE receives an UL grant to the 5G network to transmit the specific information (S55).

Then, the UE transmits the specific information to the 5G network based on the UL grant (S56).

Then, the UE receives a DL grant for receiving a response to the specific information from the 5G network (S57).

Then, the UE receives a response including the AI processing result from the 5G network based on the DL grant (S58).

Figure 7:
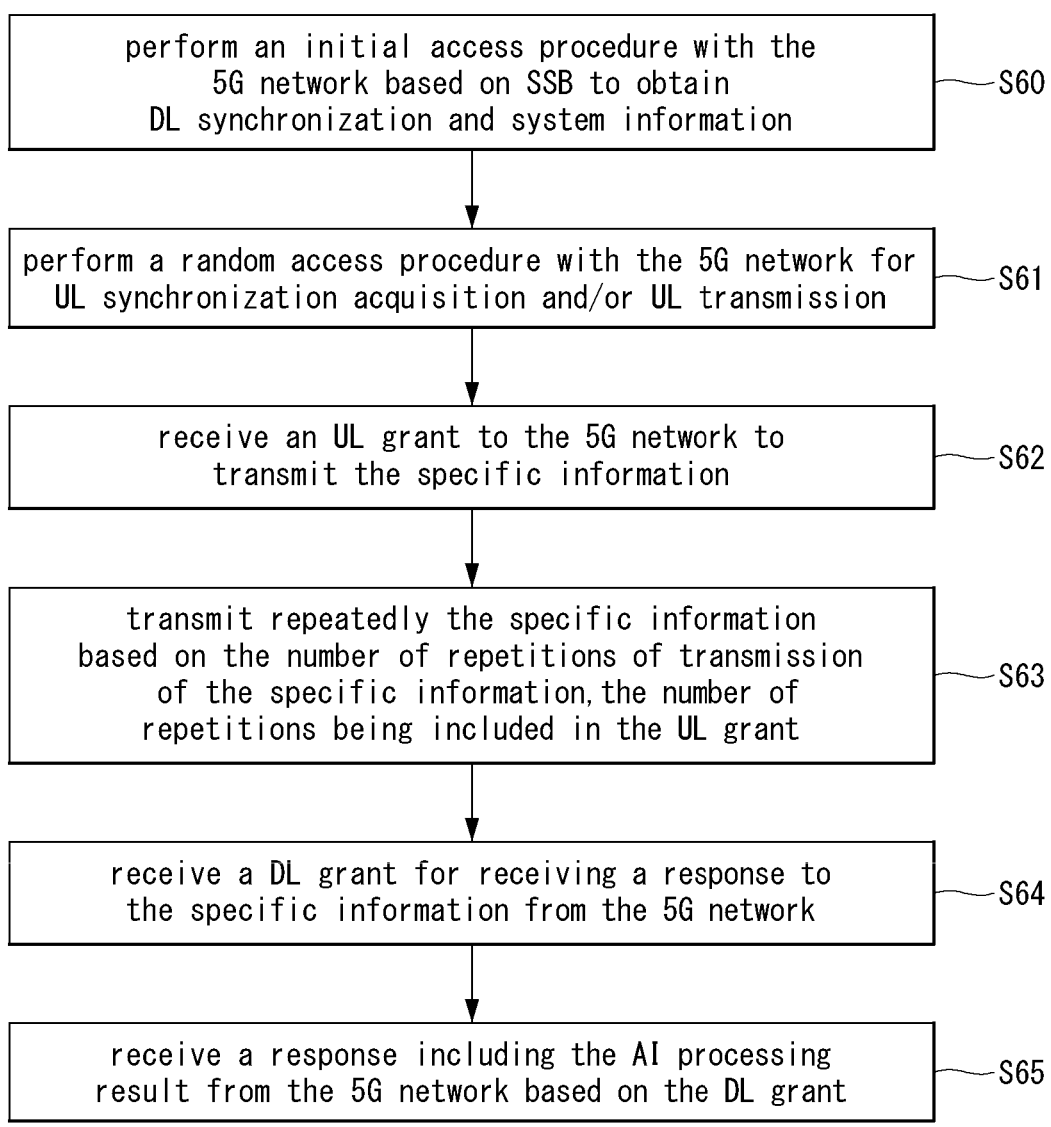

Next, referring to FIG. 7, the UE performs an initial access procedure with the 5G network based on SSB to obtain DL synchronization and system information (S60).

Then, the UE performs a random access procedure with the 5G network for UL synchronization acquisition and/or UL transmission (S61).

Then, the UE receives an UL grant to the 5G network to transmit the specific information (S62).

The UL grant includes information on the number of repetitions of transmission of the specific information. The specific information is repeatedly transmitted based on the information on the repetition number (S63).

The UE transmits the specific information to the 5G network based on the UL grant.

Then, the iterative transmission of the specific information is performed using the frequency hopping. The first transmission of the specific information may be done using a first frequency resource, and the second transmission of the specific information may be done using a second frequency resource.

The specific information may be transmitted over a narrow band of 6RB (Resource Block) or 1RB (Resource Block).

Then, the UE receives a DL grant for receiving a response to the specific information from the 5G network (S64).

Then, the UE receives a response including the AI processing result from the 5G network based on the DL grant (S65).

The mMTC described in FIG. 7 will be described in more detail in the paragraph K.

D. Introduction

Hereinafter, downlink (DL) refers to communication from a base station (BS) to user equipment (UE), and uplink (UL) refers to communication from a UE to a BS. In the downlink, a transmitter may be part of the BS and a receiver may be part of the UE. In the uplink, a transmitter may be part of the UE and a receiver may be part of the BS. Herein, the UE may be represented as a first communication device and the BS may be represented as a second communication device. The BS may be replaced with a term such as a fixed station, a Node B, an evolved NodeB (eNB), a next generation nodeB (gNB), a base transceiver system (BTS), an access point (AP), a network or a 5G (5th generation), artificial intelligence (AI) system, a road side unit (RSU), robot, and the like. Also, the UE may be replaced with a terminal, a mobile station (MS), a user terminal (UT), a mobile subscriber station (MSS), a subscriber station (SS), an advanced mobile station (AMS), a wireless terminal (WT), a machine-type communication (MTC) device, a machine-to-machine (M2M) device, a device-to-device (D2D) device, a vehicle, a robot, an AI module, and the like.

Techniques described herein may be used in a variety of wireless access systems such as Code Division Multiple Access (CDMA), Frequency Division Multiple Access (FDMA), Time Division Multiple Access (TDMA), Orthogonal Frequency Division Multiple Access (OFDMA), Single Carrier Frequency Division Multiple Access (SC-FDMA), etc. CDMA may be implemented as a radio technology such as Universal Terrestrial Radio Access (UTRA) or CDMA2000. TDMA may be implemented as a radio technology such as Global System for Mobile communications (GSM)/General Packet Radio Service (GPRS)/Enhanced Data Rates for GSM Evolution (EDGE). OFDMA may be implemented as a radio technology such as IEEE 802.11 (Wi-Fi), IEEE 802.16 (WiMAX), IEEE 802.20, Evolved-UTRA (E-UTRA) etc. UTRA is a part of Universal Mobile Telecommunications System (UMTS). 3rd Generation Partnership Project (3GPP) Long Term Evolution (LTE) is a part of Evolved UMTS (E-UMTS) using E-UTRA. LTE-Advanced (LTE-A)/LTE-A pro is an evolution of 3GPP LTE. 3GPP NR NR(New Radio or New Radio Access Technology) is an evolution of 3GPP LTE/LTE-A/LTE-A pro.

For clarity, the following description focuses on a 3GPP communication system (e.g., LTE-A, NR), but technical features of the present invention is not limited thereto. LTE refers to technology after 3GPP TS 36.xxx Release 8. In detail, LTE technology after 3GPP TS 36.xxx Release 10 is referred to as LTE-A, and LTE technology after 3GPP TS 36.xxx Release 13 is referred to as LTE-A pro. 3GPP 5G (5th generation) technology refers to technology after TS 36.xxx Release 15 and technology after TS 38.XXX Release 15. The technology after TS 38.xxx Release 15 may be referred to as 3GPP NR, and technology after TS 36.xxx Release 15 may be referred to as enhanced LTE. "xxx" refers to a standard document detail number. LTE/NR may be collectively referred to as a 3GPP system.

In this disclosure, a node refers to a fixed point capable of transmitting/receiving a radio signal through communication with a UE. Various types of BSs may be used as nodes irrespective of the terms thereof. For example, a BS, a node B (NB), an e-node B (eNB), a pico-cell eNB (PeNB), a home eNB (HeNB), a relay, a repeater, etc. may be a node. In addition, the node may not be a BS. For example, the node may be a radio remote head (RRH) or a radio remote unit (RRU). The RRH or RRU generally has a power level lower than a power level of a BS. At least one antenna is installed per node. The antenna may refer to a physical antenna or refer to an antenna port, a virtual antenna, or an antenna group. A node may be referred to as a point.

In this specification, a cell refers to a prescribed geographical area to which one or more nodes provide a communication service. A "cell" of a geographic region may be understood as coverage within which a node can provide a service using a carrier and a "cell" of a radio resource is associated with bandwidth (BW) which is a frequency range configured by the carrier. Since DL coverage, which is a range within which the node is capable of transmitting a valid signal, and UL coverage, which is a range within which the node is capable of receiving the valid signal from the UE, depends upon a carrier carrying the signal, coverage of the node may be associated with coverage of "cell" of a radio resource used by the node. Accordingly, the term "cell" may be used to indicate service coverage by the node sometimes, a radio resource at other times, or a range that a signal using a radio resource can reach with valid strength at other times.

In this specification, communicating with a specific cell may refer to communicating with a BS or a node which provides a communication service to the specific cell. In addition, a DL/UL signal of a specific cell refers to a DL/UL signal from/to a BS or a node which provides a communication service to the specific cell. A node providing UL/DL communication services to a UE is called a serving node and a cell to which UL/DL communication services are provided by the serving node is especially called a serving cell. Furthermore, channel status/quality of a specific cell refers to channel status/quality of a channel or communication link formed between a BS or node which provides a communication service to the specific cell and a UE.

Meanwhile, a "cell" associated with radio resource may be defined as a combination of DL resources and UL resources, that is, a combination of a DL component carrier (CC) and a UL CC. A cell may be configured to be a DL resource alone or a combination of DL resources and UL resources. If carrier aggregation is supported, a linkage between a carrier frequency of a DL resource (or DL CC) and a carrier frequency of a UL resource (or UL CC) may be indicated by system information transmitted through a corresponding cell. Here, the carrier frequency may be the same as or different from a center frequency of each cell or CC. Hereinafter, a cell operating at a primary frequency will be referred to as a primary cell (Pcell) or a PCC, and a cell operating at a secondary frequency will be referred to as a secondary cell (Scell) Or SCC. The Scell may be configured after the UE performs a radio resource control (RRC) connection establishment with the BS to establish an RRC connection therebetween, that is, after the UE is RRC_CONNECTED. Here, RRC connection may refer to a channel through which an RRC of the UE and an RRC of the BS may exchange RRC messages with each other. The Scell may be configured to provide additional radio resources to the UE. Depending on the capabilities of the UE, the Scell may form a set of serving cells for the UE together with the Pcell. In the case of a UE which is in the RRC_CONNECTED state but is not configured in carrier aggregation or does not support carrier aggregation, there is only one serving cell that is only configured as the Pcell.

Cells support unique wireless access technologies. For example, transmission/reception according to LTE radio access technology (RAT) is performed on an LTE cell, and transmission/reception according to 5G RAT is performed on a 5G cell.

A carrier aggregation (CA) system refers to a system for supporting a wide bandwidth by aggregating a plurality of carriers each having a narrower bandwidth than a target bandwidth. A CA system is different from OFDMA technology in that DL or UL communication is performed using a plurality of carrier frequencies each of which forms a system bandwidth (or a channel bandwidth), whereas the OFDM system carries a base frequency band divided into a plurality of orthogonal subcarriers on a single carrier frequency to perform DL or UL communication. For example, in the case of OFDMA or orthogonal frequency division multiplexing (OFDM), one frequency band having a constant system bandwidth is divided into a plurality of subcarriers having a certain subscriber spacing, and information/data is mapped in the plurality of subcarriers, and the frequency band to which the information/data is mapped is unconverted and transmitted as a carrier frequency of the frequency band. In the case of wireless carrier aggregation, frequency bands having their own system bandwidth and carrier frequency may be simultaneously used for communication, and each frequency band used for carrier aggregation may be divided into a plurality of subcarriers having a predetermined subcarrier spacing.

The 3GPP-based communication standard defines DL physical channels corresponding to resource elements carrying information derived from a higher layer of a physical layer (e.g., a medium access control (MAC) layer, a radio link control (RLC) layer, a packet data convergence protocol (PDCP) layer, a radio resource control (RRC) layer, a service data adaptation protocol (SDAP), and a non-access stratum (NAS) layer and DL physical signals corresponding to resource elements which are used by a physical layer but which do not carry information derived from a higher layer. For example, a physical downlink shared channel (PDSCH), a physical broadcast channel (PBCH), a physical multicast channel (PMCH), a physical control format indicator channel (PCFICH), and a physical downlink control channel (PDCCH) are defined as the DL physical channels, and a reference signal and a synchronization signal are defined as the DL physical signals. A reference signal (RS), also called a pilot, refers to a special waveform of a predefined signal known to both a BS and a UE. For example, a cell-specific RS (CRS), a UE-specific RS, a positioning RS (PRS), channel state information RS (CSI-RS), and a demodulation reference signal (DMRS) may be defined as DL RSs. Meanwhile, the 3GPP-based communication standards define UL physical channels corresponding to resource elements carrying information derived from a higher layer and UL physical signals corresponding to resource elements which are used by a physical layer but which do not carry information derived from a higher layer. For example, a physical uplink shared channel (PUSCH), a physical uplink control channel (PUCCH), and a physical random access channel (PRACH) are defined as the UL physical channels, and a demodulation reference signal (DM RS) for a UL control/data signal and a sounding reference signal (SRS) used for UL channel measurement are defined as the UL physical signals.

In this specification, a physical downlink control channel (PDCCH) and a physical downlink shared channel (PDSCH) may refer to a set of a time-frequency resources or a set of resource elements carrying downlink control information (DCI) and downlink data, respectively. In addition, a physical uplink control channel, a physical uplink shared channel (PUSCH), and a physical random access channel refer to a set of a time-frequency resources or a set of resource elements carrying uplink control information (UCI), uplink data and random access signals, respectively. Hereinafter, UE's transmitting an uplink physical channel (e.g., PUCCH, PUSCH, or PRACH) means transmitting UCI, uplink data, or a random access signal on the corresponding uplink physical channel or through then uplink physical channel. BS's receiving an uplink physical channel may refer to receiving DCI, uplink data, or random access signal on or through the uplink physical channel. BS's transmitting a downlink physical channel (e.g., PDCCH and PDSCH) has the same meaning as transmitting DCI or downlink data on or through the corresponding downlink physical channel. UE's receiving a downlink physical channel may refer to receiving DCI or downlink data on or through the corresponding downlink physical channel.

In this specification, a transport block is a payload for a physical layer. For example, data given to a physical layer from an upper layer or a medium access control (MAC) layer is basically referred to as a transport block.

In this specification, HARQ (Hybrid Automatic Repeat and reQuest) is a kind of error control method. HARQ-acknowledgement (HARQ-ACK) transmitted through the downlink is used for error control on uplink data, and HARQ-ACK transmitted on the uplink is used for error control on downlink data. A transmitter that performs the HARQ operation transmits data (e.g., a transport block, a codeword) and waits for an acknowledgment (ACK). A receiver that performs the HARQ operation sends an acknowledgment (ACK) only when data is properly received, and sends a negative acknowledgment (NACK) if an error occurs in the received data. The transmitter may transmit (new) data if ACK is received, and retransmit data if NACK is received. After the BS transmits scheduling information and data according to the scheduling information, a time delay occurs until the ACK/NACK is received from the UE and retransmission data is transmitted. This time delay occurs due to channel propagation delay and a time taken for data decoding/encoding. Therefore, when new data is sent after the current HARQ process is finished, a blank space occurs in the data transmission due to the time delay. Therefore, a plurality of independent HARQ processes are used to prevent generation of the blank space in data transmission during the time delay period. For example, if there are seven transmission occasions between an initial transmission and retransmission, the communication device may operate seven independent HARQ processes to perform data transmission without a blank space. Utilizing the plurality of parallel HARQ processes, UL/DL transmissions may be performed continuously while waiting for HARQ feedback for a previous UL/DL transmission.

In this specification, channel state information (CSI) refers to information indicating quality of a radio channel (or a link) formed between a UE and an antenna port. The CSI may include at least one of a channel quality indicator (CQI), a precoding matrix indicator (PMI), a CSI-RS resource indicator (CRI), an SSB resource indicator (SSBRI), a layer indicator (LI), a rank indicator (RI), or a reference signal received power (RSRP).

In this specification, frequency division multiplexing (FDM) may refer to transmission/reception of signals/channels/users at different frequency resources, and time division multiplexing (TDM) may refer to transmission/reception of signals/channels/users at different time resources.

In the present invention, a frequency division duplex (FDD) refers to a communication scheme in which uplink communication is performed on an uplink carrier and downlink communication is performed on a downlink carrier wave linked to the uplink carrier, and time division duplex (TDD) refers to a communication scheme in which uplink and downlink communications are performed by dividing time on the same carrier.

For background information, terms, abbreviations, etc. used in the present specification, may refer to those described in standard documents published before the present invention. For example, the following document may be referred:

3GPP LTE
3GPP TS 36.211: Physical channels and modulation
3GPP TS 36.212: Multiplexing and channel coding
3GPP TS 36.213: Physical layer procedures
3GPP TS 36.214: Physical layer; Measurements
3GPP TS 36.300: Overall description
3GPP TS 36.304: User Equipment (UE) procedures in idle mode
3GPP TS 36.314: Layer 2—Measurements
3GPP TS 36.321: Medium Access Control (MAC) protocol
3GPP TS 36.322: Radio Link Control (RLC) protocol
3GPP TS 36.323: Packet Data Convergence Protocol (PDCP)
3GPP TS 36.331: Radio Resource Control (RRC) protocol
3GPP TS 23.303: Proximity-based services (Prose); Stage 2
3GPP TS 23.285: Architecture enhancements for V2X services
3GPP TS 23.401: General Packet Radio Service (GPRS) enhancements for Evolved Universal Terrestrial Radio Access Network (E-UTRAN) access
3GPP TS 23.402: Architecture enhancements for non-3GPP accesses
3GPP TS 23.286: Application layer support for V2X services; Functional architecture and information flows
3GPP TS 24.301: Non-Access-Stratum (NAS) protocol for Evolved Packet System (EPS); Stage 3
3GPP TS 24.302: Access to the 3GPP Evolved Packet Core (EPC) via non-3GPP access networks; Stage 3
3GPP TS 24.334: Proximity-services (ProSe) User Equipment (UE) to ProSe function protocol aspects; Stage 3
3GPP TS 24.386: User Equipment (UE) to V2X control function; protocol aspects; Stage 3
3GPP NR
3GPP TS 38.211: Physical channels and modulation
3GPP TS 38.212: Multiplexing and channel coding
3GPP TS 38.213: Physical layer procedures for control
3GPP TS 38.214: Physical layer procedures for data
3GPP TS 38.215: Physical layer measurements
3GPP TS 38.300: NR and NG-RAN Overall Description
3GPP TS 38.304: User Equipment (UE) procedures in idle mode and in RRC inactive state
3GPP TS 38.321: Medium Access Control (MAC) protocol
3GPP TS 38.322: Radio Link Control (RLC) protocol
3GPP TS 38.323: Packet Data Convergence Protocol (PDCP)
3GPP TS 38.331: Radio Resource Control (RRC) protocol
3GPP TS 37.324: Service Data Adaptation Protocol (SDAP)
3GPP TS 37.340: Multi-connectivity; Overall description
3GPP TS 23.287: Application layer support for V2X services; Functional architecture and information flows
3GPP TS 23.501: System Architecture for the 5G System
3GPP TS 23.502: Procedures for the 5G System
3GPP TS 23.503: Policy and Charging Control Framework for the 5G System; Stage
3GPP TS 24.501: Non-Access-Stratum (NAS) protocol for 5G System (5GS); Stage 3
3GPP TS 24.502: Access to the 3GPP 5G Core Network (5GCN) via non-3GPP access networks
3GPP TS 24.526: User Equipment (UE) policies for 5G System (5GS); Stage 3

E. 3GPP Signal Transmission/Reception Method

Figure 8:
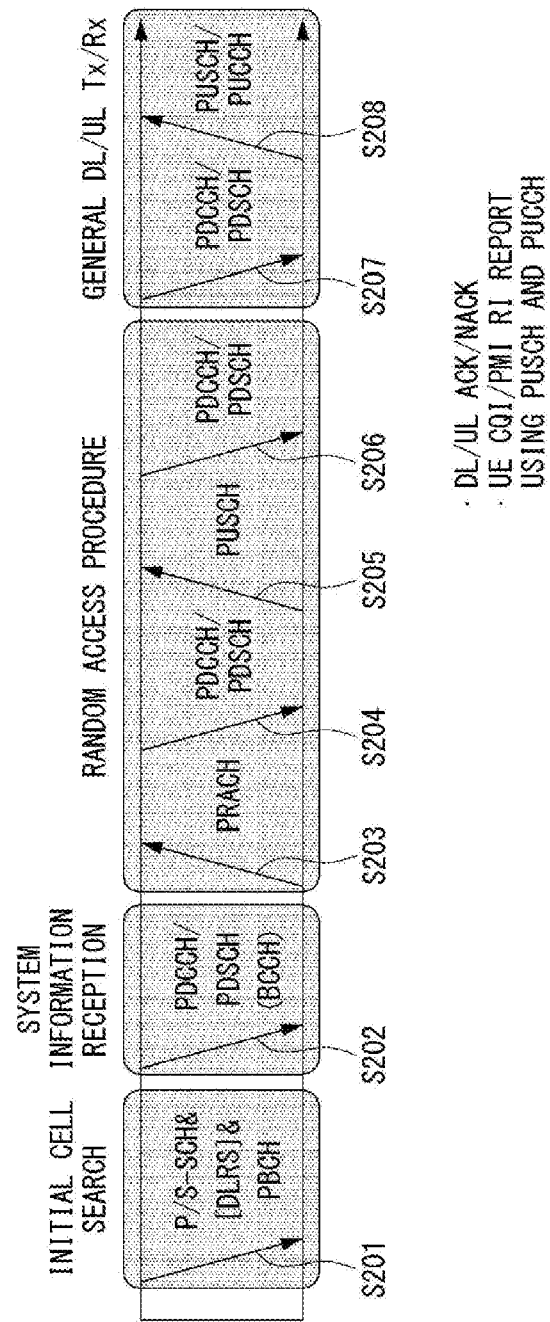
FIG. 8 is a diagram illustrating an example of a 3GPP signal transmission/reception method.

FIG. 8 is a diagram illustrating an example of a 3GPP signal transmission/reception method.

Referring to FIG. 8, when a UE is powered on or enters a new cell, the UE performs an initial cell search operation such as synchronization with a BS (S201). For this operation, the UE can receive a primary synchronization channel (P-SCH) and a secondary synchronization channel (S-SCH)

from the BS to synchronize with the BS and acquire information such as a cell ID. In LTE and NR systems, the P-SCH and S-SCH are respectively called a primary synchronization signal (PSS) and a secondary synchronization signal (SSS). The initial cell search procedure is described in detail in paragraph F. below.

After initial cell search, the UE can acquire broadcast information in the cell by receiving a physical broadcast channel (PBCH) from the BS. Further, the UE can receive a downlink reference signal (DL RS) in the initial cell search step to check a downlink channel state.

After initial cell search, the UE can acquire more detailed system information by receiving a physical downlink shared channel (PDSCH) according to a physical downlink control channel (PDCCH) and information included in the PDCCH (S202).

Meanwhile, when the UE initially accesses the BS or has no radio resource for signal transmission, the UE can perform a random access procedure (RACH) for the BS (steps S203 to S206). To this end, the UE can transmit a specific sequence as a preamble through a physical random access channel (PRACH) (S203 and S205) and receive a random access response (RAR) message for the preamble through a PDCCH and a corresponding PDSCH (S204 and S206). In the case of a contention-based RACH, a contention resolution procedure may be additionally performed. The random access procedure is described in detail in paragraph G. below.

After the UE performs the above-described process, the UE can perform PDCCH/PDSCH reception (S207) and physical uplink shared channel (PUSCH)/physical uplink control channel (PUCCH) transmission (S208) as normal uplink/downlink signal transmission processes. Particularly, the UE receives downlink control information (DCI) through the PDCCH The UE monitors a set of PDCCH candidates in monitoring occasions set for one or more control element sets (CORESET) on a serving cell according to corresponding search space configurations. A set of PDCCH candidates to be monitored by the UE is defined in terms of search space sets, and a search space set may be a common search space set or a UE-specific search space set. CORESET includes a set of (physical) resource blocks having a duration of one to three OFDM symbols. A network can configure the UE such that the UE has a plurality of CORESETs. The UE monitors PDCCH candidates in one or more search space sets. Here, monitoring means attempting decoding of PDCCH candidate(s) in a search space. When the UE has successfully decoded one of PDCCH candidates in a search space, the UE determines that a PDCCH has been detected from the PDCCH candidate and performs PDSCH reception or PUSCH transmission on the basis of DCI in the detected PDCCH.

The PDCCH can be used to schedule DL transmissions over a PDSCH and UL transmissions over a PUSCH. Here, the DCI in the PDCCH includes downlink assignment (i.e., downlink grant (DL grant)) related to a physical downlink shared channel and including at least a modulation and coding format and resource allocation information, or an uplink grant (UL grant) related to a physical uplink shared channel and including a modulation and coding format and resource allocation information.

F. Initial Access (IA) Process

Synchronization Signal Block (SSB) Transmission and Related Operation

Figure 9:
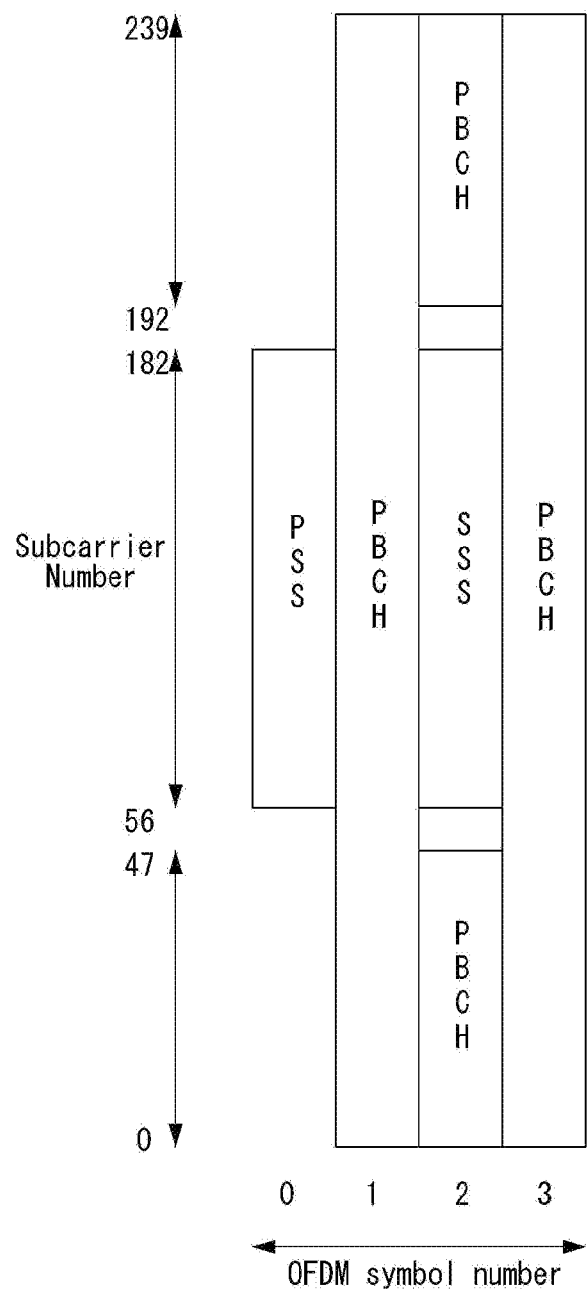
FIG. 9 illustrates an SSB structure and FIG. 10 illustrates SSB transmission.

FIG. 9 illustrates an SSB structure. The UE can perform cell search, system information acquisition, beam alignment for initial access, and DL measurement on the basis of an SSB. The SSB is interchangeably used with a synchronization signal/physical broadcast channel (SS/PBCH) bloc.

Referring to FIG. 9, the SSB includes a PSS, an SSS and a PBCH. The SSB is configured in four consecutive OFDM symbols, and a PSS, a PBCH, an SSS/PBCH or a PBCH is transmitted for each OFDM symbol. Each of the PSS and the SSS includes one OFDM symbol and 127 subcarriers, and the PBCH includes 3 OFDM symbols and 576 subcarriers. The PBCH is encoded/decoded on the basis of a polar code and modulated/demodulated according to quadrature phase shift keying (QPSK). The PBCH in the OFDM symbol includes data resource elements (REs) to which a complex modulation value of a PBCH is mapped and DMRS REs to which a demodulation reference signal (DMRS) for the PBCH is mapped. There are three DMRS REs per resource block of the OFDM symbol, and there are three data REs between the DMRS REs.

Cell Search

Cell search refers to a process in which a UE acquires time/frequency synchronization of a cell and detects a cell identifier (ID) (e.g., physical layer cell ID (PCI)) of the cell. The PSS is used to detect a cell ID in a cell ID group and the SSS is used to detect a cell ID group. The PBCH is used to detect an SSB (time) index and a half-frame.

The cell search procedure of the UE may be summarized as shown in Table 1 below.

TABLE 1

| | Type of Signals | Operations |
|---|---|---|
| 1st step | PSS | SS/PBCH block (SSB) symbol timing acquisition Cell ID detection within a cell ID group(3 hypothesis) |
| 2nd Step | SSS | Cell ID group detection (336 hypothesis) |
| 3rd Step | PBCH DMRS | SSB index and Half frame (HF) index (Slot and frame boundary detection) |
| 4th Step | PBCH | Time information (80 ms, System Frame Number (SFN), SSB index, HF) Remaining Minimum System Information (RMSI) Control resource set (CORESET)/Search space configuration |
| 5th Step | PDCCH and PDSCH | Cell access information RACH configuration |

There are 336 cell ID groups and there are 3 cell IDs per cell ID group. A total of 1008 cell IDs are present. Information on a cell ID group to which a cell ID of a cell belongs is provided/acquired through an SSS of the cell, and information on the cell ID among 336 cell ID groups is provided/acquired through a PSS.

Figure 10:
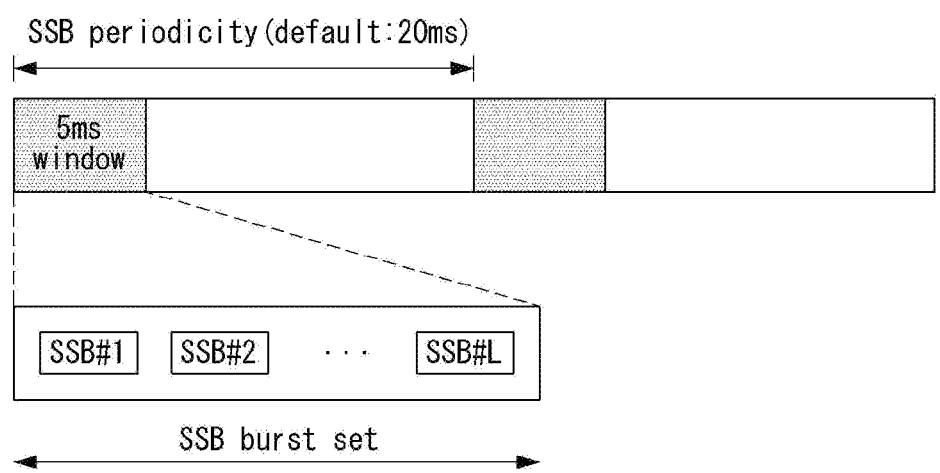

FIG. 10 illustrates SSB transmission.

The SSB is periodically transmitted in accordance with SSB periodicity. A default SSB periodicity assumed by a UE during initial cell search is defined as 20 ms. After cell access, the SSB periodicity can be set to one of {5 ms, 10 ms, 20 ms, 40 ms, 80 ms, 160 ms} by a network (e.g., a BS). An SSB burst set is configured at a start portion of the SSB period. The SSB burst set includes a 5 ms time window (i.e., half-frame), and the SSB may be transmitted up to N times within the SS burst set. The maximum transmission number L of the SSB may be given as follows according to a frequency band of a carrier wave. One slot includes a maximum of two SSBs.

For frequency range up to 3 GHz, L=4
For frequency range from 3 GHz to 6 GHz, L=8
For frequency range from 6 GHz to 52.6 GHz, L=64

A time position of an SSB candidate in the SS burst set may be defined according to a subscriber spacing. The SSB candidate time position is indexed from 0 to L−1 (SSB index) in time order within the SSB burst set (i.e., half-frame).

A plurality of SSBs may be transmitted within a frequency span of a carrier wave. Physical layer cell identifiers of these SSBs need not be unique, and other SSBs may have different physical layer cell identifiers.

The UE may acquire the DL synchronization by detecting the SSB. The UE may identify a structure of the SSB burst set on the basis of the detected SSB (time) index and thus detect a symbol/slot/half-frame boundary. The number of the frame/half-frame to which the detected SSB belongs may be identified using system frame number (SFN) information and half-frame indication information.

Specifically, the UE may acquire a 10-bit SFN for a frame to which the PBCH belongs from the PBCH. Next, the UE may acquire 1-bit half-frame indication information. For example, if the UE detects a PBCH with a half-frame indication bit set to 0, it may determine that the SSB, to which the PBCH belongs, belongs to a first half-frame in the frame, and if the UE detects a PBCH with a half-frame indication bit set to 1, it may determine that the SSB, to which the PBCH belongs, belongs to a second half-frame in the frame. Finally, the UE may acquire an SSB index of the SSB to which the PBCH belongs on the basis of a DMRS sequence and PBCH payload carried by the PBCH.

Acquisition of System Information (SI)

SI is divided into a master information block (MIB) and a plurality of system information blocks (SIBs). The SI other than the MIB may be referred to as remaining minimum system information (RMSI). Details thereof may be referred to the following:

The MIB includes information/parameters for monitoring the PDCCH scheduling PDSCH carrying system information block1 (SIB1) and is transmitted by the BS through the PBCH of the SSB. For example, the UE may check whether a control resource set (CORESET) exists for the Type 0-PDCCH common search space on the basis of the MIB. The Type 0-PDCCH common search space is a kind of PDCCH search space and is used to transmit a PDCCH for scheduling an SI message. If the Type 0-PDCCH common search space is present, the UE may determine (i) a plurality of contiguous resource blocks and one or more consecutive resource blocks constituting a CORESET on the basis of information in the MIB (e.g., pdcch-ConfigSIB1) and (ii) a PDCCH occasion (e.g., time domain position for PDCCH reception). If no Type 0-PDCCH common search space exists, pdcch-ConfigSIB1 provides information on a frequency location where SSB/SIB1 exists and information on a frequency range where SSB/SIB1 does not exist.

SIB1 includes information related to availability and scheduling (e.g., transmission periodicity and SI-window size) of the remaining SIBs (hereinafter, SIBx, x is an integer equal to or greater than 2). For example, SIB1 may indicate whether the SIBx is periodically broadcast or provided according to a request from the UE on an on-demand basis. If SIBx is provided on the on-demand basis, SIB1 may include information necessary for the UE to perform the SI request. The SIB1 is transmitted through the PDSCH, the PDCCH for scheduling the SIB1 is transmitted through the Type 0-PDCCH common search space, and the SIB1 is transmitted through the PDSCH indicated by the PDCCH.

The SIBx is included in the SI message and transmitted via the PDSCH. Each SI message is transmitted within a time window (i.e., SI-window) that occurs periodically.

G. Random Access Procedure

Figure 11:
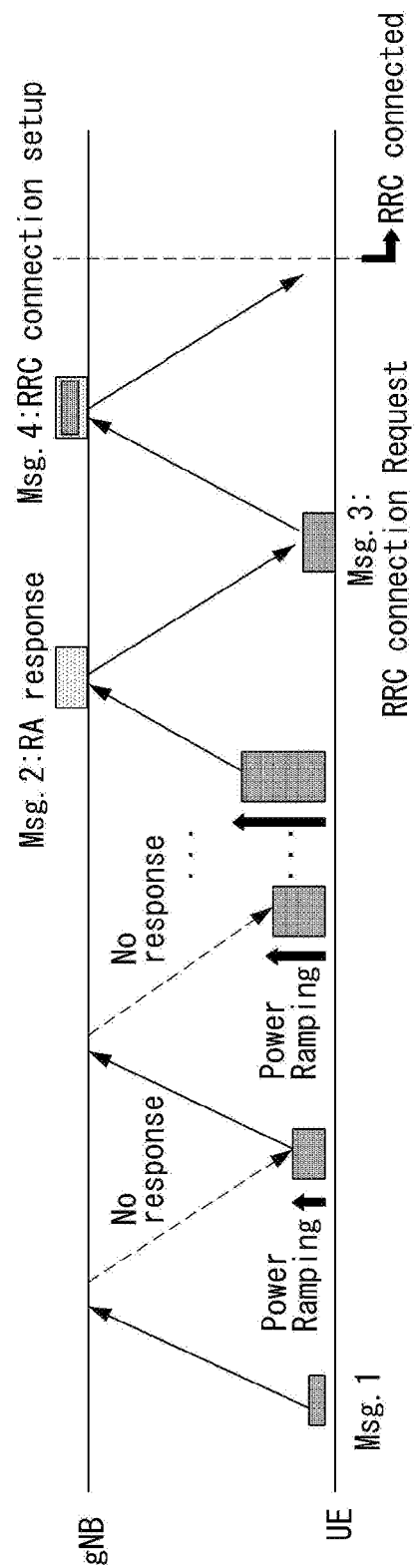
FIG. 11 illustrates an example of a random access procedure.

The random access procedure of the UE may be summarized as shown in Table 2 and FIG. 11.

TABLE 2

| | Signal type | Acquired operation/information |
|---|---|---|
| First step | PRACH preamble in UL | Acquire initial beam Random selection of random access preamble ID |
| Second step | Random access response on PDSCH | Timing advance information Random access preamble ID Initial UL grant, temporary C-RNTI |
| Third step | UL transmission on PUSCH | RRC connection request UE identifier |
| Fourth step | Contention resolution on DL | Temporary C-RNTI on PDCCH for initial access C-RNTI on PDCCH for RRC_CONNECTED UE |

The random access procedure is used for various purposes. For example, the random access procedure can be used for network initial access, handover, and UE-triggered UL data transmission. A UE can acquire UL synchronization and UL transmission resources through the random access procedure. The random access procedure is classified into a contention-based random access procedure and a contention-free random access procedure.

FIG. 11 illustrates an example of a random access procedure. In particular, FIG. 11 illustrates a contention-based random access procedure.

First, a UE can transmit a random access preamble through a PRACH as Msg1 of a random access procedure in UL.

Random access preamble sequences having different two lengths are supported. A long sequence length 839 is applied to subcarrier spacings of 1.25 kHz and 5 kHz and a short sequence length 139 is applied to subcarrier spacings of 15 kHz, 30 kHz, 60 kHz and 120 kHz.

Multiple preamble formats are defined by one or more RACH OFDM symbols and different cyclic prefixes (and/or guard time). RACH configuration for a cell is included in the system information of the cell and is provided to the UE. The RACH configuration includes information on a subcarrier spacing of the PRACH, available preambles, preamble format, and the like. The RACH configuration includes association information between SSBs and RACH (time-frequency) resources. The UE transmits a random access preamble in the RACH time-frequency resource associated with the detected or selected SSB.

A threshold value of the SSB for the RACH resource association may be set by the network, and RACH preamble is transmitted or retransmitted on the basis of the SSB in which reference signal received power (RSRP) measured on the basis of the SSB satisfies the threshold value. For example, the UE may select one of the SSB (s) satisfying the threshold value and may transmit or retransmit the RACH preamble on the basis of the RACH resource associated with the selected SSB.

When a BS receives the random access preamble from the UE, the BS transmits a random access response (RAR) message (Msg2) to the UE. A PDCCH that schedules a PDSCH carrying a RAR is CRC masked by a random access (RA) radio network temporary identifier (RNTI) (RA-RNTI) and transmitted. Upon detection of the PDCCH masked by the RA-RNTI, the UE can receive a RAR from the PDSCH scheduled by DCI carried by the PDCCH. The UE checks whether the RAR includes random access response information with respect to the preamble transmitted by the UE, that is, Msg1. Presence or absence of random access information with respect to Msg1 transmitted by the UE can be determined according to presence or absence of a random access preamble ID with respect to the preamble transmitted by the UE. If there is no response to Msg1, the UE can retransmit the RACH preamble less than a predetermined number of times while performing power ramping. The UE calculates PRACH transmission power for preamble retransmission on the basis of most recent pathloss and a power ramping counter.

When the random access response information includes timing advance information for UL synchronization and an UL grant, and when a temporary UE receives a random response information regarding the UE itself on the PDSCH, the UE may know timing advance information for UL synchronization, an initial UL grant, and a UE temporary cell RNTI (cell RNTI, C-RNTI). The timing advance information is used to control uplink signal transmission timing. In order to ensure that the PUSCH/PUCCH transmission by the UE is better aligned with the subframe timing at a network end, the network (e.g. BS) may measure a time difference between the PUSCH/PUCCH/SRS reception and subframes and send timing advance information on the basis of the time difference. The UE can perform UL transmission through Msg3 of the random access procedure over a physical uplink shared channel on the basis of the random access response information. Msg3 can include an RRC connection request and a UE ID. The network can transmit Msg4 as a response to Msg3, and Msg4 can be handled as a contention resolution message on DL. The UE can enter an RRC connected state by receiving Msg4.

Meanwhile, the contention-free random access procedure may be performed when the UE performs handover to another cell or BS or when the contention-free random access procedure is requested by a BS command. A basic process of the contention-free random access procedure is similar to the contention-based random access procedure. However, unlike the contention-based random access procedure in which the UE randomly selects a preamble to be used among a plurality of random access preambles, in the case of the contention-free random access procedure, a preamble (hereinafter referred to as a dedicated random access preamble) to be used by the UE is allocated by the BS to the UE. Information on the dedicated random access preamble may be included in an RRC message (e.g., a handover command) or may be provided to the UE via a PDCCH order. When the random access procedure is started, the UE transmits a dedicated random access preamble to the BS. When the UE receives the random access procedure from the BS, the random access procedure is completed.

As mentioned above, the UL grant in the RAR schedules PUSCH transmission to the UE. The PUSCH carrying initial UL transmission based on the UL grant in the RAR will be referred to as Msg3 PUSCH. The content of the RAR UL grant starts at an MSB and ends at a LSB and is given in Table 3.

TABLE 3

| RAR UL grant field | Number of bits |
|---|---|
| Frequency hopping flag | 1 |
| Msg3 PUSCH frequency resource allocation | 12 |
| Msg3 PUSCH time resource allocation | 4 |
| Modulation and coding scheme (MCS) | 4 |
| Transmit power control (TPC) for Msg3 PUSCH | 3 |
| CSI request | 1 |

The TPC command is used to determine transmission power of the Msg3 PUSCH and is interpreted, for example, according to Table 4.

TABLE 4

| TPC command | value [dB] |
|---|---|
| 0 | −6 |
| 1 | −4 |
| 2 | −2 |
| 3 | 0 |
| 4 | 2 |
| 5 | 4 |
| 6 | 6 |
| 7 | 8 |

In the contention-free random access procedure, the CSI request field in the RAR UL grant indicates whether the UE includes an aperiodic CSI report in the corresponding PUSCH transmission. A subcarrier spacing for the Msg3 PUSCH transmission is provided by an RRC parameter. The UE will transmit the PRACH and Msg3 PUSCH on the same uplink carrier of the same service providing cell. A UL BWP for Msg3 PUSCH transmission is indicated by SIB1 (SystemInformationBlock1).

H. DL and UL Transmitting/Receiving Operations

DL Transmitting/Receiving Operation

A downlink grant (also referred to as a downlink assignment) may be divided into (1) dynamic grant and (2) configured grant. The dynamic grant, which is intended to maximize resource utilization, refers to a method of data transmission/reception on the basis of dynamic scheduling by the BS.

The BS schedules downlink transmission through a DCI. The UE receives on the PDCCH the DCI for downlink scheduling (i.e., including scheduling information of the PDSCH) from the BS. DCI format 1_0 or 1_1 may be used for downlink scheduling. The DCI format 1_1 for downlink scheduling may include, for example, the following information: an identifier for DCI format, a bandwidth part indicator, a frequency domain resource assignment, time domain resource assignment, MCS.

The UE may determine a modulation order, a target code rate, and a transport block size for the PDSCH on the basis of the MCS field in the DCI. The UE may receive the PDSCH in time-frequency resource according to frequency domain resource allocation information and time domain resource allocation information.

The DL grant is also referred to as semi-persistent scheduling (SPS). The UE may receive an RRC message including a resource configuration for transmission of DL data from the BS. In the case of the DL SPS, an actual DL configured grant is provided by the PDCCH and is activated or deactivated by the PDCCH. If the DL SPS is configured, at least the following parameters are provided to the UE via RRC signaling from the BS: a configured scheduling RNTI (CS-RNTI) for activation, deactivation and retransmission; and cycle. The actual DL grant of the DL SPS is provided to the UE by the DCI in the PDCCH addressed to the CS-RNTI. The UE activates an SPS associated with the CS-RNTI if specific fields of the DCI in the PDCCH addressed to the CS-RNTI are set to specific values for scheduling activation. The UE may receive downlink data through the PDSCH on the basis of the SPS.

UL Transmitting/Receiving Operation

The BS transmits a DCI including uplink scheduling information to the UE. The UE receives on the PDCCH the DCI for uplink scheduling (i.e., including scheduling information of the PUSCH) from the BS. DCI format 0_0 or 0_1 may be used for uplink scheduling. The DCI format 0_1 for uplink scheduling may include the following information: an identifier for DCI format, a bandwidth part indicator, a frequency domain resource assignment, a time domain resource assignment, MCS.

The UE transmits uplink data on the PUSCH on the basis of the DCI. For example, when the UE detects the PDCCH including the DCI format 0_0 or 0_1, the UE transmits the PUSCH according to an instruction based on the DCI. Two transmission schemes are supported for PUSCH transmission: codebook-based transmission and non-codebook-based transmission.

When an RRC parameter 'txConfig' receives an RRC message set to 'codebook', the UE is configured to a codebook-based transmission. Meanwhile, when an RRC message in which the RRC parameter 'txConfig' is set to 'nonCodebook' is received, the UE is configured to a non-codebook-based transmission. The PUSCH may be semi-statically scheduled by the DCI format 0_0, by the DCI format 0_1, or by RRC signaling.

The uplink grant may be divided into (1) a dynamic grant and (2) a configured grant.

Figure 12A:
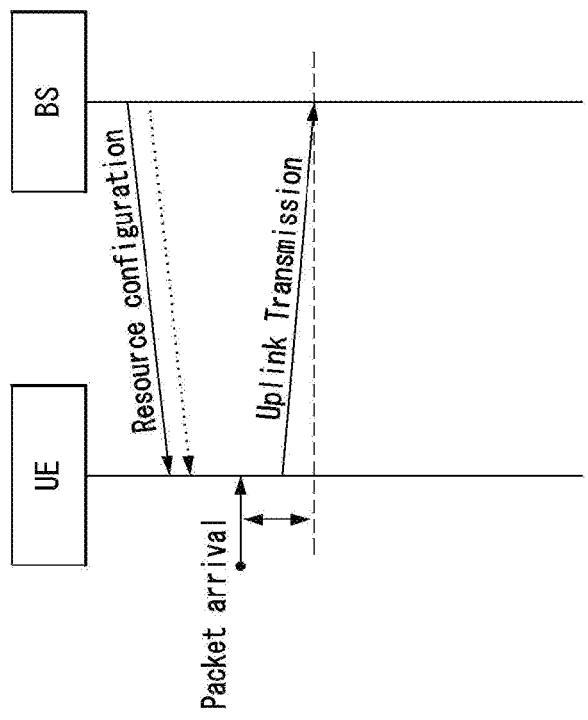
FIGS. 12A and 12B show examples of an uplink grant.
Figure 12B:
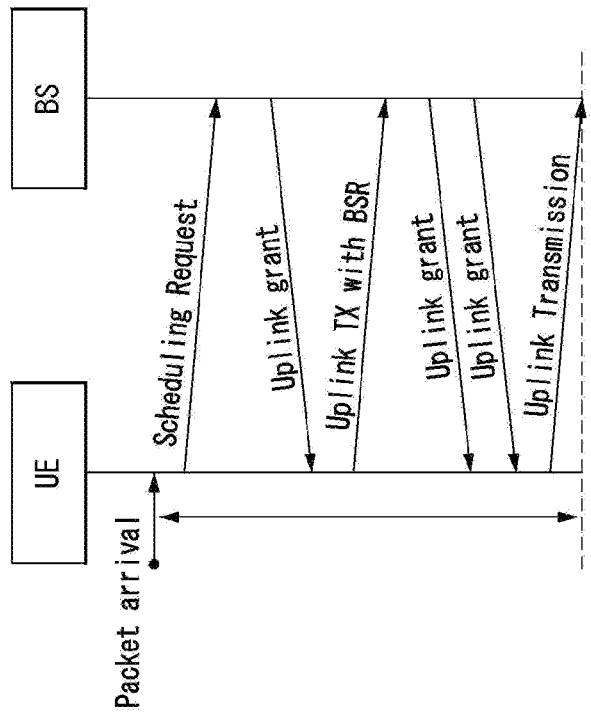

FIGS. 12A and 12B show examples of an uplink grant. FIG. 12A illustrates an UL transmission process based on the dynamic grant, and FIG. 12B illustrates an UL transmission process based on the configured grant.

A dynamic grant, which is to maximize utilization of resources, refers to a data transmission/reception method based on dynamic scheduling by a BS. This means that when the UE has data to be transmitted, the UE requests uplink resource allocation from the BS and transmits the data using only uplink resource allocated by the BS. In order to use the uplink radio resource efficiently, the BS must know how much data each UE transmits on the uplink. Therefore, the UE may directly transmit information on uplink data to be transmitted to the BS, and the BS may allocate uplink resources to the UE on the basis of the information. In this case, the information on the uplink data transmitted from the UE to the BS is referred to as a buffer status report (BSR), and the BSR relates to the amount of uplink data stored in a buffer of the UE.

Referring to FIG. 12A, an uplink resource allocation process for actual data when the UE does not have an uplink radio resource available for transmission of the BSR is illustrated. For example, since the UE which does not have a UL grant cannot available for UL data transmission cannot transmit the BSR through a PUSCH, the UE must request resource for uplink data must by starting transmission of a scheduling request via a PUCCH, and in this case, an uplink resource allocation process of five steps is used.

Referring to FIG. 12A, if there is no PUSCH resource for transmitting a BSR, the UE first transmits a scheduling request (SR) to the BS in order to be allocated a PUSCH resource. The SR is used by the UE to request the BS for PUSCH resources for uplink transmission when a reporting event occurs but there is no PUSCH resource available to the UE. Depending on whether there is a valid PUCCH resource for the SR, the UE transmits the SR via the PUCCH or initiates a random access procedure. When the UE receives the UL grant from the BS, it transmits the BSR to the BS via the PUSCH resource allocated by the UL grant. The BS checks the amount of data to be transmitted by the UE on the uplink on the basis of the BSR and transmits a UL grant to the UE. The UE receiving the UL grant transmits actual uplink data to the BS through the PUSCH on the basis of the UL grant.

Referring to FIG. 12B, the UE receives an RRC message including a resource configuration for transmission of UL data from the BS. There are two types of UL-configured grants in the NR system: Type 1 and Type 2. In the case of UL-configured grant type 1, an actual UL grant (e.g., time resource, frequency resource) is provided by RRC signaling, and in the case of Type 2, an actual UL grant is provided by the PDCCH and is activated or deactivated by the PDCCH. If the grant type 1 is configured, at least the following parameters are provided to the UE via RRC signaling from the BS: CS-RNTI for retransmission; periodicity of the configured grant type 1; information about a start symbol index S and a symbol length L for an intra-slot PUSCH; time domain offset representing an offset of the resource for SFN=0 in the time domain; MCS index indicating modulation order, target code rate, and transport block size. If the grant type 2 is configured, at least the following parameters are provided to the UE via RRC signaling from the BS: CS-RNTI for activation, deactivation and retransmission; periodicity of configured grant type 2. The actual UL grant of the configured grant type 2 is provided to the UE by the DCI in the PDCCH addressed to the CS-RNTI. If the specific fields of the DCI in the PDCCH addressed to the CS-RNTI are set to a specific value for scheduling activation, the UE activates the configured grant type 2 associated with the CS-RNTI.

The UE may perform uplink transmission via the PUSCH on the basis of the configured grant according to the type 1 or type 2.

Resources for initial transmission by the configured grant may or may not be shared by one or more UEs.

Figure 13:
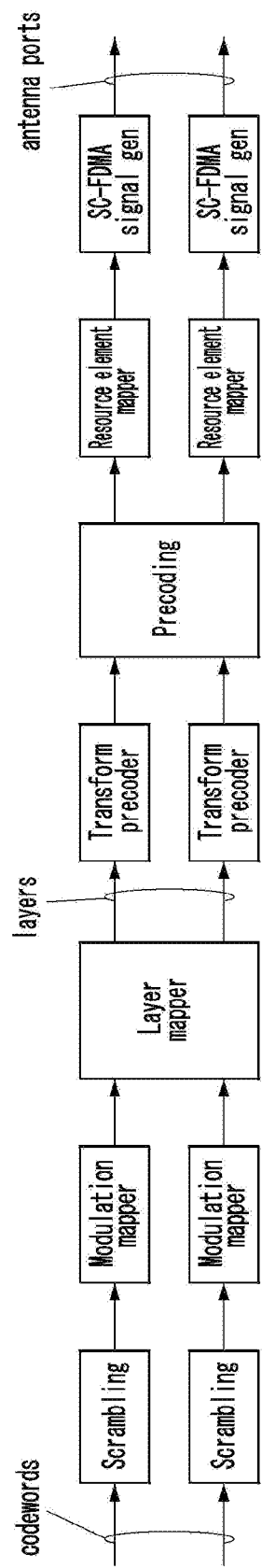
FIG. 13 shows an example of a conceptual diagram of uplink physical channel processing.

FIG. 13 shows an example of a conceptual diagram of uplink physical channel processing.

Each of the blocks shown in FIG. 13 may be performed in each module in the physical layer block of a transmission device. More specifically, the uplink signal processing in FIG. 13 may be performed in the processor of the UE/BS described in this specification. Referring to FIG. 13, the uplink physical channel processing may be performed through scrambling, modulation mapping, layer mapping, transform precoding, precoding, resource element mapping, and SC-FDMA signal generation (SC-FDMA signal generation). Each of the above processes may be performed separately or together in each module of the transmission device. The transform precoding is spreading UL data in a special way to reduce a peak-to-average power ratio (PAPR) of a waveform, and is a kind of discrete Fourier transform (DFT). OFDM using a CP together with the transform precoding that performs DFT spreading is called DFT-s-

OFDM, and OFDM using a CP without DFT spreading is called CP-OFDM. Transform precoding may optionally be applied if it is enabled for the UL in an NR system. That is, the NR system supports two options for UL waveforms, one of which is CP-OFDM and the other is DFT-s-OFDM. Whether the UE must use the CP-OFDM as a UL transmit waveform or the DFT-s-OFDM as a UL transmit waveform is provided from the BS to the UE via RRC parameters. FIG. 13 is a conceptual diagram of uplink physical channel processing for DFT-s-OFDM. In the case of CP-OFDM, the transform precoding among the processes of FIG. 13 is omitted.

More specifically, the transmission device scrambles coded bits in a codeword by a scrambling module, and then transmits the coded bits through a physical channel. Here, the codeword is acquired by encoding a transport block. The scrambled bits are modulated by a modulation mapping module into complex-valued modulation symbols. The modulation mapping module may modulate the scrambled bits according to a predetermined modulation scheme and arrange the modulated bits as complex-valued modulation symbols representing a position on a signal constellation. pi/2-BPSK (pi/2-Binary Phase Shift Keying), m-PSK (m-Phase Shift Keying) or m-QAM (m-Quadrature Amplitude Modulation) may be used for modulating the coded data. The complex-valued modulation symbols may be mapped to one or more transport layers by a layer mapping module. The complex-valued modulation symbols on each layer may be precoded by a precoding module for transmission on an antenna port. If the transform precoding is enabled, the precoding module may perform precoding after performing transform precoding on the complex-valued modulation symbols as shown in FIG. 13. The precoding module may process the complex-valued modulation symbols in a MIMO manner according to multiple transmission antennas to output antenna-specific symbols, and distribute the antenna-specific symbols to a corresponding resource element mapping module. An output z of the precoding module may be acquired by multiplying an output y of the layer mapping module by a precoding matrix W of N×M. Here, N is the number of antenna ports and M is the number of layers. The resource element mapping module maps the complex-valued modulation symbols for each antenna port to an appropriate resource element in the resource block allocated for transmission. The resource element mapping module may map the complex-valued modulation symbols to appropriate subcarriers and multiplex the same according to users. The SC-FDMA signal generation module (CP-OFDM signal generation module if the transform precoding is disabled) modulates the complex-valued modulation symbol according to a specific modulation scheme, for example, an OFDM scheme, to generate a complex-valued time domain OFDM (Orthogonal Frequency Division Multiplexing) symbol signal. The signal generation module may perform Inverse Fast Fourier Transform (IFFT) on the antenna specific symbol, and a CP may be inserted into the time domain symbol on which the IFFT has been performed. The OFDM symbol undergoes digital-to-analog conversion, upconverting, and the like, and transmitted to a reception device through each transmission antenna. The signal generation module may include an IFFT module and a CP inserter, a digital-to-analog converter (DAC), and a frequency uplink converter.

A signal processing procedure of a reception device may be the reverse of the signal processing procedure of the transmission device. Details thereof may be referred to the above contents and FIG. 13.

Next, the PUCCH will be described.

The PUCCH supports a plurality of formats, and the PUCCH formats may be classified according to symbol duration, payload size, multiplexing, and the like. Table 5 below illustrates PUCCH formats.

TABLE 5

| Format | PUCCH length in OFDM symbols | Number of bits | Usage | Etc. |
|---|---|---|---|---|
| 0 | 1-2 | ≤2 | 1 | Sequence selection |
| 1 | 4-14 | ≤2 | 2 | Sequence modulation |
| 2 | 1-2 | >2 | 4 | CP-OFDM |
| 3 | 4-14 | >2 | 8 | DFT-s-OFDM(no UE multiplexing) |
| 4 | 4-14 | >2 | 16 | DFT-s-OFDM(Pre DFT orthogonal cover code(OCC)) |

The PUCCH formats shown in Table 5 may be divided into (1) a short PUCCH and (2) a long PUCCH. PUCCH formats 0 and 2 may be included in the short PUCCH, and PUCCH formats 1, 3 and 4 may be included in the long PUCCH.

Figure 14:
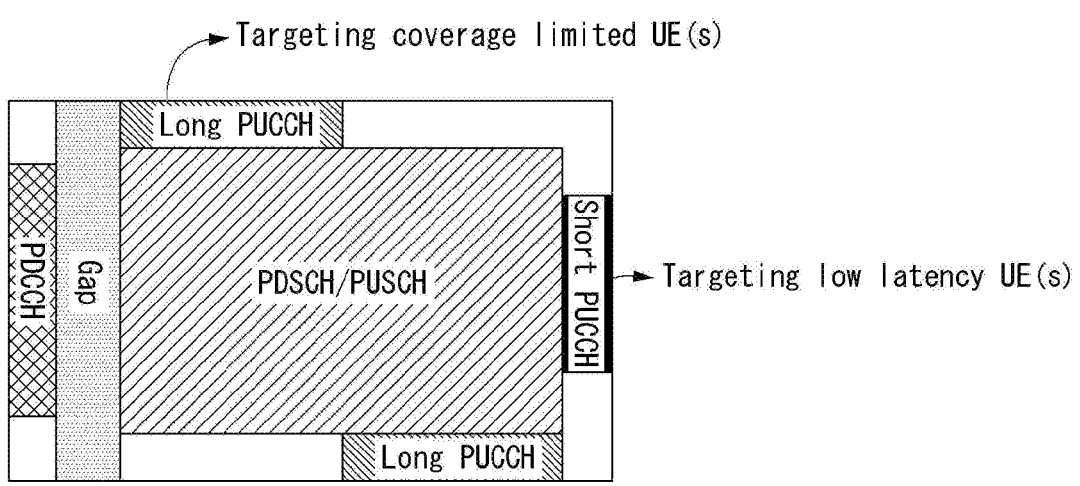
FIG. 14 shows an example of an NR slot in which a PUCCH is transmitted.

FIG. 14 shows an example of an NR slot in which a PUCCH is transmitted.

The UE transmits one or two PUCCHs through serving cells in different symbols in one slot. When the UE transmits two PUCCHs in one slot, at least one of the two PUCCHs has a structure of the short PUCCH.

I. eMBB (Enhanced Mobile Broadband Communication)

In the case of the NR system, a massive multiple input multiple output (MIMO) environment in which the transmit/receive antennas are significantly increased may be considered. That is, as the large MIMO environment is considered, the number of transmit/receive antennas may increase to several tens or hundreds or more. Meanwhile, the NR system supports communication in above 6 GHz band, that is, the millimeter frequency band. However, the millimeter frequency band has a frequency characteristic in which signal attenuation according to a distance is very sharp due to the use of a frequency band which is too high. Therefore, an NR system using the band of 6 GHz or higher uses a beamforming technique in which energy is collected and transmitted in a specific direction, not in all directions, in order to compensate for sudden propagation attenuation characteristics. In the massive MIMO environment, a hybrid type beamforming technique combining an analog beamforming technique and a digital beamforming technique is required depending on a position to which a beamforming weight vector/precoding vector is applied, to reduce complexity of hardware implementation, increase performance using multiple antennas, obtain flexibility of resource allocation, and facilitate beam control for each frequency.

Hybrid Beamforming

Figure 15:
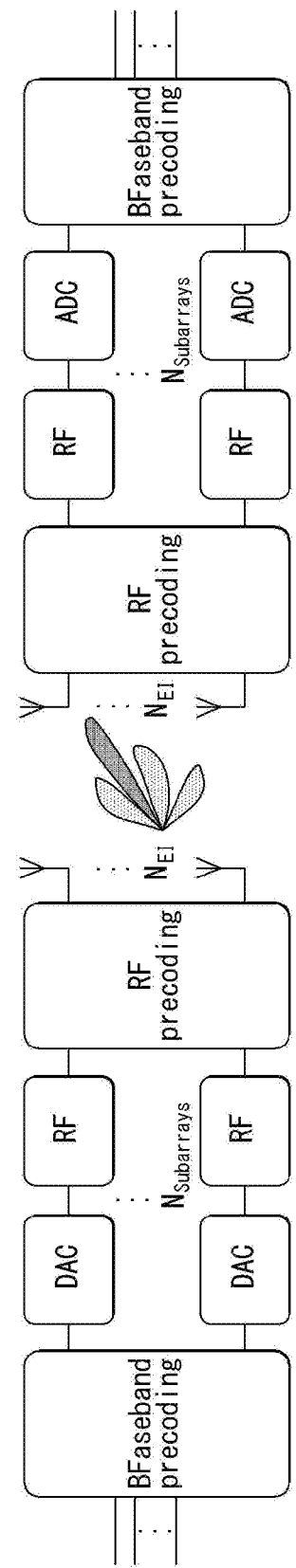
FIG. 15 is a block diagram of a transmitter and a receiver for hybrid beamforming

FIG. 15 illustrates an example of a block diagram of a transmitter and a receiver for hybrid beamforming.

As a method for forming a narrow beam in a millimeter frequency band, a beam forming scheme in which energy is increased only in a specific direction by transmitting the same signal using a phase difference suitable for a large number of antennas in a BS or a UE is mainly considered. Such beamforming scheme includes digital beamforming to create a phase difference in a digital baseband signal, analog beamforming to create a phase difference in a modulated analog signal using time delay (i.e., cyclic shift), and hybrid beamforming using both digital beamforming and analog beamforming, or the like. If each antenna element has an RF unit (or transceiver unit (TXRU)) to adjust transmission power and phase, independent beamforming is possible for each frequency resource. However, it is not effective in terms of price to install an RF unit in all 100 antenna elements. That is, since the millimeter frequency band requires a large number of antennas to compensate for the sudden attenuation characteristics and digital beamforming requires an RF component (e.g., a digital-to-analog converter (DAC), a mixer, a power amplifier, a linear amplifier, and the like), implementation of digital beamforming in the millimeter frequency band causes the price of the communication device to increase. Therefore, when a large number of antennas are required such as in the millimeter frequency band, the use of analog beamforming or hybrid beamforming is considered. In the analog beamforming scheme, a plurality of antenna elements are mapped to one TXRU and a direction of a beam is adjusted by an analog phase shifter. Such an analog beamforming scheme may generate only one beam direction in the entire band, and thus, it cannot perform frequency selective beamforming (BF). Hybrid BF is an intermediate form of digital BF and analog BF and has B RF units fewer than Q antenna elements. In the case of the hybrid BF, directions of beams that may be transmitted at the same time is limited to B or less, although there is a difference depending on a method of connecting the B RF units and Q antenna elements.

Beam Management (BM)

The BM process includes processes for acquiring and maintaining a set of BS (or a transmission and reception point (TRP)) and/or UE beams that may be used for downlink (DL) and uplink (UL) transmission/reception and may include the following processes and terms.

beam measurement: operation for BS or UE to measure characteristic of received beamforming signal.

beam determination: operation for BS or UE to select its own Tx beam/Rx beam.

beam sweeping: an operation to cover spatial domain using transmission and/or reception beam during a predetermined time interval in a predetermined manner.

beam report: an operation for UE to report information of beamformed signal on the basis of beam measurement.

The BM process may be classified into (1) DL BM process using SSB or CSI-RS and (2) UL BM process using SRS (sounding reference signal). Also, each BM process may include Tx beam sweeping to determine Tx beam and Rx beam sweeping to determine Rx beam.

DL BM Process

The DL BM process may include (1) transmission of beamformed DL RSs (e.g., CSI-RS or SSB) by the BS, and (2) beam reporting by the UE.

Here, the beam report may include a preferred DL RS ID(s) and a corresponding reference signal received power (RSRP). The DL RS ID may be an SSBRI (SSB Resource Indicator) or a CRI (CSI-RS Resource Indicator).

Figure 16:
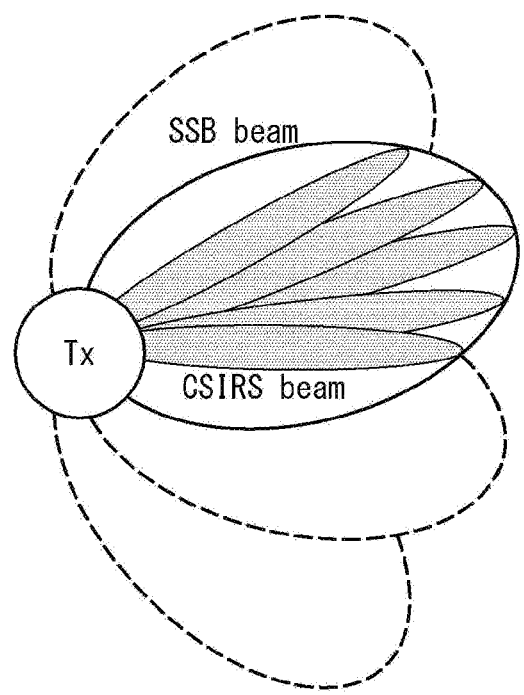
FIG. 16 shows an example of beamforming using an SSB and a CSI-RS.

FIG. 16 shows an example of beamforming using SSB and CSI-RS.

As shown in FIG. 16, the SSB beam and the CSI-RS beam may be used for beam measurement. The measurement metric is an RSRP per resource/block. The SSB may be used for coarse beam measurement, and the CSI-RS may be used for fine beam measurement. SSB may be used for both Tx beam sweeping and Rx beam sweeping. Rx beam sweeping using the SSB may be performed by attempting to receive the SSB while the UE changes the Rx beam for the same SSBRI across multiple SSB bursts. Here, one SS burst may include one or more SSBs, and one SS burst set includes one or more SSB bursts.

1. DL BM Using SSB

Figure 17:
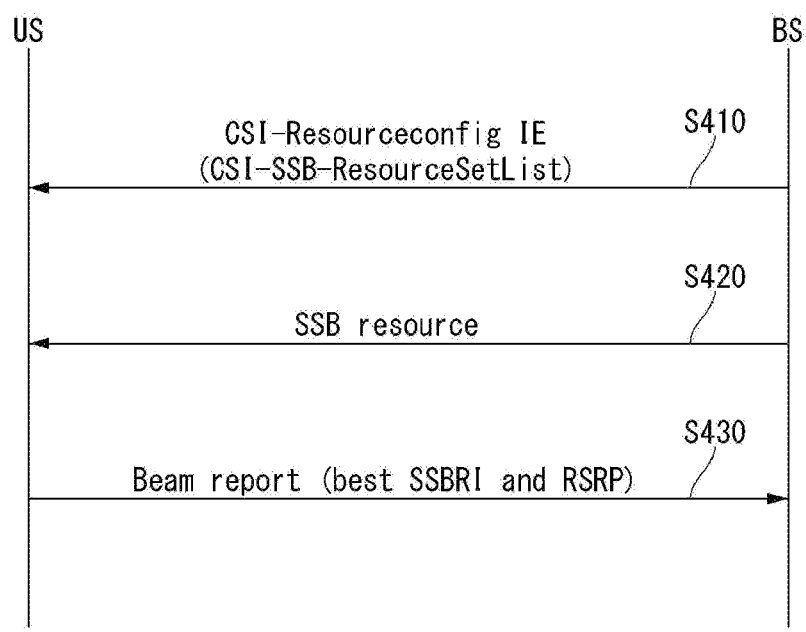
FIG. 17 is a flowchart illustrating an example of a DL BM process using an SSB.

FIG. 17 is a flowchart illustrating an example of a DL BM process using SSB.

A configuration for beam report using the SSB is performed at the time of channel state information (CSI)/beam configuration in RRC_CONNECTED.

The UE receives from the BS a CSI-ResourceConfig IE including a CSI-SSB-ResourceSetList for the SSB resources used for the BM (S410). The RRC parameter csi-SSB-ResourceSetList represents a list of SSB resources used for beam management and reporting in one resource set. Here, the SSB resource set may be configured to {SSBx1, SSBx2, SSBx3, SSBx4}. The SSB index may be defined from 0 to 63.

The UE receives signals on the SSB resources from the BS on the basis of the CSI-SSB-ResourceSetList (S420).

If the CSI-RS reportConfig associated with reporting on the SSBRI and reference signal received power (RSRP) is configured, the UE reports the best SSBRI and its corresponding RSRP to the BS S430). For example, if the reportQuantity of the CSI-RS reportConfig IE is set to 'ssb-Index-RSRP', the UE reports the best SSBRI and a corresponding RSRP to the BS.

When the CSI-RS resource is configured in the same OFDM symbol (s) as the SSB and 'QCL-Type D' is applicable, the UE may assume that the CSI-RS and the SSB are quasi co-located (QCL-ed) in terms of 'QCL-TypeD'. Here, QCL-TypeD may refer to QCL-ed between antenna ports in terms of spatial Rx parameter. The same receive beam may be applied when the UE receives signals of a plurality of DL antenna ports in the QCL-TypeD relationship. Details of QCL may refer to a section 4. QCL below.

2. DL BM Using CSI-RS

Referring to the use of CSI-RS, i) if a repetition parameter is set for a specific CSI-RS resource set and TRS_info is not configured, CSI-RS is used for beam management. ii) If the repetition parameter is not set and TRS_info is set, the CSI-RS is used for a tracking reference signal (TRS). Iii) If the repetition parameter is not set and TRS_info is not set, the CSI-RS is used for CSI acquisition.

(RRC Parameter) If the repetition is set to 'ON', it relates to a Rx beam sweeping process of the UE. If the repetition is set to 'ON', the UE may assume that if NZP-CSI-RS-ResourceSet is configured, signals of at least one CSI-RS resource in the NZP-CSI-RS-ResourceSet are transmitted in the same downlink space domain filter. That is, at least one CSI-RS resource in the NZP-CSI-RS-ResourceSet is transmitted through the same Tx beam. Here, signals of at least one CSI-RS resource in the NZP-CSI-RS-ResourceSet may be transmitted in different OFDM symbols.

Figure 18A:
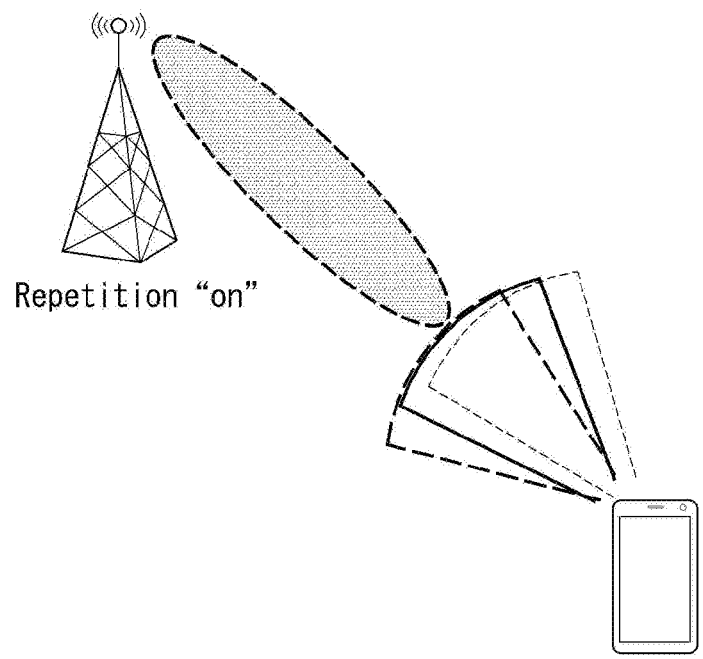
FIGS. 18A and 18B show other examples of DL BM process using a CSI-RS.
Figure 18B:
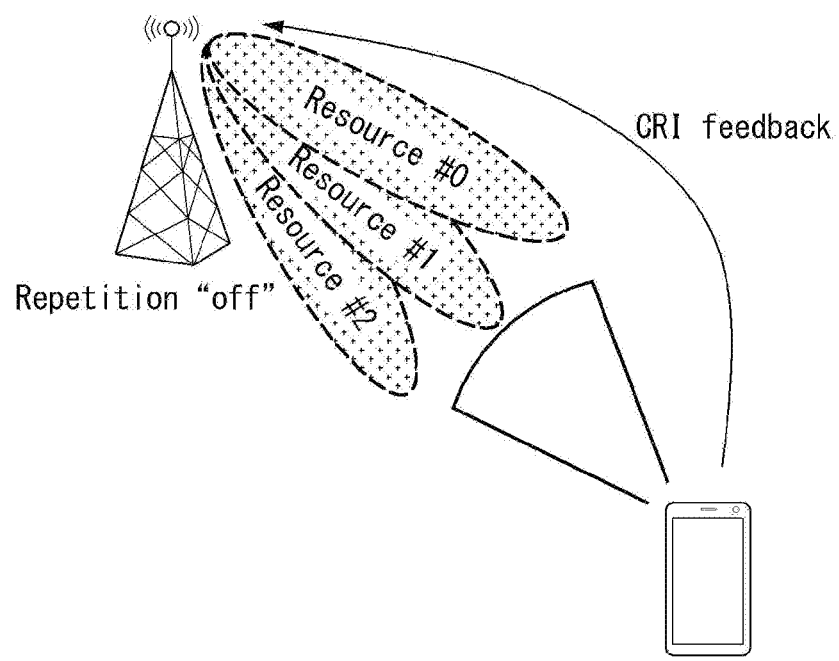

Meanwhile, if the repetition is set to 'OFF', it relates to a Tx beam sweeping process of the BS. If the repetition is set to 'OFF', the UE does not assume that signals of at least one CSI-RS resource in the NZP-CSI-RS-ResourceSet are transmitted in the same downlink spatial domain transmission filter. That is, the signals of at least one CSI-RS resource in the NZP-CSI-RS-ResourceSet are transmitted through different Tx beams. FIGS. 18A and 18B show other examples of the DL BM process using CSI-RS.

FIG. 18A shows a process of Rx beam determination (or refinement) of the UE, and FIG. 18B shows a Tx beam sweeping process of the BS. FIG. 18A shows a case where the repetition parameter is set to 'ON', and FIG. 18B shows a case where the repetition parameter is set to 'OFF'.

A process of determining the Rx beam of the UE will be described with reference to FIGS. 18A and 19.

Figure 19:
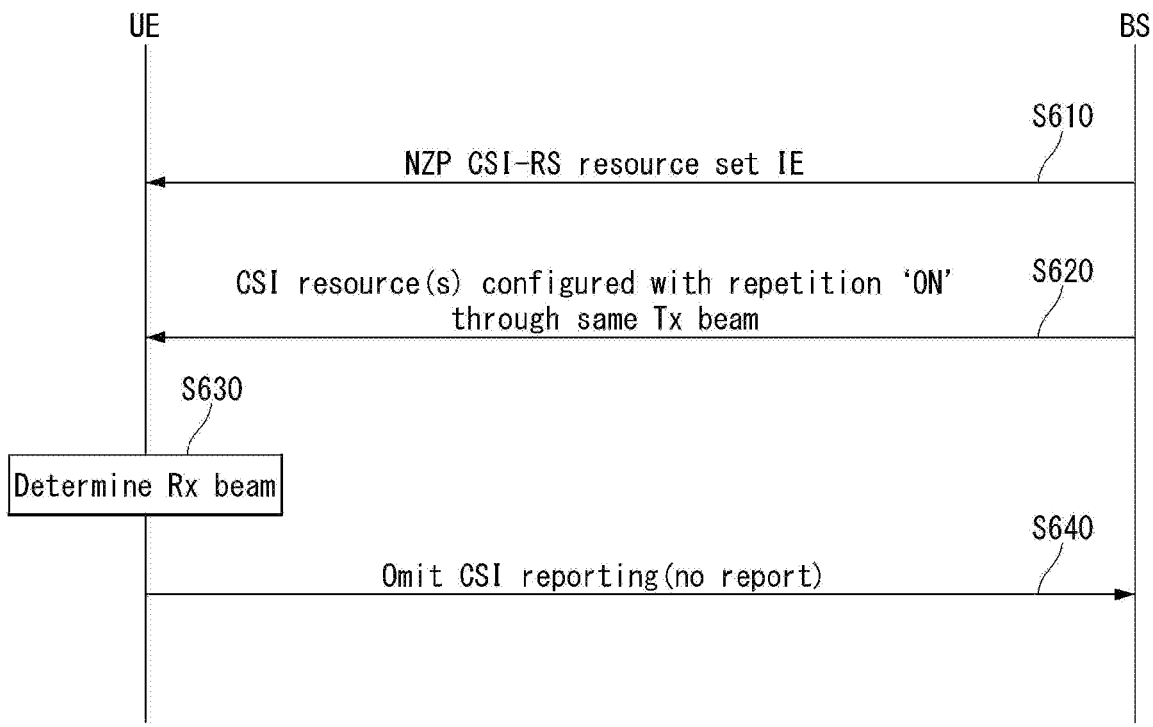
FIG. 19 is a flowchart illustrating an example of a process of determining a reception beam of a UE.

FIG. 19 is a flowchart illustrating an example of a process of determining a reception beam of a UE.

The UE receives an NZP CSI-RS resource set IE including the RRC parameter regarding 'repetition' from the BS through RRC signaling (S610). Here, the RRC parameter 'repetition' is set to 'ON'.

The UE repeatedly receives signals on the resource(s) in the CSI-RS resource in which the RRC parameter 'repetition' is set to 'ON' in different OFDM (s) through the same Tx beam (or DL space domain transmission filter) of the BS (S620).

The UE determines its own Rx beam (S630).

The UE omits the CSI reporting (S640). That is, the UE may omit CSI reporting when the uplink RRC parameter 'repetition' is set to 'ON'.

A Tx beam determining process of the BS will be described with reference to FIGS. 18B and 20.

Figure 20:
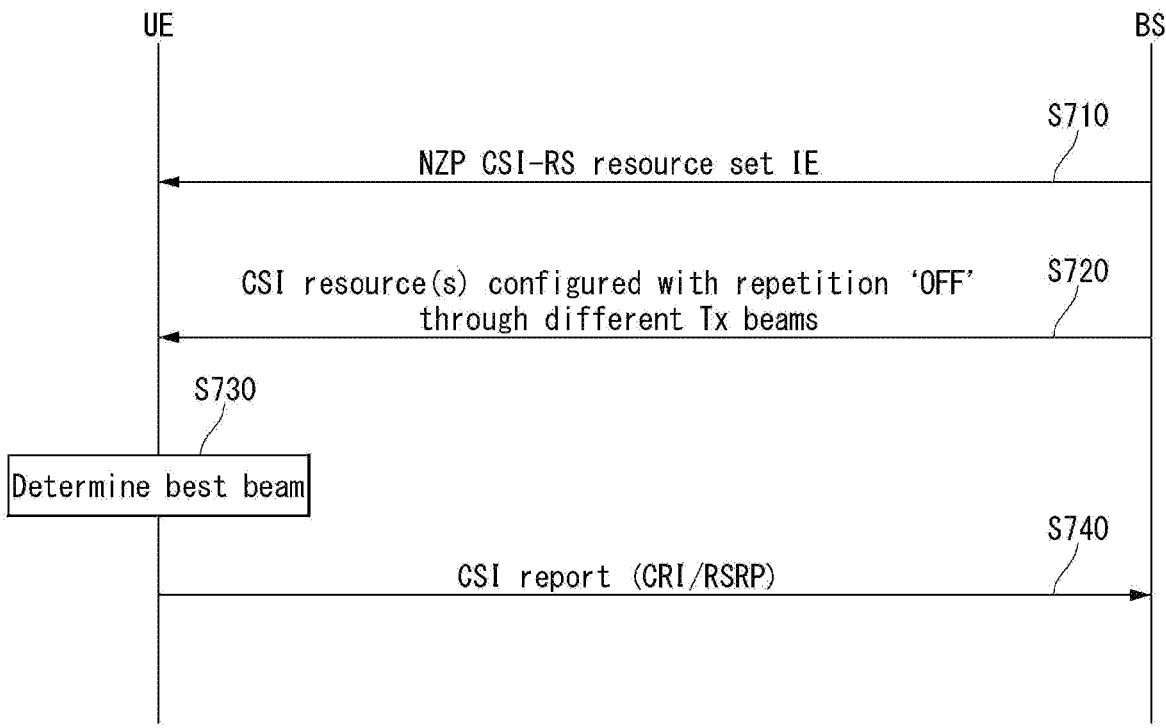
FIG. 20 is a flowchart illustrating an example of a transmission beam determining process of a BS.

FIG. 20 is a flowchart illustrating an example of a transmission beam determining process of the BS.

The UE receives an NZP CSI-RS resource set IE including an RRC parameter regarding 'repetition' from the BS through RRC signaling (S710). Here, the RRC parameter 'repetition' is set to 'OFF' and is related to the Tx beam sweeping process of the BS.

The UE receives signals on the resources in the CSI-RS resource in which the RRC parameter 'repetition' is set to 'OFF' through different Tx beams (DL spatial domain transmission filters) of the BS (S720).

The UE selects (or determines) the best beam (S730)

The UE reports an ID (e.g., CRI) for the selected beam and related quality information (e.g., RSRP) to the BS (S740). That is, the UE reports the CRI and the RSRP to the BS when the CSI-RS is transmitted for the BM.

Figure 21:
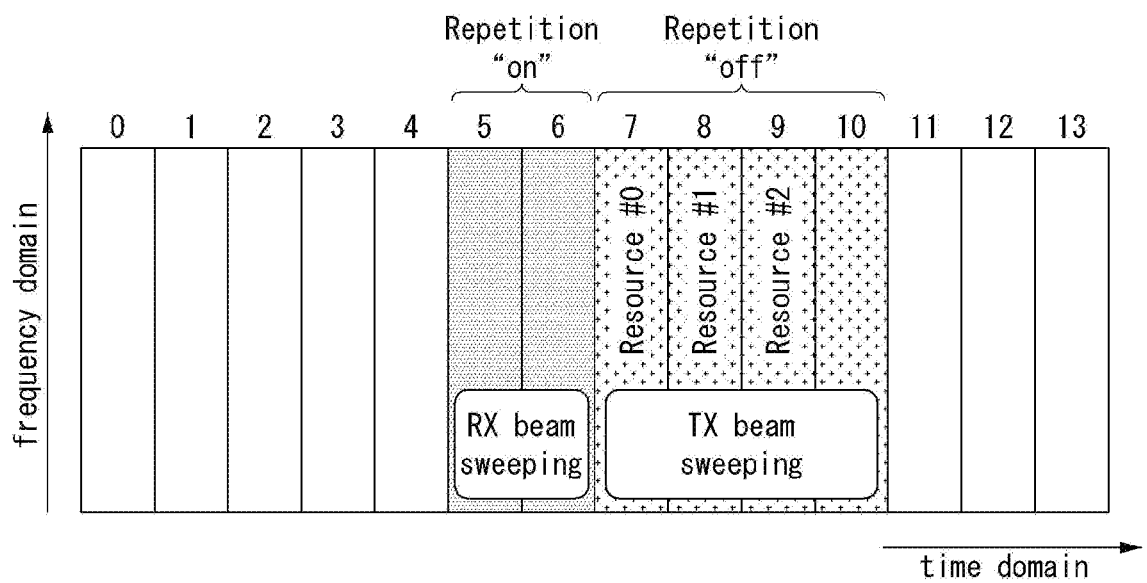
FIG. 21 shows an example of resource allocation in time and frequency domains related to an operation of FIG. 21.

FIG. 21 shows an example of resource allocation in time and frequency domains related to the operation of FIGS. 18A and 18B.

When repetition 'ON' is set in the CSI-RS resource set, a plurality of CSI-RS resources are repeatedly used by applying the same transmission beam, and when repetition 'OFF' is set in the CSI-RS resource set, different CSI-RS resources may be transmitted in different transmission beams.

3. DL BM-Related Beam Indication

The UE may receive a list of up to M candidate transmission configuration indication (TCI) states for at least a quasi co-location (QCL) indication via RRC signaling. Here, M depends on UE capability and may be 64.

Each TCI state may be configured with one reference signal (RS) set. Table 6 shows an example of a TCI-State IE. The TCI-State IE is associated with a quasi co-location (QCL) type corresponding to one or two DL reference signals (RSs).

TABLE 6

```
-- ASN1START
-- TAG-TCI-STATE-START
TCI-State ::=                SEQUENCE {
    tci-StateId                  TCI-StateId,
    qcl-Type1                    QCL-Info,
    qcl-Type2                    QCL-Info
                OPTIONAL, -- Need R
    ...
}
```

TABLE 6-continued

```
QCL-Info ::=                SEQUENCE {
    cell                            ServCellIndex
                OPTIONAL, -- Need R
    bwp-Id                          BWP-Id
                OPTIONAL, -- Cond CSI-RS-Indicated
    referenceSignal                 CHOICE {
        csi-rs                          NZP-CSI-
RS-ResourceId,
        ssb
        SSB-Index
    },
    qcl-Type                    ENUMERATED
{typeA, typeB, typeC, typeD},
    ...
}
-- TAG-TCI-STATE-STOP
-- ASN1STOP
```

In Table 6, 'bwp-Id' denotes a DL BWP where RS is located, 'cell' denotes a carrier where RS is located, 'referencesignal' denotes a reference antenna port(s) which is a QCL-ed source for target antenna port(s) or a reference signal including the same. The target antenna port(s) may be CSI-RS, PDCCH DMRS, or PDSCH DMRS.

4. QCL (Quasi-Co Location)

The UE may receive a list including up to M TCI-state configurations to decode the PDSCH according to the detected PDCCH having an intended DCI for the UE and a given cell. Here, M depends on the UE capability.

As illustrated in Table 6, each TCI-State includes a parameter for establishing a QCL relationship between one or two DL RSs and the DM-RS port of the PDSCH. The QCL relationship is configured with a RRC parameter qcl-Type1 for the first DL RS and a qcl-Type2 (if set) for the second DL RS.

The QCL type corresponding to each DL RS is given by the parameter 'gel-Type' in QCL-Info and may have one of the following values:

'QCL-TypeA': {Doppler shift, Doppler spread, average delay, delay spread}
'QCL-TypeB': {Doppler shift, Doppler spread}
'QCL-TypeC': {Doppler shift, average delay}
'QCL-TypeD': {Spatial Rx parameter}

For example, when a target antenna port is a specific NZP CSI-RS, corresponding NZP CSI-RS antenna ports may be instructed/configured to be QCL-ed with a specific TRS in terms of QCL-Type A and QCL-ed with a specific SSB in terms of QCL-Type D. The thusly instructed/configured UE may receive the corresponding NZP CSI-RS using a Doppler and delay value measured by the QCL-TypeA TRS and apply a reception beam used for receiving the QCL-TypeD SSB to the corresponding NZP CSI-RS reception.

UL BM Process

In the UL BM, a Tx beam-Rx beam reciprocity (or beam correspondence) may be or may not be established depending on UE implementation. If the Tx beam-Rx beam reciprocity is established in both the BS and the UE, a UL beam pair may be matched through a DL beam pair. However, if the Tx beam-Rx beam reciprocity is not established in either the BS or the UE, a UL beam pair determining process is required, apart from DL beam pair determination.

In addition, even when the BS and the UE maintain beam correspondence, the BS may use the UL BM process for DL Tx beam determination without requesting the UE to report a preferred beam.

The UL BM may be performed through beamformed UL SRS transmission and whether to apply the UL BM of the SRS resource set is configured by the RRC parameter in a (RRC parameter) usage. If the usage is configured as 'Beam-Management (BM)', only one SRS resource may be transmitted for each of a plurality of SRS resource sets at a given time instant.

The UE may be configured with one or more sounding reference signal (SRS) resource sets (through RRC signaling, etc.) set by the (RRC parameter) SRS-ResourceSet. For each SRS resource set, K≥1 SRS resources may be set for the UE. Here, K is a natural number, and a maximum value of K is indicated by SRS capability.

Like the DL BM, the UL BM process may also be divided into Tx beam sweeping of the UE and Rx beam sweeping of the BS.

Figure 22A:
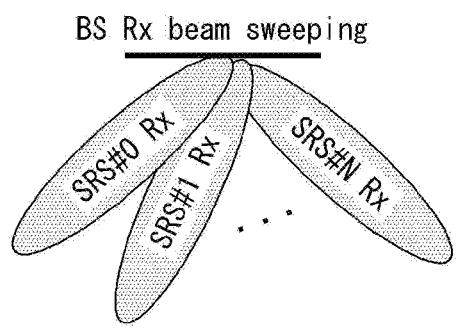
FIGS. 22A and 22B show examples of a UL BM process using an SRS.
Figure 22A:
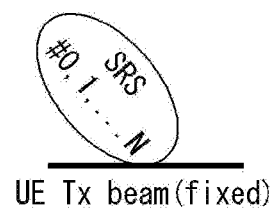
Figure 22B:
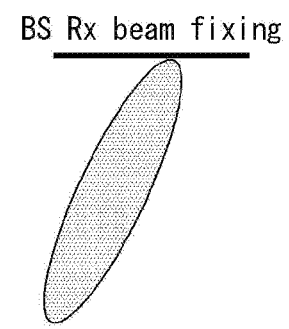
Figure 22B:
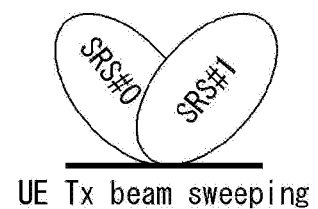

FIGS. 22A and 22B show examples of a UL BM process using SRS.

FIG. 22A shows a process of determining Rx beamforming of a BS, and FIG. 22B shows a process of sweeping Tx beam of the UE.

Figure 23:
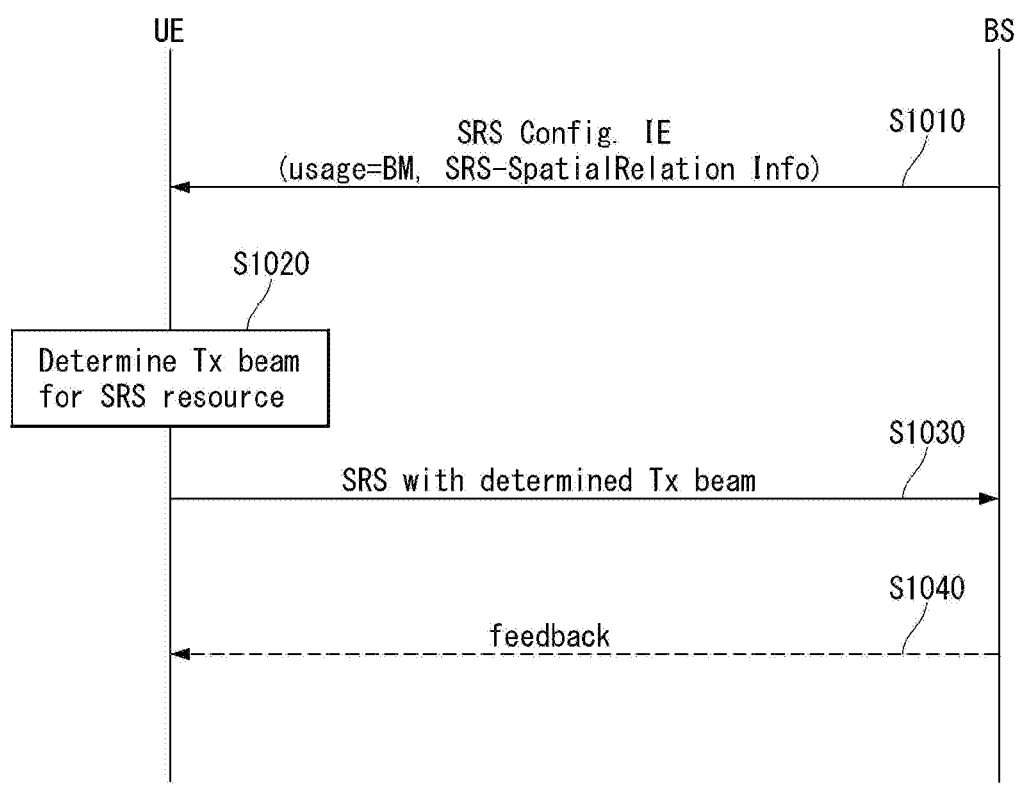
FIG. 23 is a flowchart illustrating an example of a UL BM process using an SRS.

FIG. 23 is a flowchart illustrating an example of a UL BM process using SRS.

The UE receives RRC signaling (e.g., SRS-Config IE) including an (RRC parameter) usage parameter set to 'beam management' from the BS (S1010). An SRS-Config IE is used for configuration of SRS transmission. The SRS-Config IE includes a list of SRS-Resources and a list of SRS-ResourceSets. Each SRS resource set refers to a set of SRS-resources.

The UE determines Tx beamforming for the SRS resource to be transmitted on the basis of SRS-SpatialRelation Info included in the SRS-Config IE (S1020). Here, the SRS-SpatialRelation Info is configured for each SRS resource and indicates whether to apply the same beamforming as that used in SSB, CSI-RS, or SRS for each SRS resource.

If SRS-SpatialRelationInfo is configured in the SRS resource, the same beamforming as that used in SSB, CSI-RS, or SRS is applied and transmitted. However, if SRS-SpatialRelationInfo is not configured in the SRS resource, the UE randomly determines the Tx beamforming and transmits the SRS through the determined Tx beamforming (S1030).

More specifically, regarding P-SRS in which 'SRS-ResourceConfigType' is set to 'periodic':

i) If the SRS-SpatialRelationInfo is set to SSB/PBCH', the UE transmits the corresponding SRS by applying the same spatial domain transmission filter (or generated from the corresponding filter) as the spatial domain Rx filter used for receiving SSB/PBCH; or ii) If the SRS-SpatialRelationInfo is set to 'CSI-RS', the UE transmits the SRS by applying the same spatial domain transmission filter used for receiving the CSI-RS; or iii) When SRS-SpatialRelationInfo is set to 'SRS', the UE transmits the corresponding SRS by applying the same spatial domain transmission filter used for transmitting the SRS.

In addition, the UE may receive or may not receive a feedback on the SRS from the BS as in the following three cases (S1040).

i) When Spatial_Relation_Info is set for all SRS resources in the SRS resource set, the UE transmits the SRS to the beam indicated by the BS. For example, if Spatial_Relation_Info indicates SSB, CRI, or SRI in which Spatial_Relation_Info is the same, the UE repeatedly transmits the SRS on the same beam.

ii) Spatial_Relation_Info may not be set for all SRS resources in the SRS resource set. In this case, the UE may freely transmit while changing the SRS beamforming.

iii) Spatial_Relation_Info may only be set for some SRS resources in the SRS resource set. In this case, the SRS is transmitted on the indicated beam for the set SRS resource, and for an SRS resource in which Spatial_Relation_Info is not set, the UE may transit the SRS resource by randomly applying Tx beamforming.

A Beam Failure Recovery (BFR) Process

In a beamformed system, a radio link failure (RLF) may occur frequently due to rotation, movement, or beamforming blockage of the UE. Therefore, BFR is supported in NR to prevent frequent occurrence of the RLFs. The BFR is similar to the radio link failure recovery process and may be supported if the UE knows the new candidate beam(s).

For beam failure detection, the BS configures beam failure detection reference signals for the UE, and if the number of times of beam failure indications from the physical layer of the UE reaches a threshold set by the RRC signaling within a period set by the RRC signaling of the BS, the UE declares beam failure.

After the beam failure is detected, the UE triggers a beam failure recovery by initiating a random access procedure on the PCell; and performs beam failure recovery by selecting a suitable beam (If the BS provides dedicated random access resources for certain beams, they are prioritized by the UE). Upon completion of the random access procedure, beam failure recovery is considered to be completed.

J. URLLC (Ultra-Reliable and Low Latency Communication)

The URLLC transmission defined by the NR may refer to transmission for (1) a relatively low traffic size, (2) a relatively low arrival rate, (3) an extremely low latency requirement (e.g., 0.5, 1 ms), (4) relatively short transmission duration (e.g., 2 OFDM symbols), and (5) urgent service/message, etc.

In the case of UL, transmission for a particular type of traffic (e.g., URLLC) needs to be multiplexed with other previously scheduled transmissions (e.g., eMBB) to meet a more stringent latency requirement. In this regard, one method is to give information indicating that a scheduled UE will be preempted for a specific resource, and allow the URLLC UE to use the resource for UL transmission.

Pre-Emption Indication

In the case of NR, dynamic resource sharing between eMBB and URLLC is supported. eMBB and URLLC services may be scheduled on non-overlapping time/frequency resources and URLLC transmission may occur on scheduled resources for ongoing eMBB traffic. The eMBB UE may not know whether PDSCH transmission of the UE is partially punctured and the UE may not be able to decode the PDSCH due to corrupted coded bits. In consideration of this, NR provides a preemption indication.

The preemption indication may also be referred to as an interrupted transmission indication.

With respect to the preamble indication, the UE receives DownlinkPreemption IE through RRC signaling from the BS. Table 7 below shows an example of the DownlinkPreemption IE.

TABLE 7

```
-- ASN1START
-- TAG-DOWNLINKPREEMPTION-START
DownlinkPreemption ::=          SEQUENCE {
    int-RNTI                        RNTI-Value,
    timeFrequencySet                ENUMERATED {set0, set1},
    dci-PayloadSize                 INTEGER (0..maxINT-DCI-PayloadSize),
    int-ConfigurationPerServingCell SEQUENCE (SIZE (1..maxNrofServingCells))
OF INT-ConfigurationPerServingCell,
    ...
}
INT-ConfigurationPerServingCell ::= SEQUENCE {
    servingCellId                   ServCellIndex,
    positionInDCI                   INTEGER (0..maxINT-DCI-PayloadSize−1)
}
-- TAG-DOWNLINKPREEMPTION-STOP
-- ASN1STOP
```

If the UE is provided with the DownlinkPreemption IE, the UE is configured with an INT-RNTI provided by a parameter int-RNTI in the DownlinkPreemption IE to monitor a PDCCH conveying the DCI format 2_1. The UE is further configured with a set of serving cells and a corresponding set of locations for fields in the DCI format 2_1 by positionInDCI by an INT-ConfigurationPerServing Cell including a set of serving cell indices provided by a servingCellID, is configured with an information payload size for DCI format 2_1 by dci-PayloadSize, and is configured with granularity of time-frequency resources by timeFrequencySect.

The UE receives the DCI format 2_1 from the BS on the basis of the DownlinkPreemption IE.

If the UE detects the DCI format 2_1 for a serving cell in the set of serving cells, the UE may assume there is no transmission to the UE in PRBs and symbols indicated by the DCI format 2_1 among sets of PRBs and sets of symbols in the last monitoring period before a monitoring period to which the DCI format 2_1 belongs. For example, referring to FIG. 9A, the UE determines that a signal in the time-frequency resource indicated by pre-emption is not a DL transmission scheduled for the UE itself and decodes data on the basis of signals received in the remaining resource area.

Figure 24:
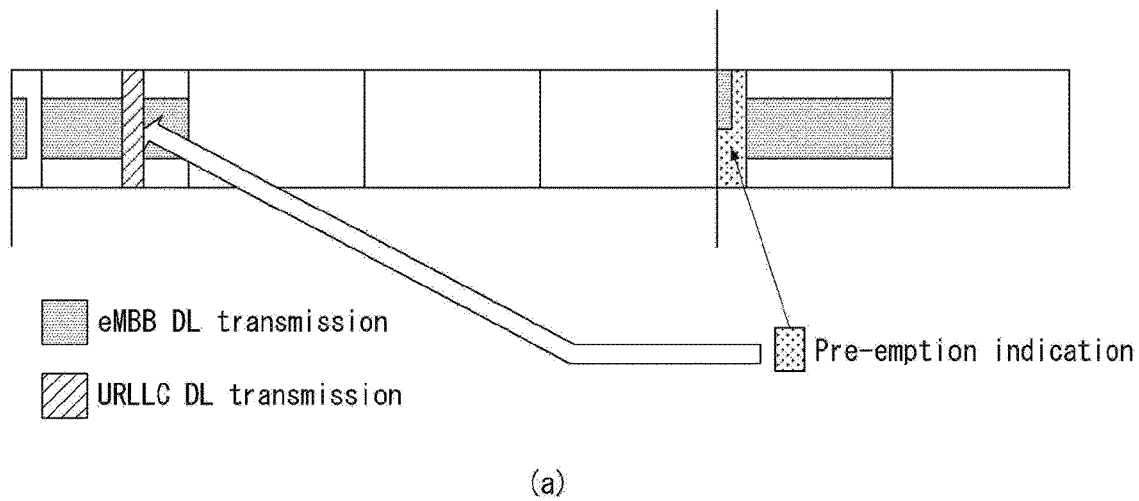
FIG. 24 is a diagram showing an example of a method of indicating a pre-emption.
Figure 24:
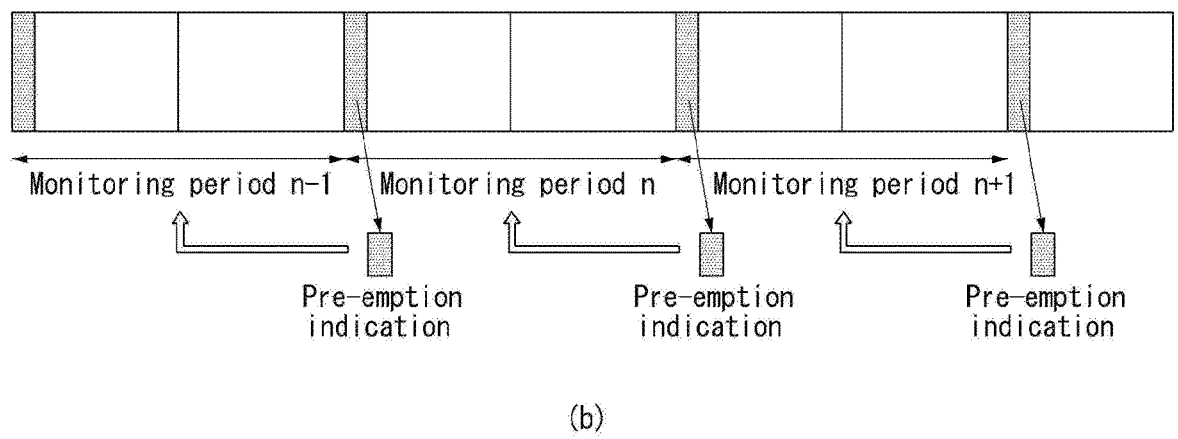

FIG. 24 is a diagram showing an example of an preemption indication method.

A combination of {M,N} is set by the RRC parameter timeFrequencySet. {M, N}={14,1}, {7,2}.

Figure 25:
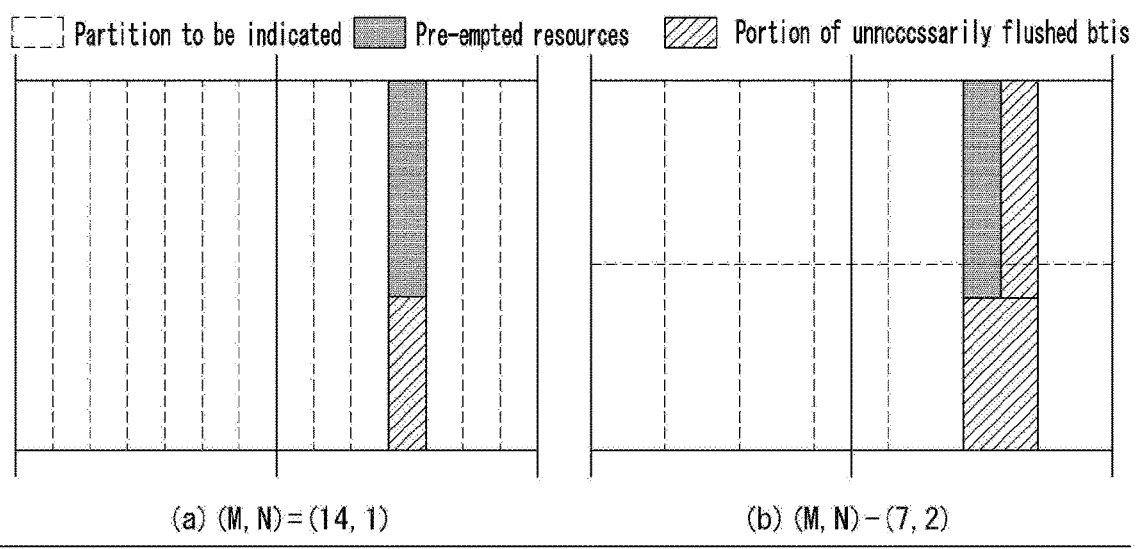
FIG. 25 shows an example of a time/frequency set of pre-emption indication.

FIG. 25 shows an example of a time/frequency set of a preemption indication.

A 14-bit bitmap for a preemption indication indicates one or more frequency parts (N>=1) and/or one or more time domain parts (M>=1). In the case of {M, N}={14,1}, as shown in part (a) of FIG. 25, 14 parts in the time domain correspond one-to-one to 14 bits of the 14-bit bit map, and a part corresponding to a bit set to 1, among the 14 bits, is part including preempted resources. In the case of {M, N}={7,2}, as shown in part (b) of FIG. 25, the time-frequency resources of the monitoring period is divided into seven parts in the time domain and two parts in the frequency domain, so as to be divided into a total of 14 time-frequency parts. The total of 14 time-frequency parts correspond one-to-one to the 14 bits of the 14-bit bitmap, and the part corresponding to the bit set to 1 among the 14 bits includes the pre-empted resources.

K. MMTC (Massive MTC)

The massive machine type communication (mMTC) is one of the 5G scenarios for supporting a hyper-connection service that simultaneously communicates with a large number of UEs. In this environment, the UE intermittently performs communication with a very low transfer rate and mobility. Therefore, mMTC is aimed at how low cost and for how long the UE can be driven. In this regard, MTC and NB-IoT, which are dealt with in 3GPP will be described.

Hereinafter, a case where a transmission time interval of a physical channel is a subframe will be described as an example. For example, a case where a minimum time interval from a start of transmission of one physical channel (e.g., MPDCCH, PDSCH, PUCCH, PUSCH) to a start of transmission of a next physical channel is one subframe will be described as an example. In the following description, the subframe may be replaced by a slot, a mini-slot, or multiple slots.

MTC (Machine Type Communication)

MTC (Machine Type Communication), which is an application that does not require much throughput applicable to M2M (Machine-to-Machine) or IoT (Internet-of-Things), refers to a communication technology adopted to meet the requirements of the IoT service in 3GPP (3rd Generation Partnership Project).

The MTC may be implemented to meet the criteria of (1) low cost & low complexity, (2) enhanced coverage, and (3) low power consumption.

In 3GPP, MTC has been applied since release 10 (3GPP standard document version 10.x.x.) and features of MTC added for each release of 3GPP will be briefly described.

First, the MTC described in 3GPP Release 10 and Release 11 relates to a load control method. The load control method is to prevent IoT (or M2M) devices from suddenly loading the BS. More specifically, 3GPP Release 10 relates to a method of controlling a load by disconnecting IoT devices when the load occurs, and Release 11 relates to a method of preventing connection of the UE in advance by informing the UE about connection to a cell later through system information of the cell. In Release 12, features for low cost MTC are added, for which UE category 0 is newly defined. The UE category is an indicator indicating how much data the UE may handle at a communication modem. A UE in UE category 0 is a UE with a reduced peak data rate and relaxed radio frequency (RF) requirements, thus reducing baseband and RF complexity. In Release 13, a technology called eMTC (enhanced MTC) was introduced, which allows the UE to operate only at 1.08 MHz, a minimum frequency bandwidth supported by legacy LTE, thereby lowering the price and power consumption of the UE.

The contents described hereinafter is features mainly related to eMTC but may also be equally applicable to the MTC, eMTC, 5G (or NR) unless otherwise mentioned. Hereinafter, for convenience of explanation, MTC will be collectively described.

Therefore, the MTC described below may referred to as the enhanced MTC (eMTC), the LTE-M1/M2, BL (bandwidth reduced low complexity/CE (coverage enhanced), non-BL UE (in enhanced coverage), NR MTC, enhanced BL/CE, and the like. That is, the term MTC may be replaced with terms to be defined in the 3GPP standard in the future.

MTC General Features (1) MTC operates only within a specific system bandwidth (or channel bandwidth).

Figure 26:
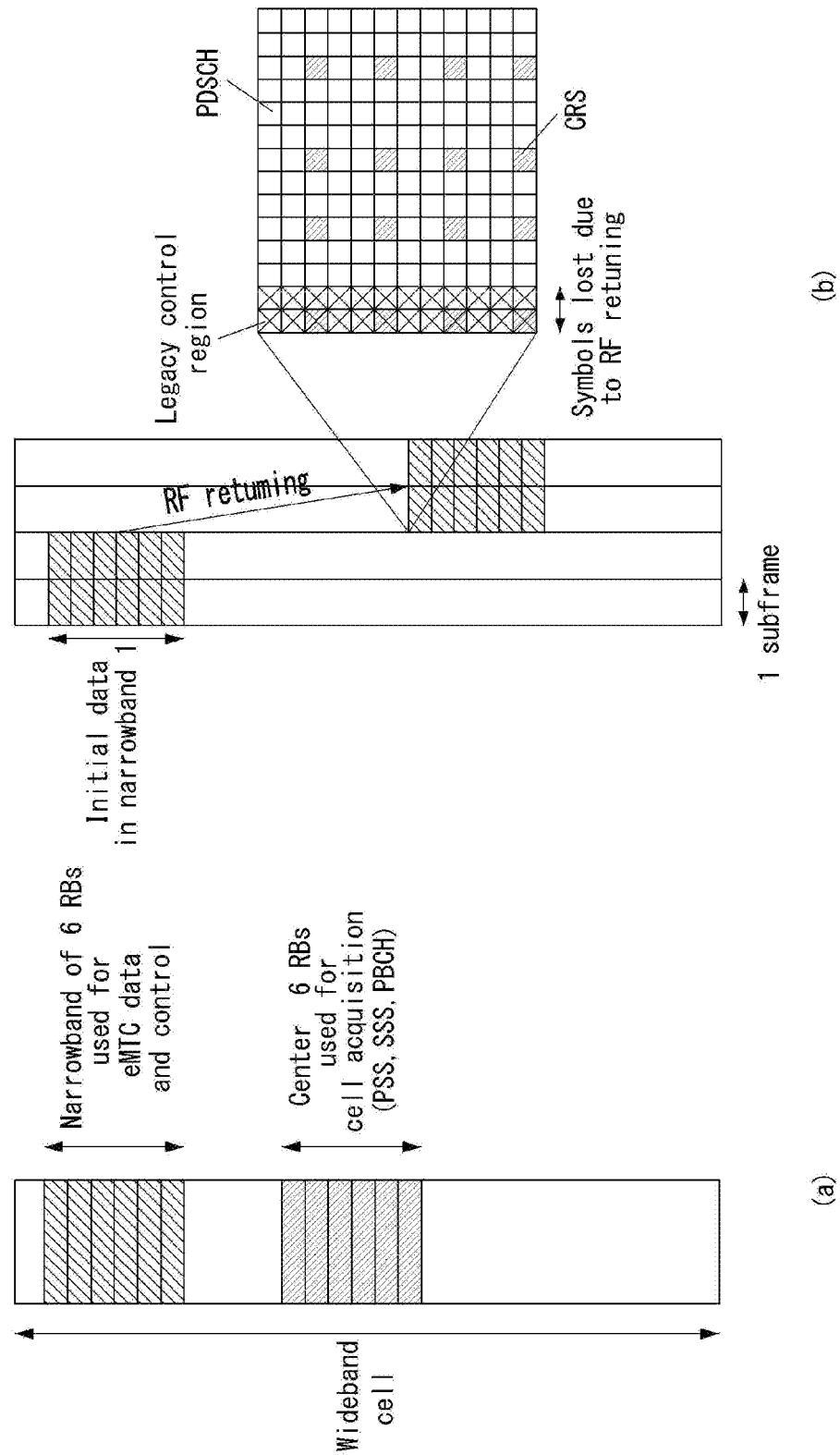
FIG. 26 shows an example of a narrowband operation and frequency diversity.

MTC may use six resource blocks (RBs) in the system band of the legacy LTE as shown in FIG. 26 or use a specific number of RBs in the system band of the NR system. The frequency bandwidth in which the MTC operates may be defined in consideration of a frequency range of NR and subcarrier spacing. Hereinafter, a specific system or frequency bandwidth in which the MTC operates is referred to as an MTC narrowband (NB). In the NR, the MTC may operate in at least one bandwidth part (BWP) or in a specific band of BWP.

MTC follows a narrowband operation to transmit and receive physical channels and signals, and a maximum channel bandwidth in which the MTC UE is operable is reduced to 1.08 MHz or six (LTE) RBs.

The narrowband may be used as a reference unit in resource allocation units of some downlink and uplink channels, and a physical location of each narrowband in the frequency domain may be defined to be different depending on the system bandwidth.

The bandwidth of 1.08 MHz defined in MTC is defined for the MTC UE to follow the same cell search and random access procedure as the legacy UE.

MTC may be supported by cells having a bandwidth (e.g., 10 MHz) much larger than 1.08 MHz but the physical channels and signals transmitted and received by the MTC are always limited to 1.08 MHz. The system with having much larger bandwidth may be legacy LTE, NR systems, 5G systems, and the like.

A narrowband is defined as six non-overlapping consecutive physical resource blocks in the frequency domain.

Part (a) of FIG. 26 is a diagram showing an example of a narrowband operation, and part (b) of FIG. 26 is a diagram showing an example of repetition having RF retuning.

Frequency diversity by RF retuning will be described with reference to part (b) of FIG. 26.

Due to narrowband RF, single antenna and limited mobility, the MTC supports limited frequency, space and time diversity. In order to reduce fading and outage, frequency hopping is supported by MTC between different narrow bands by RF retuning.

In MTC, frequency hopping is applied to different uplink and downlink physical channels when repetition is possible. For example, if 32 subframes are used for PDSCH transmission, first 16 subframes may be transmitted on a first narrowband. Here, the RF front end is retuned to another narrow band, and the remaining 16 subframes are transmitted on the second narrow band.

The narrowband of MTC may be set to the UE via system information or DCI (downlink control information) transmitted by the BS.

(2) The MTC operates in a half duplex mode and uses a limited (or reduced) maximum transmit power. The half duplex mode refers to a mode in which a communication device operates only in an uplink or a downlink at one frequency at one time point and operates in a downlink or an uplink at another frequency at another time point. For example, when the communication device operates in the half-duplex mode, the communication device performs communication using the uplink frequency and the downlink frequency, and the communication device may not use the uplink frequency and the downlink frequency at the same time. The communication device divides time to perform uplink transmission through the uplink frequency and the downlink reception by re-tuning to the downlink frequency for another predetermined time.

(3) MTC does not use channels (defined in legacy LTE or NR) that must be distributed over the entire system bandwidth of the legacy LTE or NR. For example, in the MTC, the PDCCH of the legacy LTE is not used because the PDCCH is distributed over the entire system bandwidth. Instead, a new control channel, MPDCCH (MTC PDCCH), is defined in the MTC. The MPDCCH is transmitted/received within a maximum of 6 RBs in the frequency domain.

(4) MTC uses the newly defined DCI format. For example, DCI formats 6-0A, 6-0B, 6-1A, 6-1B, 6-2, etc., may be used as a DCI format for MTC (see 3GPP TS 36.212).

(5) In the case of MTC, a physical broadcast channel (PBCH), a physical random access channel (PRACH), an MTC physical downlink control channel (M-PDCCH), a physical downlink shared channel (PDSCH), a physical uplink control channel (PUCCH), and a physical uplink shared channel (PUSCH) may be repeatedly transmitted. Due to the MTC repeated transmission, an MTC channel may be decoded even when signal quality or power is very poor, such as in an inadequate environment such as a basement, thereby increasing a cell radius and increasing a penetration effect.

(6) In MTC, PDSCH transmission based on PDSCH scheduling (DCI) and PDSCH scheduling may occur in different subframes (cross-subframe scheduling).

(7) In the LTE system, the PDSCH carrying a general SIB1 is scheduled by the PDCCH, whereas all the resource allocation information (e.g., subframe, transport block size, narrowband index) for SIB1 decoding is determined by a parameter of the MIB and no control channel is used for SIB1 decoding of the MTC.

(8) All resource allocation information (subframe, TBS, subband index) for SIB2 decoding is determined by several SIB1 parameters and no control channel for SIB2 decoding of MTC is used.

(9) The MTC supports an extended paging (DRX) cycle. Here, the paging period refers to a period during which the UE must be wake up to check whether there is a paging from a network even when the UE is in a discontinuous reception (DRX) mode in which it does not attempt to receive a downlink signal for power saving.

(10) MTC may use the same PSS (Primary Synchronization Signal)/SSS (Secondary Synchronization Signal)/CRS (Common Reference Signal) used in legacy LTE or NR. In the case of NR, the PSS/SSS is transmitted on an SSB basis, and a tracking RS (TRS) is a cell-specific RS and may be used for frequency/time tracking.

MTC Operation Mode and Level

Next, an MTC operation mode and level will be described. MTC is classified into two operation modes (first mode, second mode) and four different levels for coverage improvement as shown in Table 8 below.

The MTC operation mode is referred to as a CE (Coverage Enhancement) mode. In this case, the first mode may be referred to as a CE mode A, and the second mode may be referred to as a CE mode B.

TABLE 8

| Mode | Level | Description |
| --- | --- | --- |
| Mode A | Level 1 | No repetition for PRACH |
|  | Level 2 | Small Number of Repetition for PRACH |
| Mode B | Level 3 | Medium Number of Repetition for PRACH |
|  | Level 4 | Large Number of Repetition for PRACH |

The first mode is defined for small coverage enhancement to support full mobility and CSI (channel state information, in which there is no repetition or fewer repetition times. The second mode is defined for UEs with extremely poor coverage conditions that support CSI feedback and limited mobility, in which a large number of repetitive transmissions is defined. The second mode provides a coverage improvement of up to 15 dB. Each level of MTC is defined differently in the random access procedure and the paging process.

The MTC operation mode is determined by the BS, and each level is determined by the MTC UE. Specifically, the BS transmits RRC signaling including information on the MTC operation mode to the UE. Here, the RRC signaling may be an RRC connection setup message, an RRC connection reconfiguration message or an RRC connection reestablishment message.

Thereafter, the MTC UE determines a level in each operation mode and transmits the determined level to the BS. Specifically, the MTC UE determines a level in an operation mode on the basis of measured channel quality (e.g., reference signal received power (RSRP), reference signal received quality (RSRQ), or signal to interference plus noise ratio (SINR), and transmits an RACH preamble using a PRACH resource (e.g., frequency, time, preamble resource for PRACH) corresponding to the determined level, thereby informing the BS about the determined level.

MTC Guard Period

As discussed above, MTC operates in narrow band. The location of the narrow band used in the MTC may be different for each particular time unit (e.g., subframe or slot). The MTC UE may tune to different frequencies depending on the time units. A certain amount of time is required for frequency retuning, and certain amount of time is defined as a guard period of MTC. That is, a guard period is required when frequency retuning is performed while transitioning from one time unit to the next time unit, and transmission and reception do not occur during the guard period.

MTC Signal Transmission/Reception Method

Figure 27:
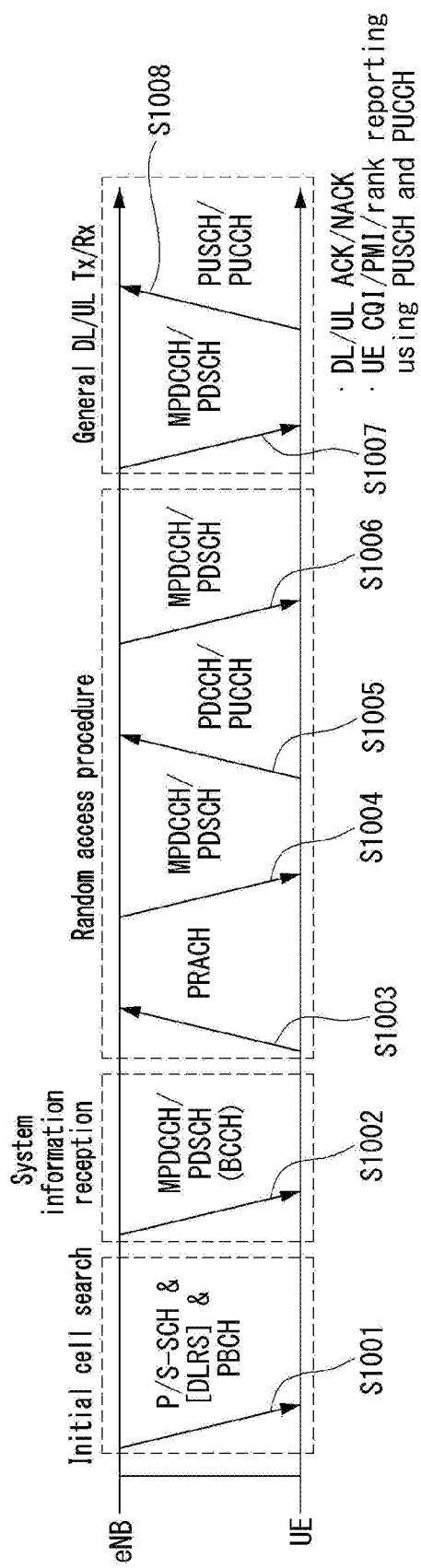
FIG. 27 is a diagram illustrating physical channels that may be used for MTC and a general signal transmission method using the same.

FIG. 27 is a diagram illustrating physical channels that may be used for MTC and a general signal transmission method using the same.

In step S1001, the MTC UE, which is powered on again or enters a new cell, performs an initial cell search operation such as synchronizing with the BS. To this end, the MTC UE receives a primary synchronization signal (PSS) and a secondary synchronization signal (SSS) from the BS, adjusts synchronization with the BS, and acquires information such as a cell ID. The PSS/SSS used in the initial cell search operation of the MTC may be a PSS/SSS, a resynchronization signal (RSS), or the like of an legacy LTE.

Thereafter, the MTC UE may receive a physical broadcast channel (PBCH) signal from the BS to acquire broadcast information in a cell.

Meanwhile, the MTC UE may receive a downlink reference signal (DL RS) in an initial cell search step to check a downlink channel state. The broadcast information transmitted through the PBCH is a master information block (MIB), and in the LTE, the MIB is repeated by every 10 ms.

Among the bits of the MIB of the legacy LTE, reserved bits are used in MTC to transmit scheduling for a new SIB1-BR (system information block for bandwidth reduced device) including a time/frequency location and a transport block size. The SIB-BR is transmitted directly on the PDSCH without any control channel (e.g., PDCCH, MPDDCH) associated with the SIB-BR.

Upon completion of the initial cell search, the MTC UE may receive an MPDCCH and a PDSCH according to the MPDCCH information to acquire more specific system information in step S1002. The MPDCCH may be transmitted only once or repeatedly. The maximum number of repetitions of the MPDCCH is set to the UE by RRC signaling from the BS.

Thereafter, the MTC UE may perform a random access procedure such as steps S1003 to S1006 to complete the connection to the BS. A basic configuration related to the RACH process of the MTC UE is transmitted by SIB2. In addition, SIB2 includes parameters related to paging. In the 3GPP system, a paging occasion (PO) refers to a time unit in which the UE may attempt to receive paging. The MTC UE attempts to receive the MPDCCH on the basis of a P-RNTI in the time unit corresponding to its PO on the narrowband (PNB) set for paging. The UE that has successfully decoded the MPDCCH on the basis of the P-RNTI may receive a PDSCH scheduled by the MPDCCH and check a paging message for itself. If there is a paging message for itself, the UE performs a random access procedure to access a network.

For the random access procedure, the MTC UE transmits a preamble through a physical random access channel (PRACH) (S1003), and receives a response message (RAR) for the preamble through the MPDCCH and the corresponding PDSCH. (S1004). In the case of a contention-based random access, the MTC UE may perform a contention resolution procedure such as transmission of an additional PRACH signal (S1005) and reception of the MPDCCH signal and corresponding PDSCH signal (S1006). The signals and/or messages Msg 1, Msg 2, Msg 3, and Msg 4 transmitted in the RACH process in the MTC may be repeatedly transmitted, and the repeat pattern is set to be different according to the CE level. Msg1 denotes a PRACH preamble, Msg2 denotes a random access response (RAR), Msg3 denotes UL transmission on the basis of a UL grant included in the RAR, and Msg4 denotes a DL transmission of the BS to Msg3.

For random access, PRACH resources for the different CE levels are signaled by the BS. This provides the same control of a near-far effect on the PRACH by grouping together UEs experiencing similar path loss. Up to four different PRACH resources may be signaled to the MTC UE.

The MTC UE estimates RSRP using a downlink RS (e.g., CRS, CSI-RS, TRS, and the like), and selects one of different PRACH resources (e.g., frequency, time, and preamble resources for PRACH) for the random access on the basis of the measurement result. The RAR for the PRACH and search spaces for the contention resolution messages for PRACH are also signaled at the BS via system information.

The MTC UE that has performed the above-described process may then receive an MPDCCH signal and/or a PDSCH signal (S1007) and transmit a physical uplink shared channel (PUSCH) signal and/or a physical uplink control channel (PUCCH) (S1108) as a general uplink/downlink signal transmission process. The MTC UE may transmit uplink control information (UCI) to the BS through the PUCCH or PUSCH. The UCI may include HARQ-ACK/NACK, scheduling request (SR), and/or CSI.

When RRC connection to the MTC UE is established, the MTC UE monitors the MPDCCH in a search space set to acquire uplink and downlink data allocation and attempts to receive the MDCCH.

In the case of MTC, the MPDCCH and the PDSCH scheduled by the MDCCH are transmitted/received in different subframes. For example, the MPDCCH having the last repetition in subframe #n schedules the PDSCH starting at subframe #n+2. The DCI transmitted by the MPDCCH provides information on how many times the MPDCCH is repeated so that the MTC UE may know when the PDSCH transmission is started. For example, when the DCI in the MPDCCH started to be transmitted from the subframe #n includes information that the MPDCCH is repeated 10 times, a last subframe in which the MPDCCH is transmitted is the subframe #n+9 and transmission of the PDSCH may start at subframe #n+11.

The PDSCH may be scheduled in the same as or different from a narrow band in which the MPDCCH scheduling the PDSCH is present. If the MPDCCH and the corresponding PDSCH are located in different narrow bands, the MTC UE needs to retune the frequency to the narrow band in which the PDSCH is present before decoding the PDSCH.

For uplink data transmission, scheduling may follow the same timing as legacy LTE. For example, the MPDCCH which is lastly transmitted at subframe #n may schedule PUSCH transmission starting at subframe #n+4.

Figure 28:
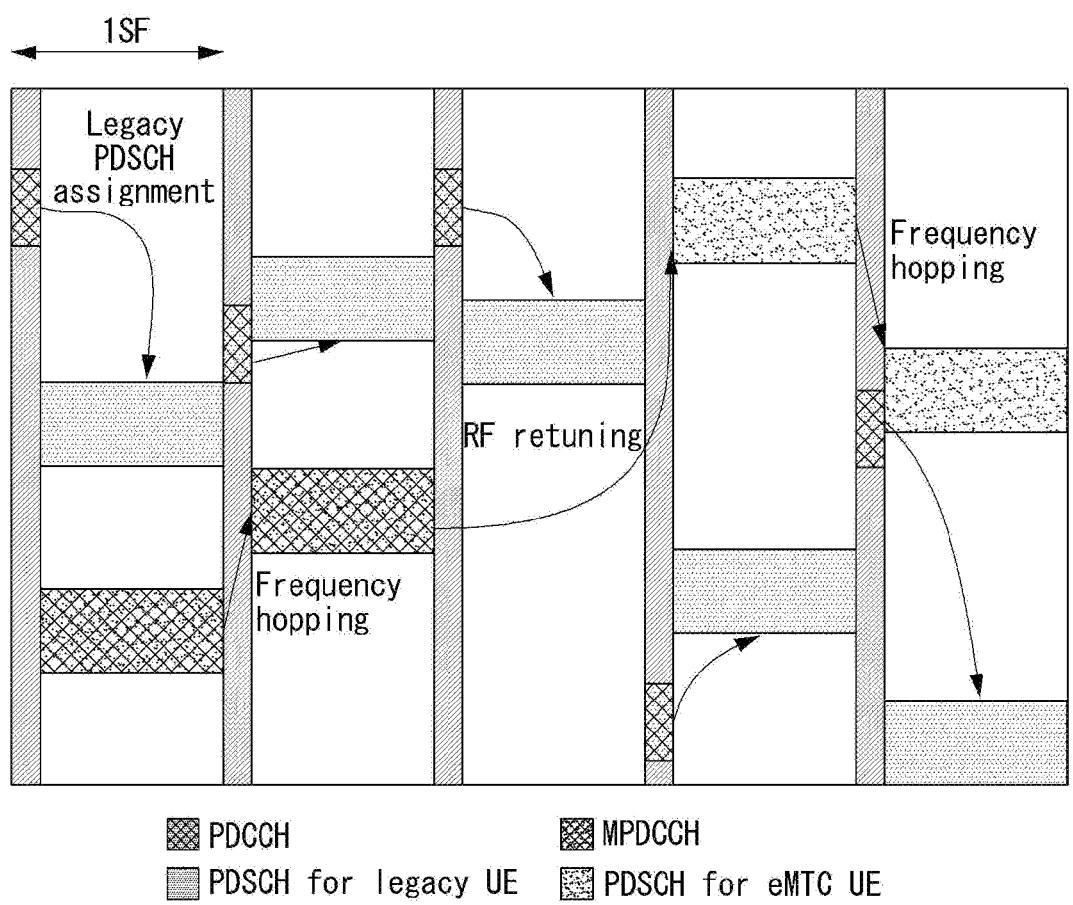
FIG. 28 is a diagram illustrating an example of scheduling for each of MTC and legacy LTE.

FIG. 28 shows an example of scheduling for MTC and legacy LTE, respectively.

In the legacy LTE, the PDSCH is scheduled using the PDCCH, which uses the first OFDM symbol(s) in each subframe, and the PDSCH is scheduled in the same subframe as the subframe in which the PDCCH is received.

In contrast, the MTC PDSCH is cross-subframe scheduled, and one subframe between the MPDCCH and the PDSCH is used as a time period for MPDCCH decoding and RF retuning. The MTC control channel and data channel may be repeated over a large number of subframes including up to 256 subframes for the MPDCCH and up to 2048 subframes for the PDSCH so that they may be decoded under extreme coverage conditions.

NB-IoT (Narrowband-Internet of Things)

The NB-IoT may refer to a system for supporting low complexity, low power consumption through a system bandwidth (system BW) corresponding to one resource block (RB) of a wireless communication system.

Here, NB-IoT may be referred to as other terms such as NB-LTE, NB-IoT enhancement, enhanced NB-IoT, further enhanced NB-IoT, NB-NR. That is, NB-IoT may be replaced with a term defined or to be defined in the 3GPP standard, and hereinafter, it will be collectively referred to as 'NB-IoT' for convenience of explanation.

The NB-IoT is a system for supporting a device (or UE) such as machine-type communication (MTC) in a cellular system so as to be used as a communication method for implementing IoT (i.e., Internet of Things). Here, one RB of the existing system band is allocated for the NB-IoT, so that the frequency may be efficiently used. Also, in the case of NB-IoT, each UE recognizes a single RB as a respective carrier, so that RB and carrier referred to in connection with NB-IoT in the present specification may be interpreted to have the same meaning.

Hereinafter, a frame structure, a physical channel, a multi-carrier operation, an operation mode, and general signal transmission/reception related to the NB-IoT in the present specification are described in consideration of the case of the legacy LTE system, but may also be extendedly applied to a next generation system (e.g., an NR system, etc.). In addition, the contents related to NB-IoT in this specification may be extendedly applied to MTC (Machine Type Communication) oriented for similar technical purposes (e.g., low-power, low-cost, coverage enhancement, etc.).

Hereinafter, a case where a transmission time interval of a physical channel is a subframe are described as an example. For example, a case where a minimum time interval from the start of transmission of one physical channel (e.g., NPDCCH, NPDSCH, NPUCCH, NPUSCH) to the start of transmission of a next physical channel is one subframe will be described, but in the following description, the subframe may be replaced by a slot, a mini-slot, or multiple slots.

Frame Structure and Physical Resource of NB-IoT

Figure 29:
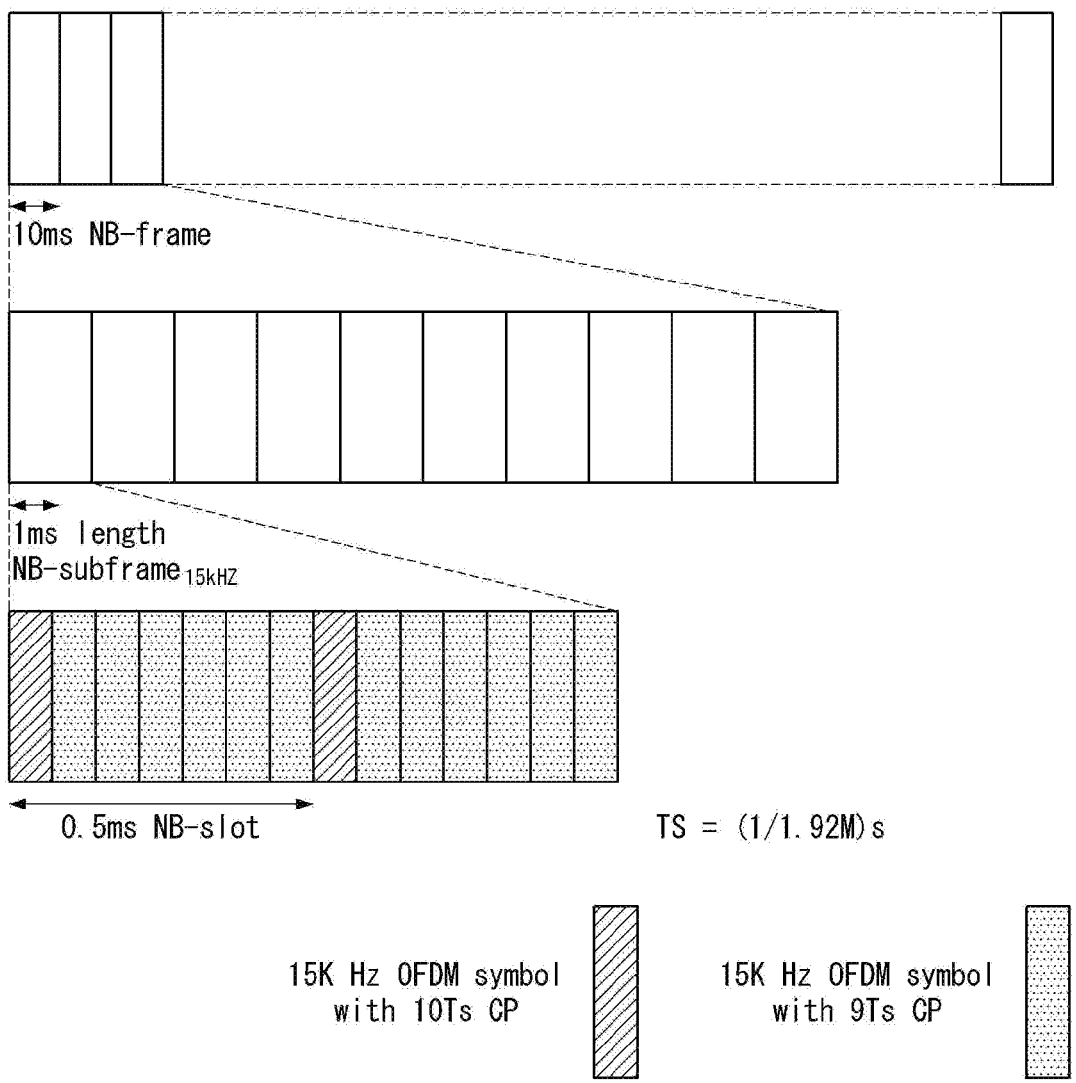
FIG. 29 shows an example of a frame structure when a subcarrier spacing is 15 kHz.
Figure 30:
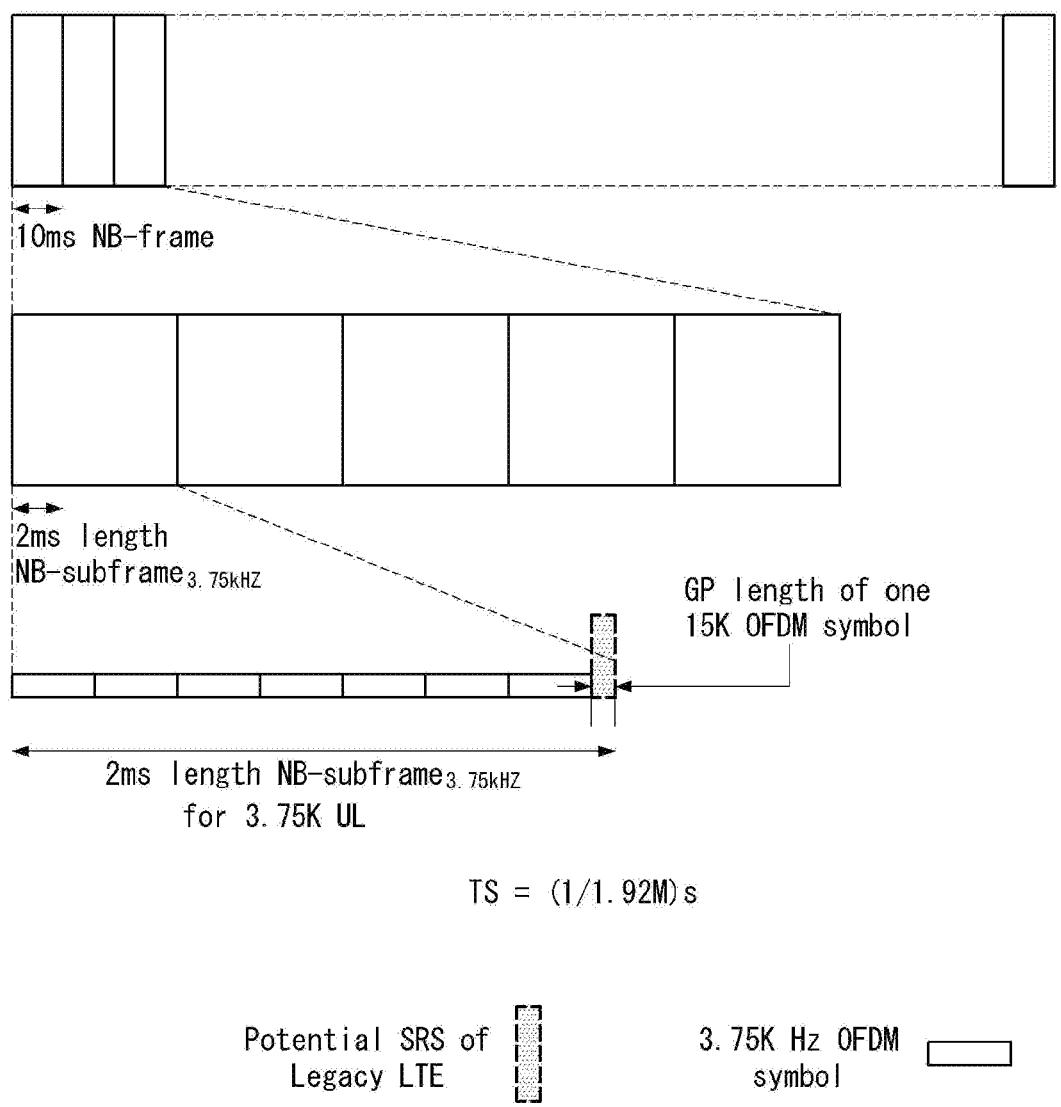
FIG. 30 shows an example of a frame structure when a subscriber spacing is 3.75 kHz.

First, the NB-IoT frame structure may be configured to be different according to subcarrier spacing. Specifically, FIG. 29 shows an example of a frame structure when a subscriber spacing is 15 kHz, and FIG. 30 shows an example of a frame structure when a subscriber spacing is 3.75 kHz. However, the NB-IoT frame structure is not limited thereto, and NB-IoT for other subscriber spacings (e.g., 30 kHz) may be considered with different time/frequency units.

In addition, although the NB-IoT frame structure on the basis of the LTE system frame structure has been exemplified in the present specification, it is merely for the convenience of explanation and the present invention is not limited thereto. The method described in this disclosure may also be extendedly applied to NB-IoT based on a frame structure of a next-generation system (e.g., NR system).

Referring to FIG. 29, the NB-IoT frame structure for a 15 kHz subscriber spacing may be configured to be the same as the frame structure of the legacy system (e.g., LTE system) described above. For example, a 10 ms NB-IoT frame may include ten 1 ms NB-IoT subframes, and the 1 ms NB-IoT subframe may include two 0.5 ms NB-IoT slots. Further, each 0.5 ms NB-IoT may include 7 OFDM symbols.

Alternatively, referring to FIG. 30, the 10 ms NB-IoT frame may include five 2 ms NB-IoT subframes, the 2 ms NB-IoT subframe may include seven OFDM symbols and one guard period (GP). Also, the 2 ms NB-IoT subframe may be represented by an NB-IoT slot or an NB-IoT RU (resource unit).

Next, physical resources of the NB-IoT for each of downlink and uplink will be described.

First, the physical resources of the NB-IoT downlink may be configured by referring to physical resources of other wireless communication system (e.g., LTE system, NR system, etc.), except that a system bandwidth is limited to a certain number of RBs (e.g., one RB, i.e., 180 kHz). For example, when the NB-IoT downlink supports only the 15-kHz subscriber spacing as described above, the physical resources of the NB-IoT downlink may be configured as resource regions limiting a resource grid of the LTE system shown in FIG. 31 to one RB in the frequency domain.

Figure 31:
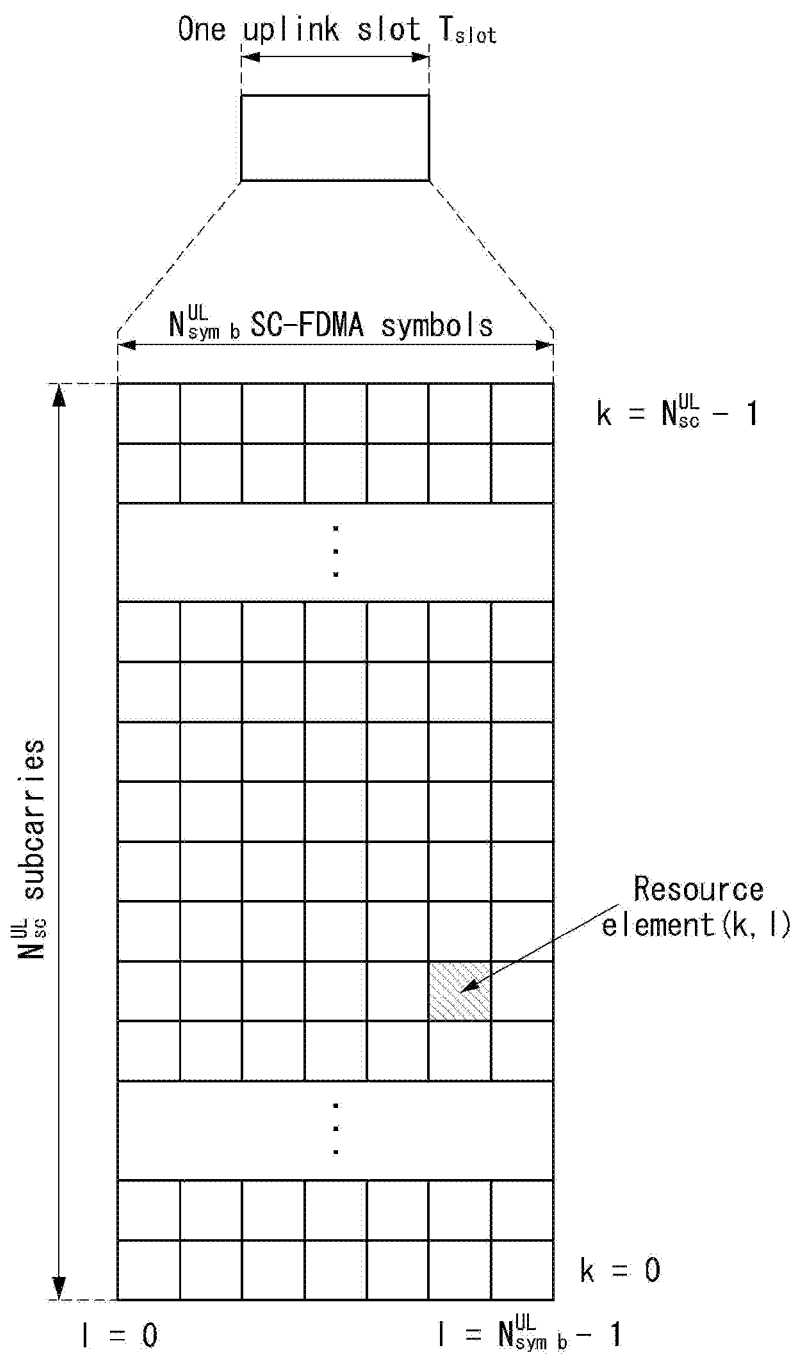
FIG. 31 shows an example of a resource grid for NB-IoT uplink.

Next, in the case of the NB-IoT uplink physical resource, the system bandwidth may be limited to one RB as in the case of downlink. For example, if the NB-IoT uplink supports 15 kHz and 3.75 kHz subscriber spacings as described above, a resource grid for the NB-IoT uplink may be expressed as shown in FIG. 31. In this case, the number of subcarriers NULsc and the slot period Tslot in the uplink band in FIG. 31 may be given as shown in Table 9 below.

TABLE 9

| Subcarrier spacing | NULsc | Tslot |
|---|---|---|
| Δf = 3.75 kHz | 48 | 6144 · Ts |
| Δf = 15 kHz | 12 | 15360 · Ts |

In NB-IoT, resource units (RUs) are used for mapping the PUSCH for NB-IoT (hereinafter referred to as NPUSCH) to resource elements. RU may include NULsymb*NULslot SC-FDMA symbols in the time domain and include NRUsc number of consecutive subcarriers in the frequency domain. For example, NRUsc and NULsymb may be given by Table 10 below for frame structure type 1, which is a frame structure for FDD, and may be given by Table 11 below for frame structure type 2, which is frame structure for TDD.

TABLE 10

| NPUSCH format | Δf | NRUsc | NULslots | NULsymb |
|---|---|---|---|---|
| 1 | 3.75 kHz | 1 | 16 | 7 |
|   | 15 kHz | 1 | 16 |   |
|   |   | 3 | 8 |   |
|   |   | 6 | 4 |   |
|   |   | 12 | 2 |   |
| 2 | 3.75 kHz | 1 | 4 |   |
|   | 15 kHz | 1 | 4 |   |

TABLE 11

| NPUSCH format | Δf | Supported uplink-downlink configurations | NRUsc | NULslots | NULsymb |
|---|---|---|---|---|---|
| 1 | 3.75 kHz | 1, 4 | 1 | 16 | 7 |
|   | 15 kHz | 1, 2, 3, 4, 5 | 1 | 16 |   |
|   |   |   | 3 | 8 |   |
|   |   |   | 6 | 4 |   |
|   |   |   | 12 | 2 |   |
| 2 | 3.75 kHz | 1, 4 | 1 | 4 |   |
|   | 15 kHz | 1, 2, 3, 4, 5 | 1 | 4 |   |

Physical Channel of NB-IoT

A BS and/or a UE supporting the NB-IoT may be configured to transmit/receive physical channels and/or physical signals configured separately from the legacy system. Hereinafter, specific contents related to physical channels and/or physical signals supported by the NB-IoT will be described.

An orthogonal frequency division multiple access (OFDMA) scheme may be applied to the NB-IoT downlink on the basis of a subscriber spacing of 15 kHz. Through this, co-existence with other systems (e.g., LTE system, NR system) may be efficiently supported by providing orthogonality between subcarriers. A downlink physical channel/signal of the NB-IoT system may be represented by adding 'N (Narrowband)' to distinguish it from the legacy system. For example, a downlink physical channel may be referred to as an NPBCH (narrowband physical broadcast channel), an NPDCCH (narrowband physical downlink control channel), or an NPDSCH (narrowband physical downlink shared channel), and a downlink physical signal may be referred to as an NPSS (narrowband primary synchronization signal), an NSSS (narrowband secondary synchronization signal), an NRS (narrowband reference signal), an NPRS (narrowband positioning reference signal), an NWUS (narrowband wake up signal), and the like. Generally, the downlink physical channels and physical signals of the NB-IoT may be configured to be transmitted on the basis of a time domain multiplexing scheme and/or a frequency domain multiplexing scheme. In the case of NPBCH, NPDCCH, NPDSCH, etc., which are the downlink channels of the NB-IoT system, repetition transmission may be performed for coverage enhancement. In addition, the NB-IoT uses a newly defined DCI format. For example, the DCI format for NB-IoT may be defined as DCI format N0, DCI format N1, DCI format N2, and the like.

In the NB-IoT uplink, a single carrier frequency division multiple access (SC-FDMA) scheme may be applied on the basis of a subscriber spacing of 15 kHz or 3.75 kHz. As mentioned in the downlink section, the physical channel of the NB-IoT system may be expressed by adding 'N (Narrowband)' to distinguish it from the existing system. For example, the uplink physical channel may be represented by a narrowband physical random access channel (NPRACH) or a narrowband physical uplink shared channel (NPUSCH), and the uplink physical signal may be represented by a narrowband demodulation reference signal (NDMRS), or the like. NPUSCH may be divided into NPUSCH format 1 and NPUSCH format 2. In one example, NPUSCH Format 1 may be used for uplink shared channel (UL-SCH) transmission (or transport), and NPUSCH Format 2 may be used for uplink control information transmission such as HARQ ACK signaling. In the case of NPRACH, which is an uplink channel of the NB-IoT system, repetition transmission may be performed for coverage enhancement. In this case, repetition transmission may be performed by applying frequency hopping.

Multi-Carrier Operation of NB-IoT

Next, a multi-carrier operation of the NB-IoT will be described. The multicarrier operation may refer to that multiple carriers set for different uses (i.e., different types) are used for transmitting/receiving channels and/or signals between the BS and/or UE in the NB-Iot.

The NB-IoT may operate in a multi-carrier mode. Here, in the NB-IoT, a carrier wave in the N-Iot may be classified as an anchor type carrier (i.e., an anchor carrier, an anchor PRB) and a non-anchor type carrier a non-anchor type carrier (i.e., non-anchor carrier).

The anchor carrier may refer to a carrier that transmits NPSS, NSSS, NPBCH, and NPDSCH for a system information block (N-SIB) for initial access from a point of view of the BS. That is, in NB-IoT, the carrier for initial access may be referred to as an anchor carrier and the other(s) may be referred to as a non-anchor carrier. Here, only one anchor carrier wave may exist in the system, or there may be a plurality of anchor carrier waves.

Operation Mode of NB-IoT

Figure 32:
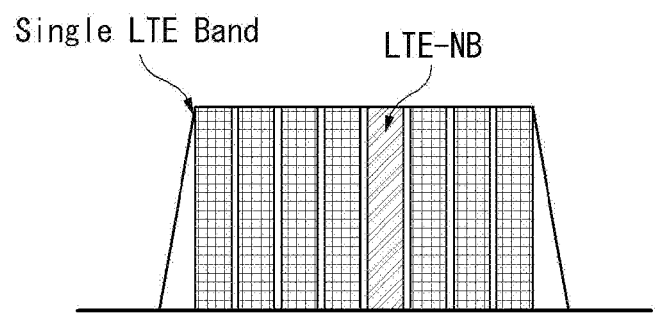
FIG. 32 shows an example of an NB-IoT operation mode.
Figure 32:
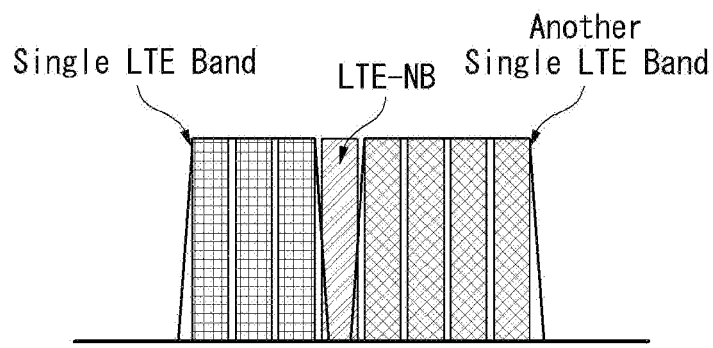
Figure 32:
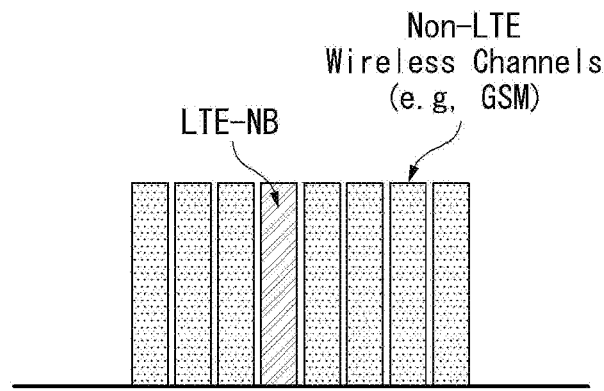

Next, an operation mode of the NB-IoT will be described. In the NB-IoT system, three operation modes may be supported. FIG. 32 shows an example of operation modes supported in the NB-IoT system. Although the operation mode of the NB-IoT is described herein on the basis of an LTE band, this is for convenience of explanation and may be extendedly applied to other system bands (e.g. NR system band).

Specifically, part (a) of FIG. 32 shows an example of an in-band system, part (b) of FIG. 32 shows an example of a guard-band system, and part (c) of FIG. 32 represents an example of a stand-alone system. In this case, the in-band system may be expressed as an in-band mode, the guard-band system may be expressed as a guard-band mode, and the stand-alone system may be expressed in a stand-alone mode.

The in-band system may refer to a system or mode that uses a specific RB in the (legacy) LTE band. The in-band system may be operated by allocating some resource blocks of the LTE system carrier.

A guard-band system may refer to a system or mode that uses NB-IoT in a space reserved for a guard-band of the legacy LTE band. The guard-band system may be operated by allocating a guard-band of an LTE carrier not used as a resource block in the LTE system. For example, the (legacy) LTE band may be configured to have a guard-band of at least 100 kHz at the end of each LTE band, and with two non-contiguous guard-bands for 200 kHz for NB-IoT may be used.

As described above, the in-band system and the guard-band system may be operated in a structure in which NB-IoT coexists in the (legacy) LTE band.

By contrast, the stand-alone system may refer to a system or mode that is configured independently of the legacy LTE band. The stand-alone system may be operated by separately allocating frequency bands (e.g., reassigned GSM carriers in the future) used in a GERAN (GSM EDGE radio access network).

The three operation modes described above may be operated independently of each other, or two or more operation modes may be operated in combination.

NB-IoT Signal Transmission/Reception Process

Figure 33:
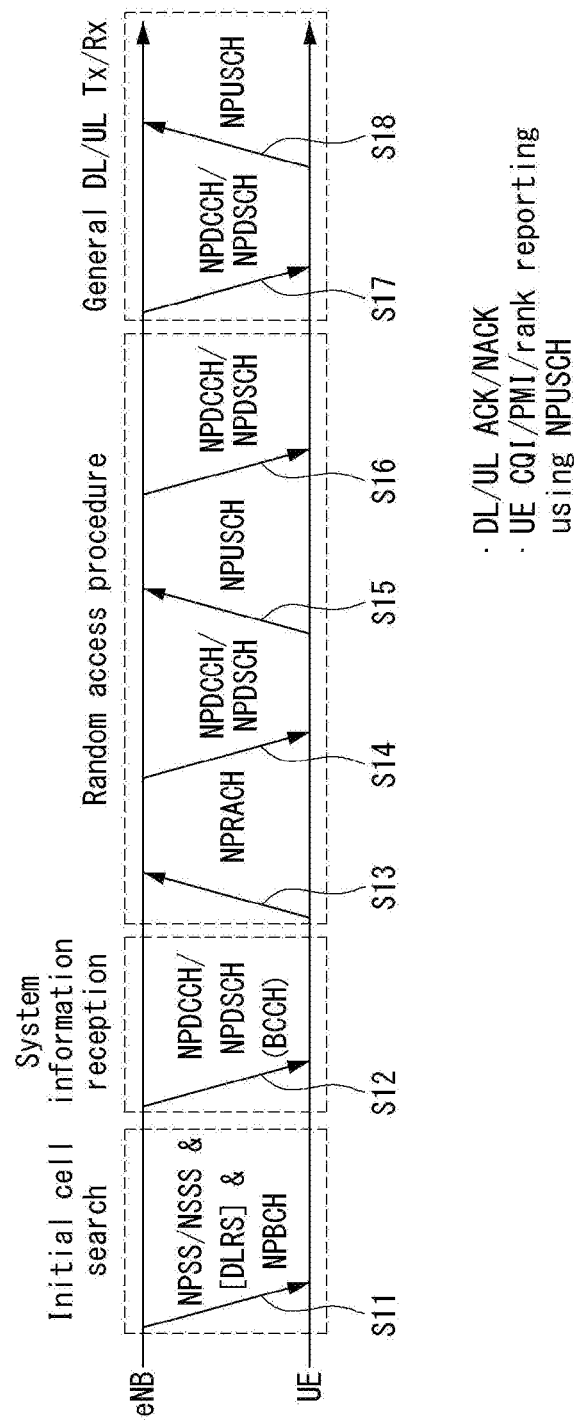
FIG. 33 is a diagram illustrating an example of physical channels that may be used for NB-IoT and a general signal transmission method using the same.

FIG. 33 is a diagram illustrating an example of physical channels that may be used for NB-IoT and a general signal transmission method using the same. In a wireless communication system, an NB-IoT UE may receive information from a BS through a downlink (DL) and the NB-IoT UE may transmit information to the BS through an uplink (UL). In other words, in the wireless communication system, the BS may transmit information to the NB-IoT UE through the downlink and the BS may receive information from the NB-IoT UE through the uplink.

The information transmitted/received by the BS and the NB-IoT UE includes data and various control information, and various physical channels may exist depending on the type/purpose of the information transmitted/received by the BS and NB-IoT UE. The signal transmission/reception method of the NB-IoT may be performed by the above-described wireless communication devices (e.g., BS and UE).

The NB-IoT UE, which is powered on again or enters a new cell, may perform an initial cell search operation such as adjusting synchronization with the BS, or the like (S11). To this end, the NB-IoT UE receives NPSS and NSSS from the BS, performs synchronization with the BS, and acquires cell identity information. Also, the NB-IoT UE may receive the NPBCH from the BS and acquire the in-cell broadcast information. In addition, the NB-IoT UE may receive a DL RS (downlink reference signal) in the initial cell search step to check a downlink channel state.

After completion of the initial cell search, the NB-IoT UE may receive the NPDCCH and the corresponding NPDSCH to acquire more specific system information (S12). In other words, the BS may transmit more specific system information by transmitting the NPDCCH and corresponding NPDSCH to the NB-IoT UE after completion of the initial cell search.

Thereafter, the NB-IoT UE may perform a random access procedure to complete connection to the BS (S13 to S16).

Specifically, the NB-IoT UE may transmit a preamble to the BS via the NPRACH (S13). As described above, the NPRACH may be configured to be repeatedly transmitted on the basis of frequency hopping or the like to enhance coverage or the like. In other words, the BS may (repeatedly) receive a preamble through the NPRACH from the NB-IoT UE.

Thereafter, the NB-IoT UE may receive a random access response (RAR) for the preamble from the BS through the NPDCCH and the corresponding NPDSCH (S14). In other words, the BS may transmit the RAR for the preamble to the NB-IoT UE through the NPDCCH and the corresponding NPDSCH.

Thereafter, the NB-IoT UE transmits the NPUSCH to the BS using scheduling information in the RAR (S15), and may perform a contention resolution procedure such as the NPDCCH and the corresponding NPDSCH (S16). In other words, the BS may receive the NPUSCH from the UE using the scheduling information in the NB-IoT RAR, and perform the contention resolution procedure.

The NB-IoT UE that has performed the above-described process may perform NPDCCH/NPDSCH reception (S17) and NPUSCH transmission (S18) as a general uplink/downlink signal transmission process. In other words, after performing the above-described processes, the BS may perform NPDCCH/NPDSCH transmission and NPUSCH reception as a general signal transmission/reception process to the NB-IoT UE.

In the case of NB-IoT, as mentioned above, NPBCH, NPDCCH, NPDSCH, and the like may be repeatedly transmitted for coverage improvement and the like. In the case of NB-IoT, UL-SCH (i.e., general uplink data) and uplink control information may be transmitted through the NPUSCH. Here, the UL-SCH and the uplink control information (UCI) may be configured to be transmitted through different NPUSCH formats (e.g., NPUSCH format 1, NPUSCH format 2, etc.).

Also, the UCI may include HARQ ACK/NACK (Hybrid Automatic Repeat and reQuest Acknowledgement/Negative-ACK), SR (Scheduling Request), CSI (Channel State Information), and the like. As described above, the UCI in the NB-IoT may generally be transmitted via the NPUSCH. Also, in response to a request/instruction from the network (e.g., BS), the UE may transmit the UCI via the NPUSCH in a periodic, aperiodic, or semi-persistent manner.

Hereinafter, the wireless communication system block diagram shown in FIG. 1 will be described in detail.

N. Wireless Communication Device

Referring to FIG. 1, a wireless communication system includes a first communication device 910 and/or a second communication device 920. 'A and/or B' may be interpreted to have the same meaning as 'includes at least one of A or B.' The first communication device may represent a BS and the second communication device may represent a UE (alternatively, the first communication device may represent a UE and the second communication device may represent a BS).

The first and second communication devices may include processors 911 and 921, memories 914 and 924, one or more Tx/Rx RF modules 915 and 925, Tx processors 912 and 922, Rx processors 913 and 923, and antennas 916 and 926, respectively. The Tx/Rx module is also called a transceiver. The processor implements the functions, procedures and/or methods discussed above. More specifically, in the DL (communication from the first communication device to the second communication device), a higher layer packet from the core network is provided to the processor 911. The processor implements the function of a layer 2 (i.e., L2) layer. In the DL, the processor multiplexes a logical channel and a transport channel, provides radio resource allocation to the second communication device 920, and is responsible for signaling to the second communication device. A transmission (TX) processor 912 implements various signal processing functions for the L1 layer (i.e., the physical layer). The signal processing function facilitates forward error correction (FEC) in the second communication device, and includes coding and interleaving. The encoded and interleaved signals are scrambled and modulated into complex-valued modulation symbols. For modulation, BPSK (Quadrature Phase Shift Keying), QPSK (Quadrature Phase Shift Keying), 16QAM (quadrature amplitude modulation), 64QAM, 246QAM, and the like may be used. The complex-valued modulation symbols (hereinafter referred to as modulation symbols) are divided into parallel streams, each stream being mapped to an OFDM subcarrier and multiplexed with a reference signal (RS) in the time and/or frequency domain, and combined together using IFFT (Inverse Fast Fourier Transform) to create a physical channel carrying a time domain OFDM symbol stream. The OFDM symbol stream is spatially precoded to produce multiple spatial streams. Each spatial stream may be provided to a different antenna 916 via a separate Tx/Rx module (or transceiver, 915). Each Tx/Rx module may upconvert each spatial stream into an RF carrier for transmission. In the second communication device, each Tx/Rx module (or transceiver, 925) receives a signal of the RF carrier via each antenna 926 of each Tx/Rx module. Each Tx/Rx module restores the RF carrier signal to a baseband signal and provides it to the reception (RX) processor 923. The RX processor implements various signal processing functions of the L1 (i.e., the physical layer). The RX processor may perform spatial processing on the information to recover any spatial stream directed to the second communication device. If multiple spatial streams are directed to the second communication device, they may be combined into a single OFDMA symbol stream by multiple RX processors. The RX processor transforms the OFDM symbol stream, which is a time domain signal, into a frequency domain signal using a fast Fourier transform (FFT). The frequency domain signal includes a separate OFDM symbol stream for each subcarrier of the OFDM signal. The modulation symbols and the reference signal on each subcarrier are recovered and demodulated by determining the most likely signal constellation points sent by the first communication device. These soft decisions may be based on channel estimate values. Soft decisions are decoded and deinterleaved to recover data and control signals originally transmitted by the first communication device on the physical channel. The corresponding data and control signals are provided to the processor 921.

The UL (communication from the second communication device to the first communication device) is processed in the first communication device 910 in a manner similar to that described in connection with a receiver function in the second communication device 920. Each Tx/Rx module 925 receives a signal via each antenna 926. Each Tx/Rx module provides an RF carrier and information to RX processor 923. The processor 921 may be related to the memory 924 that stores program code and data. The memory may be referred to as a computer-readable medium.

The 5G communication technology discussed above may be applied in combination with the methods proposed in the present disclosure to be described later, or may be used as a supplement to embody or clarify the technical features of the methods proposed in the present disclosure.

Light Therapy System Based on Intelligent IoT

Figure 34:
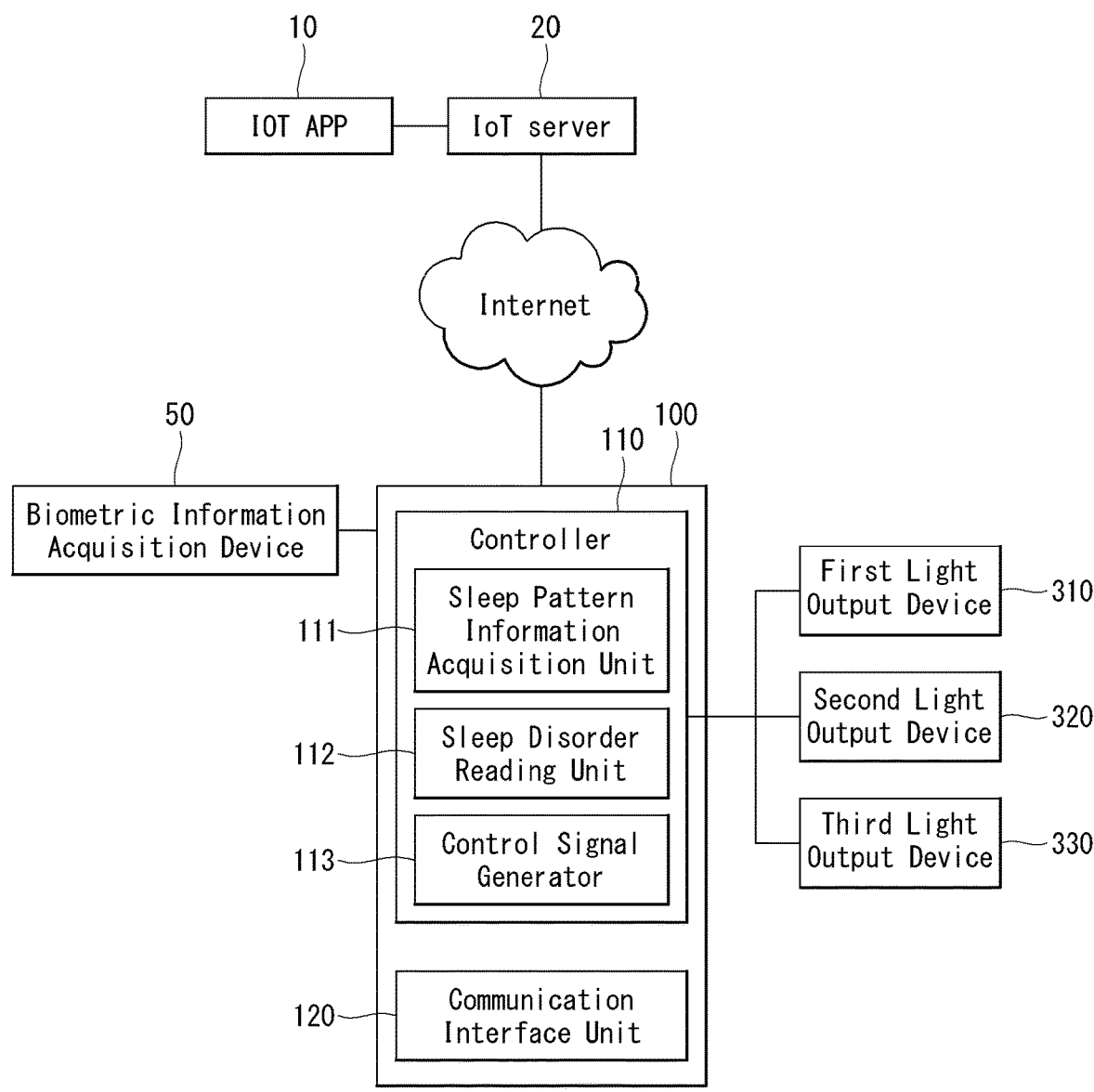
FIG. 34 illustrates a light therapy system based on intelligent Internet of Things (IoT) according to an embodiment of the present invention.

FIG. 34 illustrates a light therapy system based on intelligent Internet of Things (IoT) according to an embodiment of the present invention.

Referring to FIG. 34, an intelligent light therapy system based on IoT according to an embodiment of the present invention includes an IoT application 10, an IoT server 20, a biometric information acquisition device 50, an IoT hub 100, and light output devices 310, 320, and 330.

The IoT application 10 may provide a user interface (UI) through which a user can directly control the first to third light output devices 310, 320, and 330.

The IoT server 20 may connect the first to third light output devices 310, 320, and 330 to the IoT application 10 over internet network. The IoT server 20 may include a cloud server associated with the first to third light output devices 310, 320, and 330 and the IoT application 10 and may include a database regarding an IoT system. The IoT server 20 may perform analysis using big data based on the database.

The IoT hub 100 controls at least one of the first to third light output devices 310, 320, and 330.

A communication interface unit 120 of the IoT hub 100 may accept wired or wireless communication technology to interpret signals of the first to third light output devices 310, 320, and 330 using different protocols and may control the first to third light output devices 310, 320, and 330 based on it. The IoT hub 100 may receive biometric information from the biometric information acquisition device 50 through the communication interface unit 120. Further, the IoT hub 100 may analyze the biometric information from the biometric information acquisition device 50 and may receive obtained sleep pattern information.

The IoT hub 100 may integrate different protocols of IoT terminals. That is, the IoT hub 100 may include an integrated standard for connecting each of the first to third light output devices 310, 320, and 330 to the IoT server 20 even if the first to third light output devices 310, 320, and 330 are different models. The IoT hub 100 may modify a control signal using the integrated standard. For example, the IoT hub 100 may support various radio interfaces, e.g., WiFi of 2.4 GHz and 5 GHz, 3G/GPRS, Bluetooth, and Xbee. The IoT hub 100 may use MQTT (MQ Telemetry Transport) that is IoT standard messaging protocol.

The IoT hub 100 may function to discover, identify, and authenticate light output devices that are IoT terminals. The IoT hub 100 may serve as an access point (AP) that can connect the first to third light output devices 310, 320, and 330 to the IoT server 20 through radio LAN communication.

Based on the configurations described above, the IoT hub 100 may receive biometric information of the user from the biometric information acquisition device 50 and includes a controller 110 that obtains a sleep pattern of the user based on the biometric information. The controller 110 of the IoT hub 100 determines whether to perform light therapy based on the sleep pattern of the user. To this end, the controller 110 of the IoT hub 100 includes a sleep pattern information acquisition unit 111, a sleep disorder reading unit 112, and a control signal generator 113.

The sleep pattern information acquisition unit 111 acquires sleep pattern information based on the biometric information received from the biometric information acquisition device 50.

The sleep disorder reading unit 112 reads whether there is a sleep disorder based on the sleep pattern information and determines whether the light therapy is performed based on it.

The control signal generator 113 generates a control signal if the sleep disorder reading unit 112 determines to perform the light therapy. The control signal may include a turn-on signal for turning on the light output devices, a turn-off signal for turning off the light output devices, and an illumination control signal for controlling illuminances of the light output devices. The controller 110 determines a therapy time, for which the light therapy is performed, and adjusts a time interval between the turn-on signal and the turn-off signal based on the therapy time.

The IoT hub 100 may use the following AI device in the process of acquiring the sleep pattern and in the process of determining whether to perform the light therapy.

Figure 35:
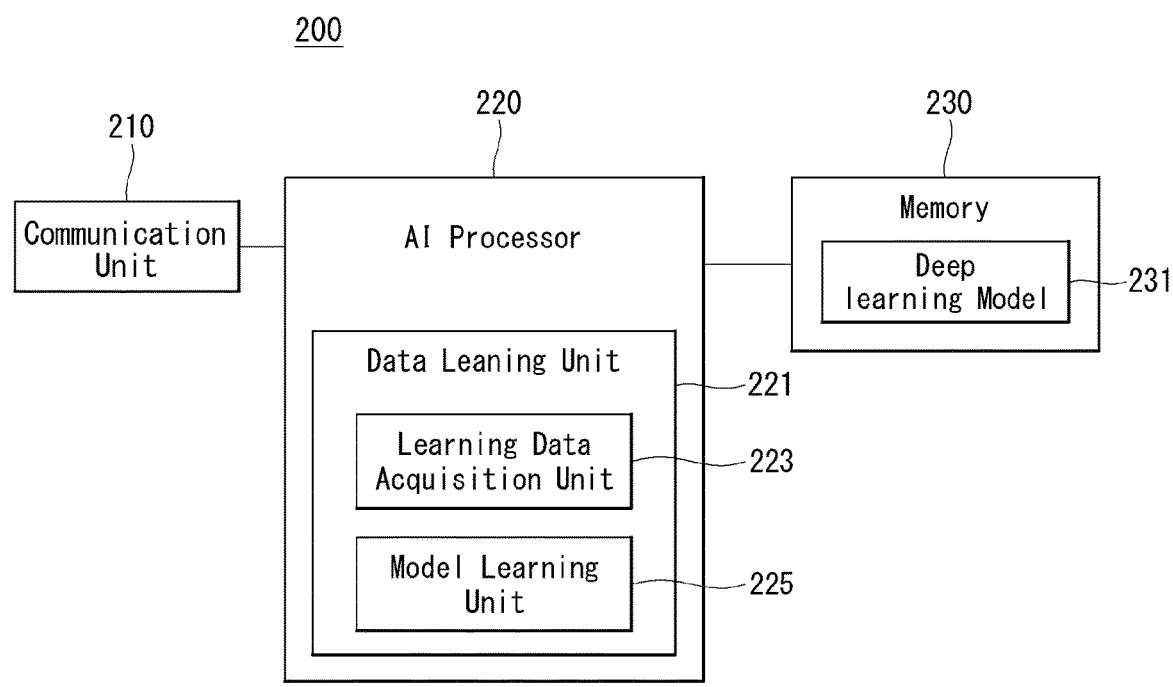
FIG. 35 is a block diagram of an AI device according to an embodiment of the present invention.

FIG. 35 is a block diagram of an AI device according to an embodiment of the present invention.

Referring to FIG. 35, an AI device 200 may include an electronic device including an AI module capable of performing AI processing or a server including an AI module, or the like. The AI device 200 may be included as at least some components of the IoT server 20 or the IoT hub 100 illustrated in FIG. 34 and may perform at least a part of the AI processing.

The AI processing may include all operations related to the control of the IoT server 20 or the IoT hub 100. For example, the IoT hub 100 may perform AI processing on biometric information or sleep pattern information and perform processing/decision operation and a control signal generation operation. The IoT hub 100 may perform AI processing on sleep pattern information to generate a control signal and control at least one of the first to third light output devices 310, 320, and 330 based on the control signal.

The AI device 200 may be a client device directly using a result of the AI processing, or a device in a cloud environment providing a result of the AI processing to another device.

The AI device 200 may include an AI processor 220, a memory 230, and/or a communication unit 210.

The AI device 200 is a computing device capable of learning a neutral network and may be implemented as various electronic devices including a server, a desktop PC, a notebook PC, a tablet PC, and the like.

The AI processor 220 may learn a neural network using a program stored in the memory 230. In particular, the AI processor 220 may learn a neural network for recognizing related data of the IoT hub 100. Here, the neural network for recognizing the related data of the IoT hub 100 may be designed to emulate a human brain structure on a computer and may include a plurality of network nodes with weight that emulate neurons in a human neural network. The plurality of network nodes may send and receive data according to each connection relationship so that neurons emulate the synaptic activity of neurons sending and receiving signals through synapses. Here, the neural network may include a deep learning model, which has evolved from a neural network model. In the deep learning model, the plurality of network nodes may be arranged in different layers and may send and receive data according to a convolution connection relationship. Examples of the neural network model may include various deep learning techniques, such as deep neural networks (DNN), convolutional deep neural networks (CNN), recurrent Boltzmann machine (RNN), restricted Boltzmann machine (RBM), deep belief networks (DBN), and deep Q-networks, and are applicable to fields including computer vision, voice recognition, natural language processing, and voice/signal processing, etc.

A processor performing the above-described functions may be a general purpose processor (e.g., CPU), but may be AI-dedicated processor (e.g., GPU) for AI learning.

The memory 230 may store various programs and data required for the operation of the AI device 200. The memory 230 may be implemented as a non-volatile memory, a volatile memory, a flash memory, a hard disk drive (HDD), or a solid state drive (SSD), etc. The memory 230 may be accessed by the AI processor 220, and the AI processor 220 may read/write/modify/delete/update data. Further, the memory 230 may store a neural network model (e.g., deep learning model 231) created by a learning algorithm for data classification/recognition according to an embodiment of the present invention.

The AI processor 220 may further include a data learning unit 221 for learning a neural network for data classification/recognition. The data learning unit 221 may learn criteria as to which learning data is used to decide the data classification/recognition and how data is classified and recognized using learning data. The data learning unit 221 may learn a deep learning model by acquiring learning data to be used in learning and applying the acquired learning data to the deep learning model.

The data learning unit 221 may be manufactured in the form of at least one hardware chip and mounted on the AI device 200. For example, the data learning unit 221 may be manufactured in the form of a dedicated hardware chip for artificial intelligence (AI), or may be manufactured as a part of a general purpose processor (e.g., CPU) or a graphic-dedicated processor (e.g., GPU) and mounted on the AI device 200. Further, the data learning unit 221 may be implemented as a software module. If the data learning unit 221 is implemented as the software module (or a program module including instruction), the software module may be stored in non-transitory computer readable media. In this case, at least one software module may be provided by an operating system (OS), or provided by an application.

The data learning unit 221 may include a learning data acquisition unit 223 and a model learning unit 225.

The learning data acquisition unit 223 may acquire learning data required for a neural network model for classifying and recognizing data.

By using the acquired learning data, the model learning unit 225 may learn so that the neural network model has a criteria for determining how to classify predetermined data. In this instance, the model learning unit 225 may train the neural network model through supervised learning which uses at least a part of the learning data as the criteria for determination. Alternatively, the model learning unit 225 may train the neural network model through unsupervised learning which finds criteria for determination by allowing the neural network model to learn on its own using the learning data without supervision. Further, the model learning unit 225 may train the neural network model through reinforcement learning using feedback about whether a right decision is made on a situation by learning. Further, the model learning unit 225 may train the neural network model using a learning algorithm including error back-propagation or gradient descent.

If the neural network model is trained, the model learning unit 225 may store the trained neural network model in the memory. The model learning unit 225 may store the trained neural network model in a memory of a server connected to the AI device 200 over a wired or wireless network.

The data learning unit 221 may further include a learning data pre-processing unit (not shown) and a learning data selection unit (not shown), in order to improve a result of analysis of a recognition model or save resources or time required to create the recognition model.

The learning data pre-processing unit may pre-process obtained data so that the obtained data can be used in learning for deciding the situation. For example, the learning data pre-processing unit may process obtained learning data into a predetermined format so that the model learning unit 225 can use the obtained learning data in learning for recognizing images.

Moreover, the learning data selection unit may select data required for learning among learning data obtained by the learning data acquisition unit 223 or learning data pre-processed by the pre-processing unit.

In addition, the data learning unit 221 may further include a model evaluation unit (not shown) for improving the result of analysis of the neural network model.

The model evaluation unit may input evaluation data to the neural network model and may allow the model learning unit 22 to learn the neural network model again if a result of analysis output from the evaluation data does not satisfy a predetermined criterion. In this case, the evaluation data may be data that is pre-defined for evaluating the recognition model. For example, if the number or a proportion of evaluation data with inaccurate analysis result among analysis results of the recognition model learned on the evaluation data exceeds a predetermined threshold, the model evaluation unit may evaluate the analysis result as not satisfying the predetermined criterion.

The communication unit 210 may transmit, to an external electronic device, a result of the AI processing by the AI processor 220.

Although the AI device 200 illustrated in FIG. 35 has been described to be functionally divided into the AI processor 220, the memory 230, the communication unit 210, etc., the above components may be integrated into one module and referred to as an AI module.

The biometric information acquisition device 50 acquires biometric information of the user and transmits the acquired biometric information to the IoT hub 100. The biometric information acquisition device 50 acquires physiological and physical signals from the user during sleep. The biometric information acquisition device 50 may be a device that contacts the user's body to acquire biometric information, such as a sensor belt 11, a body detachable device 12, or a sensor pad 13. Alternatively, the biometric information acquisition device 50 may use a contactless method of acquiring biometric information of the user using a reflected wave of a radar.

The first to third light output devices 310, 320, and 330 include configuration capable of outputting light for light therapy. The first to third light output devices 310, 320, and 330 can be used as long as they include configuration capable of outputting light to at least a part of a device even if they are not an equipment used as a pure light source such as a lamp. For example, the first to third light output devices 310, 320, and 330 may be a mobile terminal such as a smartphone or a display device such as a monitor or TV.

The first to third light output devices 310, 320, and 330 are turned on in response to a turn-on signal and are turned off in response to a turn-off signal. The first to third light output devices 310, 320, and 330 may include a dimming function in which illuminance is adjusted by an illuminance control signal. For example, the first to third light output devices 310, 320, and 330 may use an analog dimming method in which illuminance is adjusted depending on a magnitude of voltage or current. Alternatively, the first to third light output devices 310, 320, and 330 may adjust the illuminance using a pulse width modulation (PWM) method.

The first to third light output devices 310, 320, and 330 is an IoT terminal connected in a home network system that builds an IoT system, and may be wired or wirelessly connected to the IoT hub 100.

The first to third light output devices 310, 320, and 330 may include other device-specific information, such as class or model name or media access control (MAC) address or IP address, as identification information. Identification information and other device-specific information of each of the first to third light output devices 310, 320, and 330 are part of its own information maintained in the IoT system. Thus, the first to third light output devices 310, 320, and 330 each have a name commonly defined by the device manufacturer. For example, the first light output device 310 may have a name of "AA LED lamp", the second light output device 320 may have a name of "BB mobile terminal", and the third light output device 320 may have a name of "XX monitor", Light Therapy Method FIG. 36 is a flow chart illustrating a light therapy method according to an embodiment of the present invention.

Figure 36:
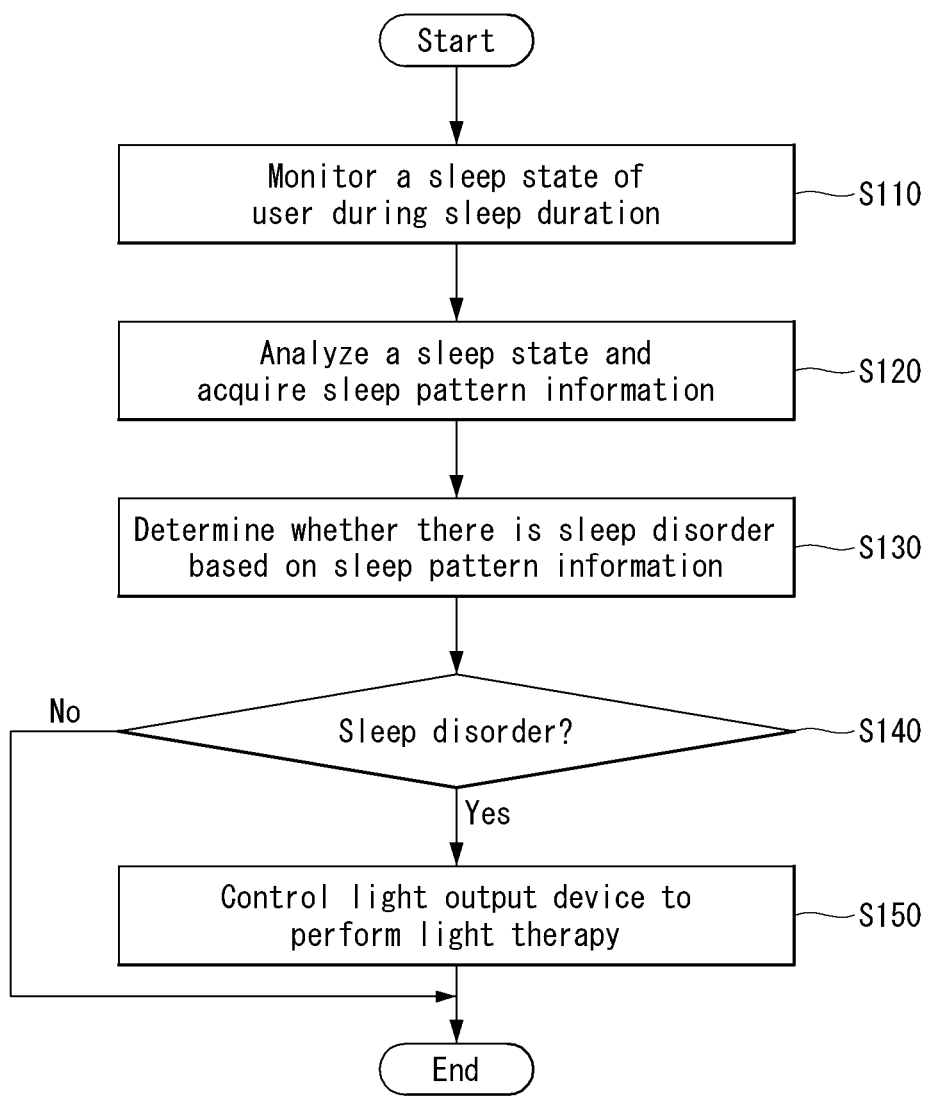
FIG. 36 is a flow chart illustrating a light therapy method according to an embodiment of the present invention.

Referring to FIG. 36, a light therapy method according to the present invention monitors a sleep state in a first step S110.

A method of monitoring the sleep state may be performed based on biometric information of a user.

The biometric information acquisition device 50 acquires the biometric information of the user during a sleep duration of the user.

The biometric information acquisition device 50 may acquire biometric information by contacting the user's body, or acquire biometric information of the user in a contactless method. Examples of the biometric information acquisition device 50 are as follows.

Figure 37:
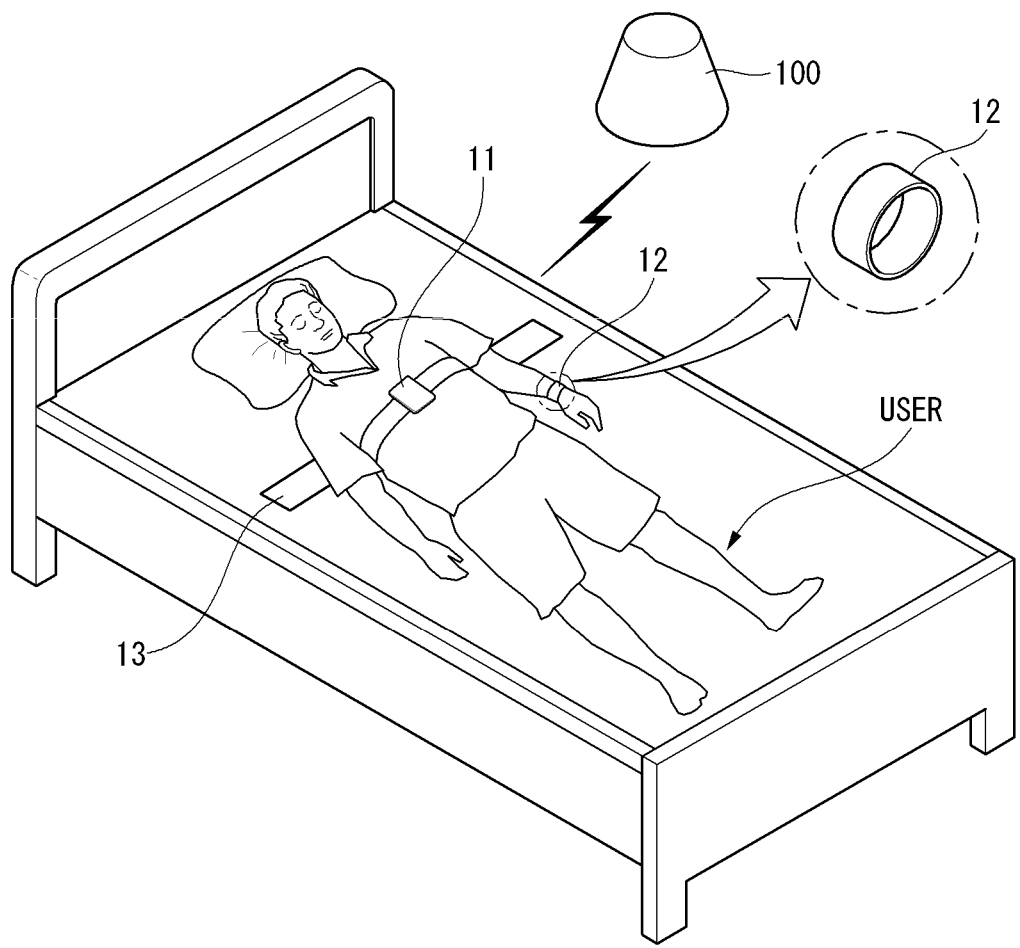
FIG. 37 illustrates a biometric information acquisition device of body contact method.
Figure 38:
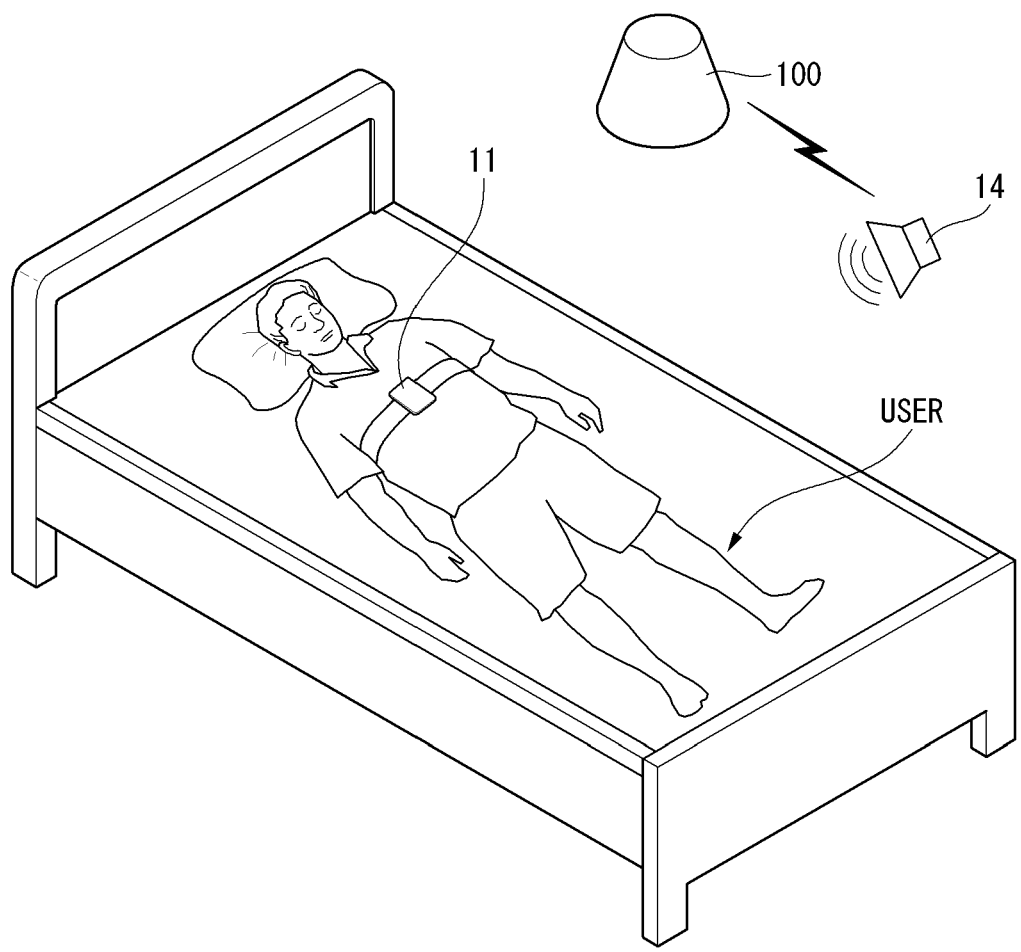
FIG. 38 illustrates a biometric information acquisition device of contactless method.

FIG. 37 illustrates a biometric information acquisition device of body contact method. FIG. 38 illustrates a biometric information acquisition device of contactless method.

Referring to FIG. 37, the biometric information acquisition device 50 may be a sensor belt 11, a body detachable device 12, or a sensor pad 13, etc.

The sensor belt 11 may acquire electroencephalogram (EEG), electrooculaogram (EOG), electromyogram (EMG), electrocardiogram (ECG), arterial oxygen saturation, respiration, and body temperature, etc. The body detachable device 12 may detect a pulse, a respiration rate, etc. by contacting a user's wrist, etc. The sensor pad 13 may be located in a place where the load of the user is applied, and detects a movement, a pulse, etc. of the user.

Referring to FIG. 38, a radar device 14 sends a Tx signal which is a radar signal, and receives an Rx signal corresponding to a reflected wave on which the radar signal is reflected from the user. The radar signal may be a chirp signal whose frequency varies with time. The radar device 14 detects a distance between the user and the radar transceiver 14 and a movement of the user based on a delay degree of the Tx signal and the Rx signal. The Rx signal has a frequency component that is changed by a heart rate or respiration of the user. The radar device 14 may detect a specific frequency to acquire biometric information such as a heart rate or respiration of the user.

The biometric information acquisition device 50 provides the acquired biometric information to the IoT hub 100 in real time.

In a second step S120, the sleep pattern information acquisition unit 111 of the IoT hub 100 analyzes a sleep state and generates sleep pattern information.

The IoT hub 100 checks an end of sleep of the user using the sleep state that is provided in real time. If a time point, at which sleep of the user ends, is checked, the IoT hub 100 generates sleep pattern information based on a sleep state from a sleep start time to a wake-up time. That is, the sleep pattern information includes a sleep phase change information from the sleep start time to the wake-up time.

The sleep phase may be roughly classified into "rapid eye movement (REM) sleep" and "non-REM sleep". The REM sleep indicates a shallow phase of sleep in which the body is close to a sleep state, but the brain is awake. The non-REM sleep indicates that both the body and the brain are in a sleep state. The non-REM sleep may be divided into four stages. A first stage of the non-REM sleep is a section where the brain waves change from beta waves to alpha waves, and a second stage is a section represented by fusiform and K complex brain waves. A third stage and a fourth stage are a section where delta waves starts to come out, and may be distinguished based on an amount of delta waves. The non-REM sleep means a deep sleep state as it is close to the fourth stage.

In a third step S130 and a fourth step S140, it is determined whether to perform light therapy based on the sleep pattern information. The sleep disorder reading unit 112 of the IoT hub 100 decides that a sleep disorder has occurred if the sleep pattern information is abnormal.

The sleep disorder reading unit 112 of the IoT hub 100 may confirm whether it corresponds to the sleep disorder based on a sleep cycle.

For example, the sleep disorder reading unit 112 detects the sleep start time and the wake-up time in the sleep pattern information, and determines a sleep disorder if the sleep start time and the wake-up time are out of a sleep start time and a wake-up time of a normal sleep time by a critical value or more. The sleep start time refers to a time at which the user fell asleep, and may be set to a time at which the user entered the non-REM sleep. The wake-up time refers to a time at which the brain and the body of the user are awake, and may be set to the REM sleep or a complete wake-up moment. Condition of setting the sleep start time and the wake-up time may vary depending on the situation. The critical value may vary depending on a sleep time and a body rhythm, and may be set to, for example, two hours. That is, if the sleep start time or the wake-up time has deviated the normal standards of two or more hours, the sleep disorder reading unit 112 may decide that the sleep disorder has occurred.

Alternatively, if the sleep pattern information corresponds to a sleep pattern of sleep disorders that is previously set, the sleep disorder reading unit 112 may decide that the sleep disorder has occurred.

Figure 39:
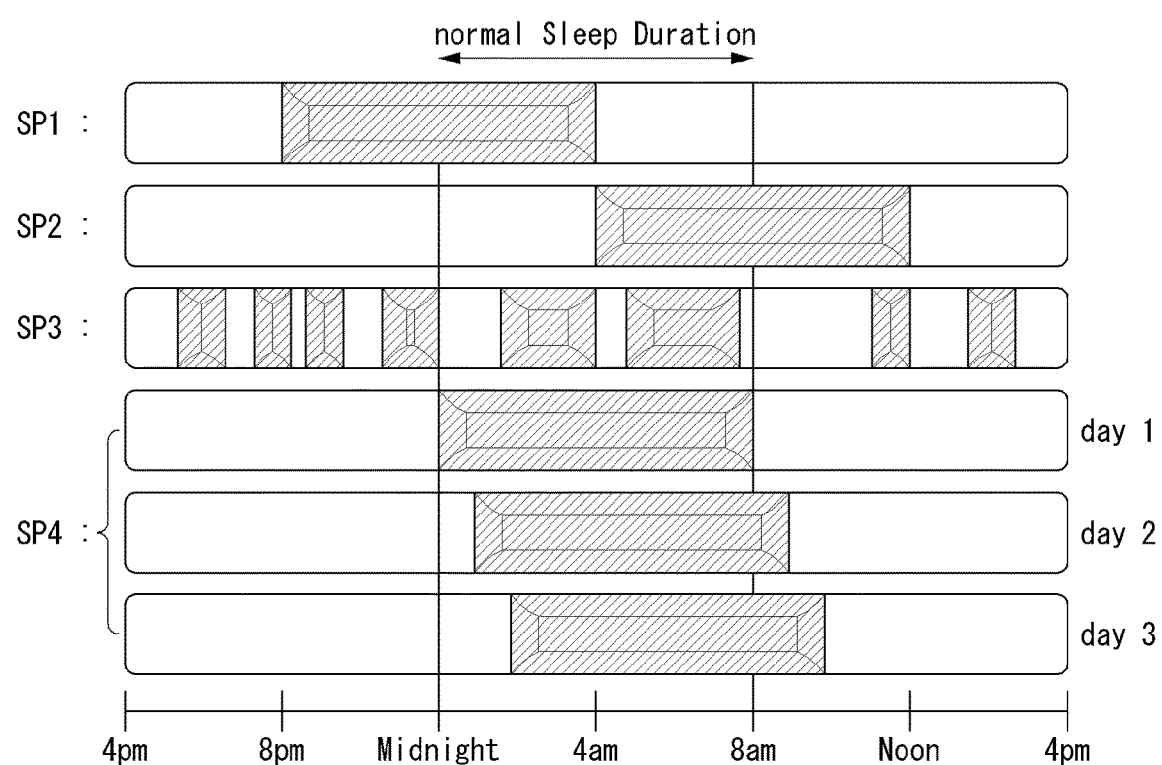
FIG. 39 illustrates a type of a sleep cycle classified as a sleep disorder.

FIG. 39 illustrates a type of a sleep cycle classified as a sleep disorder.

Referring to FIG. 39, a sleep cycle may be defined as a cycle of a sleep start time and a wake-up time. FIG. 39 illustrates an example where a sleep start time of midnight and a wake-up time of 8 am are set as a normal sleep duration.

A first sleep pattern SP1 indicates a sleep pattern in which a sleep start time and a wake-up time are earlier than a normal sleep start time and a normal wake-up time, and may be referred to as an advanced sleep-phase syndrome.

A second sleep pattern SP2 indicates a sleep pattern in which a sleep start time and a wake-up time are more delayed than the normal sleep start time and the normal wake-up time, and may be referred to as a delayed sleep-phase syndrome.

A third sleep pattern SP3 indicates a sleep pattern in which a sleep start time and a wake-up time are not repeated several times in 24 hours such that a sleep cycle is irregular, and may be referred to as an irregular sleep-wake pattern.

A fourth third sleep pattern SP4 indicates a sleep pattern in which a sleep cycle is inconsistent with 24-hour environment such that a sleep start time and a wake-up time are continuously delayed, and may be referred to as a non-24-hour sleep-wake disorder.

In addition to the sleep patterns illustrated in FIG. 39, a time zone change syndrome, a shift work sleep disorder, etc. may be regarded as the sleep disorders. The time zone change syndrome refers to a sleep disorder generated when you have moved to an area with a time difference of two or more hours from the time zone in a short time. The shift work sleep disorder refers to a sleep pattern generated when a sleep cycle has been significantly out of a normal cycle due to shift work.

The IoT hub 100 may determine to perform light therapy when sleep pattern information obtained based on biometric information indicates the sleep patterns corresponding to the sleep disorders illustrated in FIG. 39.

In a fifth step S150, the control signal generator 113 of the IoT hub 100 generates a control signal in response to determining the light therapy.

The control signal includes a turn-on signal for turning on the light output device and a turn-off signal for turning off the light output device. The control signal further includes an illuminance adjusting signal for adjusting an illuminance of light output by the light output device.

The control signal generator 113 generates the control signal according to light therapy conditions as indicated in the following Table 12.

TABLE 12

| Sleep Pattern | Light Therapy Time | Illuminance |
|---|---|---|
| SP1 | ~minute | * Lux |
| SP2 | ~~minute | ** Lux |
| SP3 | ~~~minute | *** Lux |
| SP4 | ~~~~minute | **** Lux |

The IoT hub 100 may include a database including information indicated in Table 12. The database may store light therapy conditions matched to sleep patterns defined as sleep disorders. The control signal generator 113 may search for information of "Light Therapy Time" and "Illuminance" matched to the sleep pattern and may generate the control signal corresponding to the information.

The IoT hub 100 provides the control signal generated by the control signal generator 113 to at least one of the first to third light output devices 310, 320, and 330.

Figure 40:
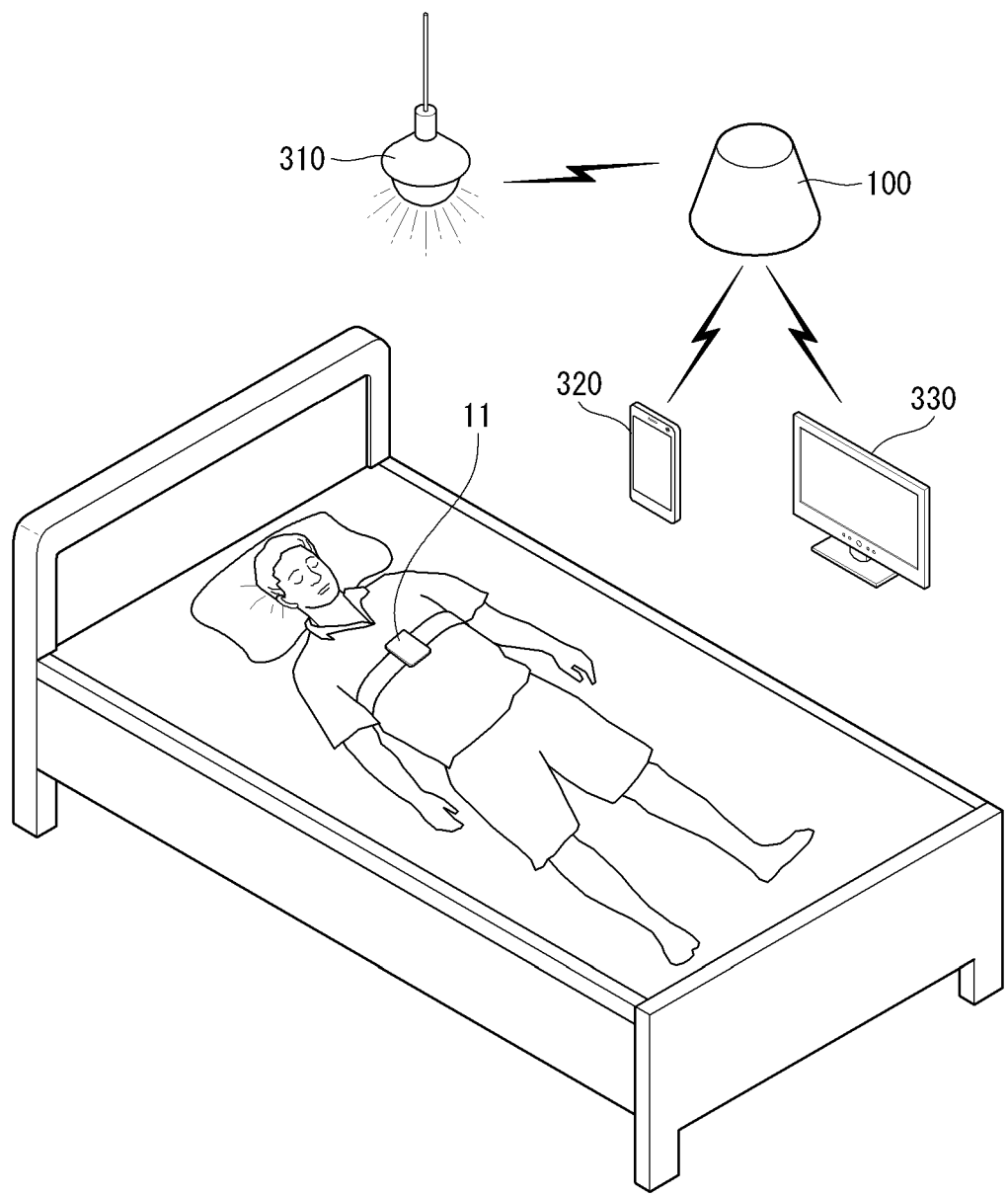
FIG. 40 illustrates an example of light output devices.

FIG. 40 illustrates an example of light output devices.

Referring to FIG. 40, the first light output device 310 is matched to a lamp, the second light output device 320 is matched to a mobile terminal, and the third light output device 320 is matched to a monitor. The IoT hub 100 may perform the light therapy by providing the control signal to at least one of the first to third light output devices 310, 320, and 330. The types and the number of light output devices are limited to FIG. 39.

The IoT hub 100 may search for information of the light output devices in order to select a specific light source among the plurality of light output devices. The IoT hub 100 may search for the light output devices that meet the light therapy conditions determined by the sleep disorder reading unit 112.

For example, the IoT hub 100 searches for the light output devices, that meet the light therapy conditions determined by the sleep disorder reading unit 112, in a database indicated in the following Table 13.

TABLE 13

| Name | Minimum Illuminance (Lux) | Maximum Illuminance (Lux) | Dimming Method | Outputable Color |
|---|---|---|---|---|
| LED Lamp | aa | xx | Analog | White single |
| Mobile Terminal | bb | yy | PWM | Full color |
| Display | cc | zz | PWM | Full color |

Referring to Table 13, "Name" is information identifying the light output devices and may be a commercial name of an electronic device or a unique identification code defined in a database. "Minimum Illuminance" and "Maximum Illuminance" define an illuminance range of light output by a light therapy device. "Dimming Method" means how the light output device adjusts the illuminance. "Outputable Color" means color information of light that the light output device can output.

The controller 110 of the IoT hub 100 searches for information of the light output devices that most meet the light therapy conditions. For example, if the light therapy condition is "white light source of 10,000 Lux or more", the IoT hub 100 may select a LED lamp, that most meets the light therapy condition, as the light output device.

The IoT hub 100 may check whether the light output devices are operable and may reselect the light output device to control based on it. For example, even if a light source that most meets the light therapy condition is the LED lamp, the IoT hub 100 may select another light output device if the LED lamp cannot be operated at a light therapy time. In this instance, the IoT hub 100 may set again the light therapy conditions in the process of reselecting the light output device.

Figure 41:
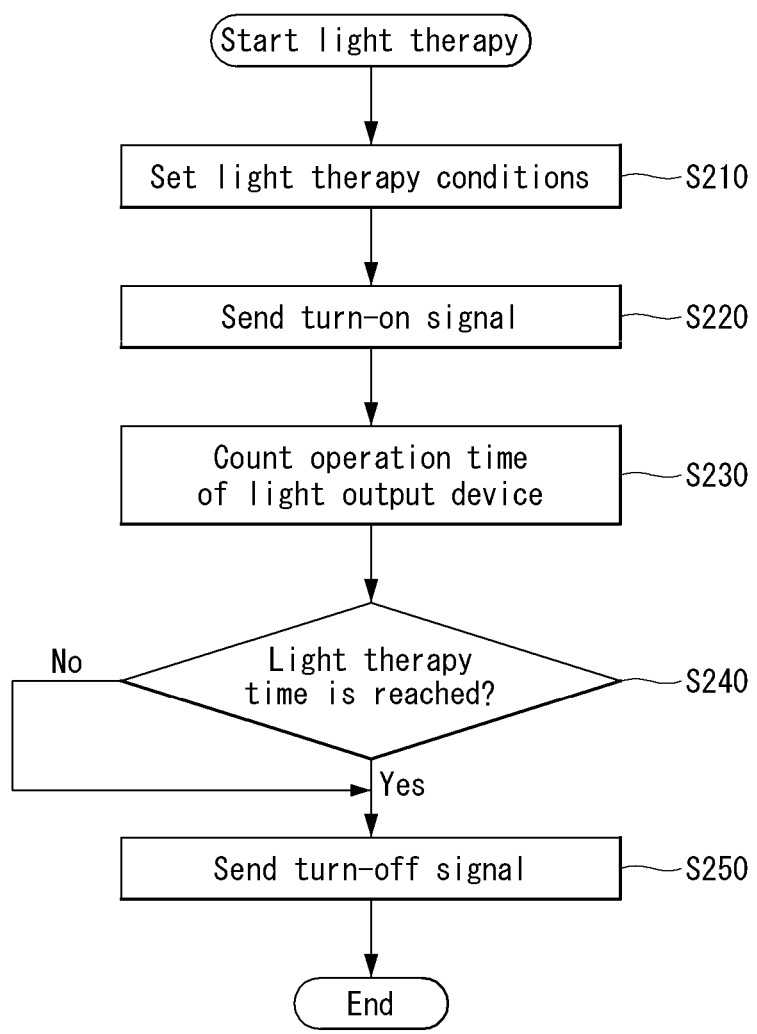
FIG. 41 illustrates an example of adjusting a light therapy time.

FIG. 41 illustrates an example of adjusting a light therapy time.

Referring to FIG. 41, in order to adjust a light therapy time according to an embodiment, in a first step S210, light therapy conditions are set. The controller 110 of the IoT hub 100 sets an operation time and an illuminance of the light output device. The sleep disorder reading unit 112 of the IoT hub 100 may determine whether to perform the light therapy based on the sleep pattern information, and at the same time determine a light therapy time and an illumination of light used for the light therapy.

In a second step S220, the control signal generator 113 of the IoT hub 100 sends a control signal including a turn-on signal to at least one of the first to third light output devices 310, 320, and 330 in response to determining the light therapy.

In a third step S230 and a fourth step S240, the controller 110 of the IoT hub 100 counts time. To this end, the controller 110 may receive a reference clock in which a signal level is inverted at a predetermined cycle, and may include a counter (not shown) that counts a specific signal level of the reference clock. The controller 110 counts time from when the control signal of the turn-on signal is sent to when the light therapy time is reached.

In a fifth step S250, if the light therapy time has passed from time when the turn-on signal is sent, the controller 110 sends a control signal including a turn-off signal to the first to third light output devices 310, 320, and 330.

The present invention may utilize additional information in the process of setting the light therapy conditions. For example, in the process of selecting an illuminance suitable for the light therapy, an illuminance of the light output device may be adjusted in consideration of an ambient illuminance.

Figure 42:
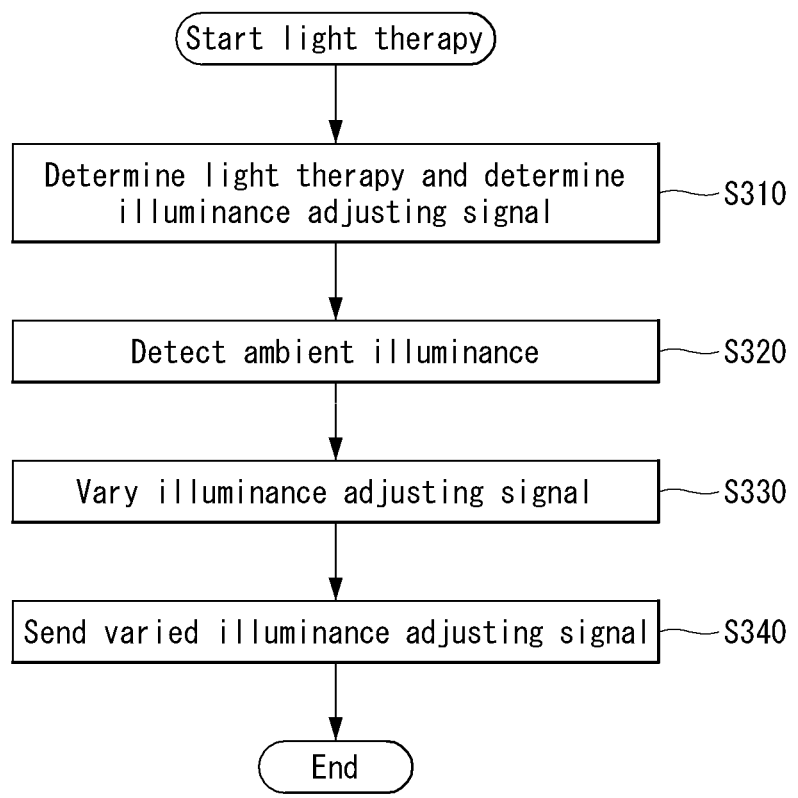
FIG. 42 is a flow chart illustrating an example of setting light therapy conditions.

FIG. 42 is a flow chart illustrating an example of setting light therapy conditions.

Referring to FIG. 42, a method of setting light therapy conditions according to an embodiment of the present invention determines light therapy and determines an illuminance adjusting signal in a first step S310. The step of determining the light therapy may include the first to fourth steps S110 to S140 illustrated in FIG. 36.

In a second step S320, the IoT hub 100 detects an ambient illuminance. To this end, the IoT hub 100 may include an illuminance sensor. Alternatively, the IoT hub 100 may receive illuminance information from a device including an illuminance sensor among IoT terminals belonging to an IoT system.

In a third step S330, the IoT hub 100 varies the illuminance adjusting signal based on the ambient illuminance. For example, if the ambient illuminance is high, the IoT hub 100 may vary the illuminance adjustment signal so that an illuminance of the light output device is controlled at an illuminance lower than an initially set illuminance. In some cases, if the ambient illuminance is considerably high due to natural light, the IoT hub 100 may not turn on the light output device.

The above-described embodiments relate to a method of determining whether light therapy is performed based on a sleep pattern immediately before the wake-up.

The light therapy according to embodiments of the present invention can set light therapy conditions by accumulating sleep pattern information of the user in addition to the sleep pattern immediately before the wake-up.

For example, if the same sleep disorder lasts for several days, a light therapy time may increase.

Alternatively, if a delayed or advanced degree of a predetermined sleep time is continuously maintained though a sleep cycle is out of a normal range, light therapy conditions can be alleviated. For example, when the sleep time outside the normal range lasts for a long time, the IoT hub 100 can reduce the light therapy time.

According to embodiments of the present invention, if the user has a sleep disorder, the side effects caused by the sleep disorder can be treated using the light therapy.

The sleep disorders may cause insomnia, sleepiness, fatigue, and depression, etc. Embodiments of the present invention can cure various symptoms that may occur when awake due to the sleep disorders by using the light therapy that has proved effective in treating the sleep disorders.

In particular, according to embodiments of the present invention, the user can save time and money because the user does not need to have a separate prescription or test a sleep state. In particular, because it takes a long time and you need to sleep in an unfamiliar place in order to determine the sleep disorder using the related art method, it is difficult to expect high accuracy. On the other hand, according to embodiments of the present invention, because a sleep pattern can be analyzed at the user's preferred sleeping place, the sleep pattern can be analyzed without applying psychological burden to the user.

Furthermore, the light therapy method according to embodiments of the present invention is also suitable as an adjuvant treatment because it has no side effects or interactions with other medications.

The configurations described in the present disclosure are merely an example and are not to be considered as limiting the present invention. The scope of the present invention should be determined by rational interpretation of the appended claims, and all changes within the equivalent range of the present invention are included in the scope of the present invention.

The invention claimed is:

1. A hub of intelligent Internet of Things (IoT) for performing a light therapy using light irradiated by a plurality of light output devices, the hub of intelligent IoT comprising:
   a sleep pattern information acquisition unit configured to acquire sleep pattern information based on biometric information received from a biometric information acquisition device via a communication interface unit;
   a sleep disorder reading unit configured to determine whether a sleep disorder has occurred based on the sleep pattern information;
   a control signal generator configured to generate a control signal for controlling the plurality of light output devices;
   the communication interface unit configured to provide the control signal to the plurality of light output devices; and
   a database configured to store a plurality of light therapy conditions corresponding to a plurality of sleep patterns of the sleep disorder,
   wherein the control signal generator is configured to generate the control signal for controlling a light therapy time and an illuminance corresponding to the plurality of light therapy conditions,
   wherein the plurality of light output devices includes a LED lamp, a mobile terminal, and a display, and
   wherein the hub of intelligent IoT is configured to select at least one light output device among the plurality of light output devices that corresponds to at least one light therapy condition among the light therapy conditions, the at least one light therapy condition being determined by the sleep disorder reading unit.

2. The hub of intelligent IoT of claim 1, wherein the sleep disorder reading unit is configured to determine that the sleep disorder has occurred if the sleep pattern information corresponds to a predetermined sleep pattern of a sleep disorder.

3. The hub of intelligent IoT of claim 1, wherein the control signal includes:
   a turn-on signal for controlling a turn-on of the at least one light output device;
   a turn-off signal for controlling a turn-off of the at least one light output device; and
   an illuminance adjusting signal for adjusting an intensity of light irradiated by the at least one light output device.

4. The hub of intelligent IoT of claim 3, wherein the illuminance adjusting signal controls an illuminance of the at least one light output device according to the sleep pattern information.

* * * * *